(12) United States Patent
Krasinski et al.

(10) Patent No.: US 8,546,408 B2
(45) Date of Patent: *Oct. 1, 2013

(54) FUSED HETEROARYL PYRIDYL AND PHENYL BENZENESUFLONAMIDES AS CCR2 MODULATORS FOR THE TREATMENT OF INFLAMMATION

(75) Inventors: Antoni Krasinski, Mountain View, CA (US); Sreenivas Punna, Sunnyvale, CA (US); Solomon Ungashe, Fremont, CA (US); Qiang Wang, Union City, CA (US); Yibin Zeng, San Mateo, CA (US)

(73) Assignee: Chemocentryx, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/976,768

(22) Filed: Dec. 22, 2010

(65) Prior Publication Data
US 2011/0319433 A1 Dec. 29, 2011

Related U.S. Application Data

(63) Continuation of application No. 12/171,782, filed on Jul. 11, 2008, now Pat. No. 7,884,110.

(60) Provisional application No. 60/949,328, filed on Jul. 12, 2007.

(51) Int. Cl.
*A01N 43/90* (2006.01)
*A61K 31/519* (2006.01)
*C07D 487/00* (2006.01)

(52) U.S. Cl.
USPC ........................ 514/265.1; 544/280

(58) Field of Classification Search
None
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,901,855 A | 8/1975 | Arnold | |
| 3,939,350 A | 2/1976 | Kronick et al. | |
| 3,996,345 A | 12/1976 | Ullman et al. | |
| 4,166,452 A | 9/1979 | Generales, Jr. | |
| 4,227,437 A | 10/1980 | Inloes et al. | |
| 4,256,108 A | 3/1981 | Theeuwes | |
| 4,265,874 A | 5/1981 | Bonsen et al. | |
| 4,275,149 A | 6/1981 | Litman et al. | |
| 4,366,241 A | 12/1982 | Tom et al. | |
| 4,403,607 A | 9/1983 | Woo et al. | |
| 5,120,643 A | 6/1992 | Ching et al. | |
| 5,292,758 A | 3/1994 | Yoshino et al. | |
| 5,571,775 A | 11/1996 | Van Heertum et al. | |
| 5,780,488 A | 7/1998 | Bergman et al. | |
| 5,973,148 A | 10/1999 | Ringer et al. | |
| 5,990,479 A | 11/1999 | Weiss et al. | |
| 6,207,392 B1 | 3/2001 | Weiss et al. | |
| 6,251,303 B1 | 6/2001 | Bawendi et al. | |
| 6,306,610 B1 | 10/2001 | Bawendi et al. | |
| 6,312,914 B1 | 11/2001 | Kardos et al. | |
| 6,319,426 B1 | 11/2001 | Bawendi et al. | |
| 6,322,901 B1 | 11/2001 | Bawendi et al. | |
| 6,326,144 B1 | 12/2001 | Bawendi et al. | |
| 6,380,206 B1 | 4/2002 | Pamukcu et al. | |
| 6,403,607 B1 | 6/2002 | Hidaka et al. | |
| 6,423,551 B1 | 7/2002 | Weiss et al. | |
| 6,444,143 B2 | 9/2002 | Bawendi et al. | |
| 6,451,339 B2 | 9/2002 | Patel et al. | |
| 6,479,527 B1 | 11/2002 | Barker et al. | |
| 6,489,452 B1 | 12/2002 | Tateishi et al. | |
| 6,939,885 B2 | 9/2005 | Ungashe et al. | |
| 7,496,807 B2 | 2/2009 | Nagai et al. | |
| 7,622,583 B2 * | 11/2009 | Ungashe et al. | 546/113 |
| 7,884,110 B2 * | 2/2011 | Krasinski et al. | 514/263.22 |
| 2002/0052363 A1 | 5/2002 | Dinsmore et al. | |
| 2002/0103202 A1 | 8/2002 | Pinto et al. | |
| 2003/0229081 A1 | 12/2003 | Maduskuie | |
| 2004/0023286 A1 | 2/2004 | Wei | |
| 2004/0038976 A1 | 2/2004 | Fleming et al. | |
| 2004/0106613 A1 | 6/2004 | McNaughton-Smith | |
| 2004/0171654 A1 | 9/2004 | Ugashe et al. | |
| 2006/0111351 A1 | 5/2006 | Ungashe et al. | |
| 2006/0173019 A1 | 8/2006 | Ungashe et al. | |
| 2007/0021466 A1 | 1/2007 | Ungashe et al. | |
| 2007/0037794 A1 | 2/2007 | Ungashe et al. | |
| 2010/0056509 A1 | 3/2010 | Ungashe et al. | |
| 2010/0234364 A1 | 9/2010 | Basak et al. | |
| 2011/0118248 A1 | 5/2011 | Ungashe et al. | |

FOREIGN PATENT DOCUMENTS

| | | |
|---|---|---|
| DE | 3825041 | 2/1990 |
| EP | 0 472 053 | 2/1992 |
| EP | 0 937 711 | 8/1999 |
| EP | 1 334 719 | 8/2003 |

(Continued)

OTHER PUBLICATIONS

Amann, et al., "ACE Inhibitors Improve Diabetic Nephropathy Through Suppression of Renal MCP-1", *Diabetes Care*, vol. 26(8), pp. 2421-2425, Aug. 2003.
Babu, et al., "Chemokine Receptors of T Cells and of B Cells in Lymphatic Filarial Infection: A Role for CCR9 in Pathogenesis," *J. Infectious Diseases*, vol. 191, pp. 1018-1026 (2005).
Baker, et al., "Puromycin. Synthetic Studies. II. The position of glycosidation on the 6-dimethylarninopurine moiety," *J. Org. Chem.*, vol. 19, pp. 638-645 (1954).
Bendele, et al., "Efficacy of Sustained Blood Levels of Interleukin-1 Receptor Antagonist in Animal Models of Arthritis," *Arthritis & Rheum.*, vol. 42(3), pp. 498-506 (1999).
Bendele, et al., "Animal Models of Arthritis: Relevance to Human Disease," *Toxicologic Pathology*, vol. 27(1), pp. 134-142 (1999).
Berge, et al., "Pharmaceutical Salts", *Journal of Pharmaceutical Sciences*, vol. 66(1), pp. 1-19, Jan. 1977.
Berman, et al.,"Lymphocyte Motility and Lymphocyte Chemoattractant Factors", *Immunol. Invest.*, 17, pp. 625-677, 1988.

(Continued)

*Primary Examiner* — Jeffrey Murray

(74) *Attorney, Agent, or Firm* — Brinks Hofer Gilson & Lione; Ryan L. Marshall; William Boudreaux

(57) ABSTRACT

Fused heteroaryl pyridyl benzenesulfonamides are provided that act as potent antagonists of the CCR2 receptor. The compounds are generally aryl sulfonamide derivatives and are useful in pharmaceutical compositions, methods for the treatment of CCR2-mediated diseases and as controls in assays for the identification of CCR2 antagonists.

11 Claims, 1 Drawing Sheet

(56) References Cited

FOREIGN PATENT DOCUMENTS

| | | |
|---|---|---|
| JP | 61113060 | 5/1986 |
| JP | 04364168 | 12/1992 |
| JP | 06135934 | 5/1994 |
| JP | 06145145 | 5/1994 |
| JP | 2000159665 | 6/2000 |
| JP | 2001089412 | 4/2001 |
| WO | WO 94/20142 | 9/1994 |
| WO | WO 98/11218 | 3/1998 |
| WO | WO 00/40560 | 7/2000 |
| WO | WO 01/00611 | 1/2001 |
| WO | WO 01/02369 | 1/2001 |
| WO | WO 01/72744 | 10/2001 |
| WO | WO 02/101350 | 12/2002 |
| WO | WO 03/032994 | 4/2003 |
| WO | WO 03/051870 | 6/2003 |
| WO | WO 03/099773 | 12/2003 |
| WO | WO 2004/046092 | 6/2004 |
| WO | WO 2004/056774 | 7/2004 |
| WO | WO 2004/058164 | 7/2004 |
| WO | WO 2004/058265 | 7/2004 |
| WO | WO 2004/085384 | 10/2004 |
| WO | WO 2004/099127 | 11/2004 |
| WO | WO 2004/105794 | 12/2004 |
| WO | WO 2005/004810 | 1/2005 |
| WO | WO 2005/028445 | 3/2005 |
| WO | WO 2005/112916 | 12/2005 |
| WO | WO 2005/112925 | 12/2005 |
| WO | WO 2006/076644 | 7/2006 |
| WO | WO 2007/014008 | 1/2007 |
| WO | WO 2007/014054 | 1/2007 |
| WO | WO 2008/008374 | 1/2008 |
| WO | WO 2008/008431 | 1/2008 |
| WO | WO 2009/009740 | 1/2009 |

OTHER PUBLICATIONS

Bredereck, et al, "Synthesen in der Purinreihe," *Chemische Berichte*, vol. 95, pp. 1902-1909 (1962).

Campbell, et al., "Rapid Acquisition of Tissue-specific Homing Phenotypes by CD4+ T Cells Activated in Cutaneous or Mucosal Lymphoid Tissues", *J. Exp. Med.*, vol. 195(1), pp. 135-141, 2002.

Christiansen, et al., "Monocyte chemoattractant protein-1 is produced in isolated adipocytes, associated with adiposity and reduced after weight loss in morbid obese subjects", *International Journal of Obesity*, 29, pp. 146-150, 2005.

Dahinden, et al., "Monocyte Chemotactic Protein 3 Is a Most Effective Basophil- and Eosinophil-activating Chemokine", *J. Exp. Med.*, vol. 179, pp. 751-756, 1994.

Dai, et al., "Monocyte chemoattractant protein-1 expression in renal tissue is associated with monocyte recruitment and tubule-interstitial lesions in patients with lupus nephritis", *Chinese Medical Journal*, vol. 114(8), pp. 864-868, 2001.

Davidson, et al., "T Helper Cell 1-type CD4+T Cells, but Not B Cells, Mediate Colitis in Interleukin 10-deficient Mice", *J. Exp. Med.*, vol. 184, pp. 241-251, 1996.

Deleuran, et al, "Localization of monocyte chemotactic and activating factor (MCAF/MCP-1) in psoriasis", *Journal of Dermatological Science* 13, pp. 228-236, 1996.

Diamond, et al., "Macrophages, monocyte chemoattractant peptide-1, and TGF-β1 in experimental hydronephrosis", *American Journal of Physiology*, vol. 226(6), pp. F926-F933, Jun. 1994.

Dorwald, "Side Reactions in Organic Synthesis: A Guide to Successful Synthesis Design" Wiley-VCH Verlag GmbH & KGaA, Weinheim, Preface, 2005.

Eddy, et al., "Renal expression of genes that promote interstitial inflammation and fibrosis in rats with protein-overload proteinuria", *Kidney International*, vol. 47, pp. 1546-1557, 1995.

Ellingson, et al. "Pyrazine chemistry. III. Derivatives of 3-amino-5,6-dimethylpyrazineic acid," *J. Am. Chem. Soc.*, vol. 70, pp. 1257-1261 (1948).

Feria, Manuel et al., "The CCR2 receptor as a therapeutic target", Expert Opinion on Therapeutic Patents, Informa Healthcare, GB, vol. 16, No. 1, Jan. 1, 2006, pp. 49-57.

Ei-Subbagh, et al., "Novel diarylsulphide derivatives as potential cytotoxic agents", Bollettino Chimico Farmaceutico, 134, pp. 80-84, 1995.

Gillitzer, et al., "MCP-1 mRNA Expression in Basal Keratinocytes of Psoriatic Lesions", *J. Invest Dermatol* 101, pp. 127-131, 1993.

Gong, et al., "An Antagonist of Monocyte Chemoattractant Protein 1 (MCP-1) Inhibits Arthritis in the MRL—Ipr Mouse Model", *J. Exp. Med.*; vol. 186(1), pp. 131-137, Jul. 1997.

Gonzales-Cuadrado, et al., "Expression of leucocyte chemoattractants by interstitial renal fibroblasts: up-regulation by drugs associated with interstitial fibrosis", *Clin. Exp. Immunol.*, 106, pp. 518-522, 1996.

International Search Report App. No. PCT/US2007/015893 (Jan. 22, 2008).

Kavanaugh, et al., "Role of CD11/CD18 in Adhesion and Transendothelial Migration of T Cells", *J. Immunol.*, vol. 146, pp. 4149-4156, Jun. 1991.

Kitagawa, et al., "Blockade of CCR2 Ameliorates Progressive Fibrosis in Kidney", *American Journal of Pathology*, vol. 165(1), pp. 237-246, Jul. 2004.

Kontoyiannis et al., "Impaired On/Off Regulation of TNF Biosynthesis in Mice Lacking TNF AU-Rich Elements: Implications for Joint and Gut-Associated Immunopathologies", *Immunity*, vol. 10, pp. 387-398, Mar. 1999.

Kontoyiannis, et al., "Genetic Dissection of the Cellular Pathways and Signaling Mechanisms in Modeled Tumor Necrosis Factor-induced Crohn's-like Inflammatory Bowel Disease," *J. Exp. Med.*, vol. 196(2), pp. 1563-1574 (2002).

Kosiewicz, et al., "Th1-type responses mediate spontaneous ileitis in a novel murine model of Crohn's disease", *J. Clin. Invest.*, vol. 107(6), pp. 695-702, Mar. 2001.

Kunkel, et al., "Lymphocyte CC Chemokine Receptor 9 and Epithelial Thymus-expressed Chemokine (TECK) Expression Distinguish the Small Intestinal Immune Compartment: Epithelial Expression of Tissue-specific Chemokines as an Organizing Prindiple in Regional Immunity", *J. Exp. Med.* vol. 192(5), pp. 761-777, Sep. 2000.

Kuse, et al., "Novel synthetic route of aryl-aminopyrazine," *Tetrahedron*, vol. 60, pp. 835-840 (2004).

Lloyd, et al., "RANTES and Monocyte Chemoattractant Protein-1 (MCP-1) Play an Important Role in the Inflammatory Phase of Crescentic Nephritis, but Only MCP-1 Is Involved in Crescent Formation and Interstitial Fibrosis", *J. Exp. Med.*, vol. 185(7), pp. 1371-1380, Apr. 1997.

McDonald, et al., "Pyrazine chemistry. II. Derivatives of 3-hydroxypyrazinoic acid," *J. Am. Chem. Soc.*, vol. 69, pp. 1034-1037 (1947).

Mine, et al., "Increased expression levels of monocyte CCR2 and monocyte chemoattractant protein-1 in patients with diabetes mellitus", *Biochemical and Biophysical Research Comm.* 334, pp. 780-785, 2006.

Morii, et al., "Association of monocyte chemoattractant protein-1 with renal tubular damage in diabetic nephropathy", *Journal of Diabetes Complications*, 17, pp. 11-15, 2003.

Murphy, "The Molecular Biology of Leukocyte Chemoattractant Receptors", *Ann. Rev. Immun.*, 12, pp. 593-633, 1994.

Neote, et al., "Molecular Cloning, Functional Expression, and Signaling characteristics of a C-C Chemokine Receptor", *Cell*, vol. 72, pp. 415-425, Feb. 1993.

Ogata, et al., "The Role of Monocyte Chemoattractant Protein-1 (MCP-1) in the Pathogenesis of Collagen-Induced Arthritis in Rats", *Journal of Pathology*, vol. 182, pp. 106-114, 1997.

Panwala, et al., "A Novel Model of Inflammatory Bowel Disease: Mice Deficient for the Multiple Drug Resistance Gene, mdrla, Spontaneously Develop Colitis", *J. Immunol.*, 161, pp. 5733-5744, 1998.

Papadakis, et al., "The Role of Thymus-Expressed Chemokine and Its Receptor CCR9 on Lymphocytes in the Regional Specialization of the Mucosal Immune System", *J. Immunol.*, 165, pp. 5069-5076, 2000.

Papadikis, et al., "CCR9-Positive Lymphocytes and Thymus-Expressed Chemokine Distinguish Small Bowel from Colonic Crohn's Disease," *Gastroenterology*, vol. 121(2), pp. 248-254 (2001).

Plater-Zyberk, et al., "Effect of a CC chemokine receptor antagonist on collagen induced arthritis in DBA/1 mice", *Immunology Letters*, 57, pp. 117-120, 1997.

Powrie et al., "Phenotypically distinct subsets of CD4+ T cells induce or protect from chronic intestinal inflammation in C. B-17 scid mice", *Int. Immunol*, vol. 5(11), pp. 1461-1471, 1993.

Qiuping, et al., "Selectively Increased Expression and Functions of Chemokine Receptor CCR9 on CD4+ T Cells from Patients with T-Cell Lineage Acute Lymphocytic Leukemia", *Cancer Res.*, 63, pp. 6469-6477, Oct. 2003.

Rivera-Nieves, et al., "Antibody Blockade of CCL25/CCR9 Ameliorates Early but not Late Chronic Murine Ileitis," *Gastroenterology*, vol. 131(5), pp. 1518-1529 (2006).

Sartipy, et al., "Monocyte chemoattractant protein 1 in obesity and insulin resistance", *PNAS*, vol. 100(12), pp. 7265-7270, Jun. 2003.

Scaife, et al., "Detection of differentially expressed genes in synovial fibroblasts by restriction fragment differential display", *Rheumatology*, vol. 43(11), pp. 1346-1352, Aug. 2004.

Schall, "Biology of the Rantes/sis Cytokine Family", *Cytokine*, vol. 3(3), pp. 165-183, May 1991.

Schall, et al., "Chemokines, leukocyte trafficking, and inflammation", *Curr. Opin. Immunol.*, 6, pp. 865-873, 1994.

Science IP Search Results (Dec. 16, 2004).

Science IP Search Results (Mar. 29, 2006).

Scifinder Search Results (Jan. 24, 2006)—ether linker.

Scifinder Search Results (Jan. 24, 2006)—keto linker.

Segerer, et al., "Chemokines, Chemokine Receptors, and Renal Disease: From Basic Science to Pathophysiologic and Therapeutic Studies", *J. Am. Soc. Nephrol*, 11, pp. 152-176, 2000.

Sell, et al., "Monocyte Chemotactic Protein-1 Is a Potential Player in the Negative Cross-Talk between Adipose Tissue and Skeletal Muscle", *Endocrinology*, pp. 2458-2467, 2006.

Shadidi, et al., "The Chemokines CCL5, CCL2 and CXCL12 Play Significant Roles in the Migration of Th1 Cells into Rheumatoid Synovial Tissue", *Scandinavia Journal of Immunology* 57, pp. 192-198, 2003.

Shimizu, et al., "Anti-Monocyte Chemoattractant Protein-1 Gene Therapy Attenuates Renal Injury Inducted by Protein-Overload Proteinuria", *J. Am. Soc. Nephrol*, 14, pp. 1496-1505, 2003.

Spreoher, et al, "Methylated purines and pyrimidines, II Synthesis and properties 2,6-diamino-5-(methylamino)-4-pyrimidinol," *Biochemistry*, vol. 4(4), pp. 655-661 (1965).

Stephan, et al., "Urinary Concentration and Tissue Messenger RNA Expression of Monocyte Chemoattractant Protein-1 As An Indicator of the Degree of Hydronephrotic Atrophy in Partial Ureteral Obstruction", *The Journal of Urology*, vol. 167, pp. 1497-1502, Mar. 2002.

Takahashi, et al., "Adiposity Elevates Plasma MCP-1 Levels Leading to the Increased CD11b-positive Monocytes in Mice", *The Journal of Biological Chemistry*, vol. 278(47), pp. 46654-46660, Nov. 2003.

Targan, et al., "A Short-Term Study of Chimeric Monoclonal Antibody cA2 To Tumor Necrosis Factor α for Crohn's Disease", *N. Engl. J. Med.*, vol. 337(15), pp. 1029-1035, 1997.

Taylor, et al., "Reduction of Chemokine Levels and Leukocyte Traffic to Joints by Tumor Necrosis Factor α Blockade in Patients with Rheumatoid Arthritis", *Arthritis & Rheumatism*, vol. 43(1), pp. 38-47, Jan. 2000.

Tedder et al., "Structure-based design, synthesis, and antimicrobial activity of purine derived SAH/MTA nucleosidase inhibitors", *Bioorganic & Medicinal Chemistry Letters* 14, pp. 3165-3168, 2004.

Trentham, et al., "Autoimmunity to Type II Collagen: An Experimental Model of Arthritis," *J. Exp. Med.*, vol. 146, pp. 857-868 (1977).

Tucci, et al., "Synovial Tissues Collected from Rheumatoid Patients Undergoing Total Joint Arthroplasty Express Markers for Acute Inflammation", *Biomedical Sciences Instrumentation*, vol. 34, pp. 169-174, 1997.

Uehara, et al., "A Role for CCR9 in T Lymphocyte Development and Migration", *J. Immunol*, 168(6), pp. 2811-2819, 2002.

Ueno, et al., "Significance of Macrophase Chemoattractant Protein-1 in Macrophage Recruitment, Angiogenesis, and Survival in Human Breast Cancer", *Clinical Cancer Research*, vol. 6, pp. 3282-3289, Aug. 2000.

Vande Broek, et al., "Chemokine receptor CCR2 is expressed by human multiple myeloma cells and mediates migration to bone marrow stromal cell-produced monocyte chemotactic proteins MCP-1, -2 and -3", *British Journal of Cancer*, 88, pp. 855-862, 2003.

VanRiper, et al., "Characterization and Species Distribution of High Affinity GTP-coupled Receptors for Human Rantes and Monocyte Chemoattractant Protein 1", *J. Exp. Med.*, vol. 177, pp. 851-856, Mar. 1993.

Vervoordeldonk, et al., "Cytokines in Rheumatoid Arthritis", *Current Rheumatology Reports*, 4, pp. 208-217, 2002.

Vestergaard, et al., "Expression of CCR2 on Monocytes and Macrophages in Chronically Inflamed Skin in Atopic Dermatitis and Psoriasis", *Acta Derm Venereol*, 84, pp. 353-358, 2004.

Villiger, et al., "Production of Monocyte Chemoattractant Protein-1 by Inflamed Synovial Tissue and Cultured Synoviocytes", *The Journal of Immunology*, vol. 149(2), pp. 722-727, Jul. 1992.

Weisberg, et al., "CCR2 modulates inflammatory and metabolic effects of high-fat feeding", *The Journal of Clinical Investigation*, vol. 116(1), pp. 115-124, Jan. 2006.

Weisberg, et al., "Obesity is associated with macrophage accumulation in adipose tissue", *The Journal of Clinical Investigation*, vol. 112(12), pp. 1796-1808, Dec. 2003.

Wurbel, et al., "Mice lacking the CCR9 CC-chemokine receptor show a mile impairment of early T-and B-cell development and a reduction in T-cell receptor y +", *Blood*, vol. 98(9), pp. 2626-2632, Nov. 2001.

Xu, et al., "Chronic inflammation in fat plays a crucial role in the development of obesity-related insulin resistance", *The Journal of Clinical Investigation*, vol. 112(12), pp. 1821-1830, Dec. 2003.

Yang, et al., "Phenotypic Charact6eristics of infiltrated inflammatory cells, renal tubular epithelial cells and interstitial cells and their possible roles in the outcome of human drug-associated interstitial nephritis", National Medical Journal of China, vol. 81(2), pp. 73-77, Jan. 2001.

Yogi, et al., "Synthesis of imido-substituted 3,8-diphenyl-1,2-diazacycloocta-2,4,6,8-tetraenes and their thermolysis," *Bull. Chem. Soc. Jpn.*, vol. 60, pp. 731-735 (1987).

Yoshimatsu, et al., "Mechanism of action of E7010, an orally active sulfonamide antitumor agent: Inhibition of mitosis by binding to the colchicines site of tubulin," *Cancer Research*, vol. 57 (15), pp. 3208-3213 (1997).

Yoshino, et al., "Novel Sulfonamides as Potential, Systemically Active Antitumor Agents", *J. Med. Chem.*, vol. 35, 1992, pp. 2496-2497.

Youn, et al., "Role of the CC Chemokine receptor 9/TECK interaction in apoptosis", *Apoptosis*, vol. 7(3), pp. 271-276, 2002.

Zaballos, et al., Cutting Edge: Identification of the Orphan Chemokine Receptor CPR-9-6 as CCR9, the Receptor for the Chemokine TECK, *J. Immunol.*, 162, pp. 5671-5675, 1999.

\* cited by examiner

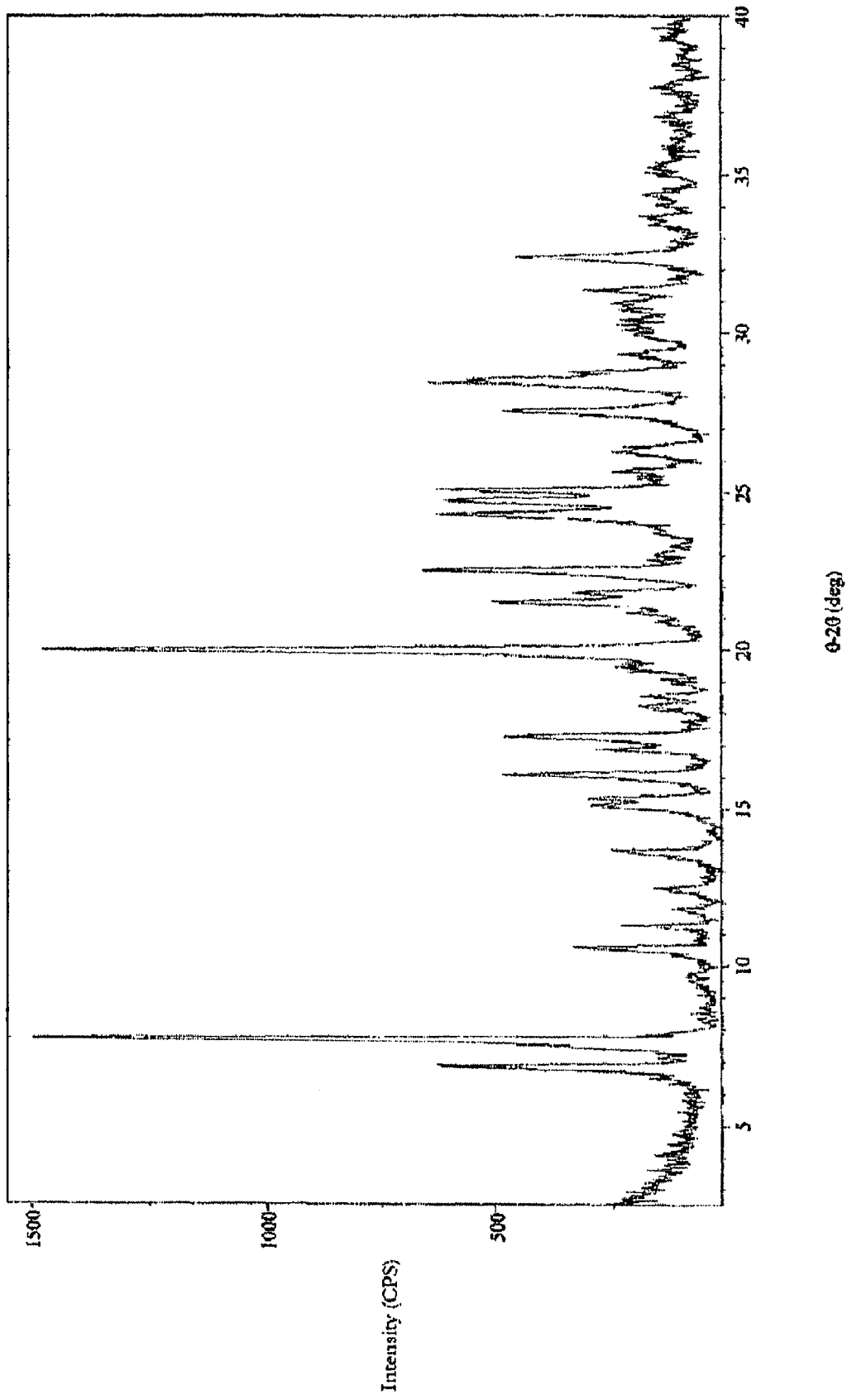

FUSED HETEROARYL PYRIDYL AND PHENYL BENZENESUFLONAMIDES AS CCR2 MODULATORS FOR THE TREATMENT OF INFLAMMATION

CROSS-REFERENCE TO RELATED APPLICATION

This application is a continuation of U.S. Ser. No. 12/171,782, filed Jul. 11, 2008, now U.S. Pat. No. 7,884,110 which application claims priority to U.S. provisional application Ser. No. 60/949,328, filed Jul. 12, 2007. The disclosures of these priority applications are incorporated by reference herein in their entirety.

FEDERALLY SPONSORED RESEARCH OR DEVELOPMENT

The present invention described herein was supported at least in part by NIH (U19-AI056690-01). The government has certain rights in the invention.

BACKGROUND

The present invention provides compounds, pharmaceutical compositions containing one or more of those compounds or their pharmaceutically acceptable salts, which are effective in inhibiting the binding or function of various chemokines to chemokine receptors. As antagonists or modulators of chemokine receptors, the compounds and compositions have utility in treating various immune disorder conditions and diseases.

Chemokines, also known as chemotactic cytokines, are a group of small molecular-weight proteins that are released by a wide variety of cells and have a variety of biological activities. Chemokines attract various types of cells of the immune system, such as macrophages, T cells, eosinophils, basophils and neutrophils, and cause them to migrate from the blood to various lymphoid and none-lymphoid tissues. They mediate infiltration of inflammatory cells to sites of inflammation, and are responsible for the initiation and perpetration of many inflammation diseases (reviewed in Schall, Cytokine, 3:165-183 (1991), Schall et al., Curr. Opin. Immunol., 6:865-873 (1994)).

In addition to stimulating chemotaxis, chemokines can induce other changes in responsive cells, including changes in cell shape, granule exocytosis, integrin up-regulation, formation of bioactive lipids (e.g., leukotrienes), respiratory burst associated with leukocyte activation, cell proliferation, resistance to induction of apoptosis and angiogenesis. Thus, chemokines are early triggers of the inflammatory response, causing inflammatory mediator release, chemotaxis and extravasation to sites of infection or inflammation. They are also stimulators of a multitude of cellular processes that bear important physiological functions as well as pathological consequences.

Chemokines exert their effects by activating chemokine receptors expressed by responsive cells. Chemokine receptors are a class of G-protein coupled receptors, also known as seven-transmembrane receptors, found on the surface of a wide variety of cell types such as leukocytes, endothelial cells, smooth muscle cells and tumor cells.

Chemokines and chemokine receptors are expressed by intrinsic renal cells and infiltrating cells during renal inflammation (Segerer et al., J. Am. Soc. Nephrol., 11:152-76 (2000); Morii et al., J. Diabetes Complications, 17:11-5 (2003); Lloyd et al. J. Exp. Med., 185:1371-80 (1997); Gonzalez-Cuadrado et al. Clin. Exp. Immunol,. 106:518-22 (1996); Eddy & Giachelli, Kidney Int., 47:1546-57 (1995); Diamond et al., Am. J. Physiol., 266:F926-33 (1994)). In humans, CCR2 and ligand MCP-1 are among the proteins expressed in renal fibrosis, and are correlated with the extent of macrophage infiltration into the interstitium (Yang et al., Zhonghua Yi Xue Za Zhi, 81:73-7 (2001); Stephan et al., J. Urol., 167:1497-502 (2002); Amann et al., Diabetes Care, 26:2421-5 (2003); Dai et al., Chin. Med. J. (Engl), 114:864-8 (2001)). In animal models of renal fibrosis, blockade of CCR2 or MCP-1 leads to a marked reduction in severity of renal inflammation (Kitagawa et al., Am. J. Pathol., 165:237-46 (2004); Wada et al., Am. J. Pathol., 165:237-46 (2004); Shimizu et al., J. Am. Soc. Nephrol., 14:1496-505 (2003)).

Rheumatoid arthritis is a chronic disease of the joints characterized by synovial inflammation that leads to the destruction of cartilage and bone. Although the underlying causes of the disease are unknown, it is believed that macrophages and Th-1 type T cells play a key role in the initiation and perpetration of the chronic inflammatory process (Vervoordeldonk et al., Curr. Rheumatol. Rep., 4:208-17 (2002)).

MCP-1 is among the several chemokines, including MIP-1α and IL-8, identified in rheumatoid synovium (Villiger et al., J. Immunol., 149:722-7 (1992); Scaife et al., Rheumatology (Oxford), 43:1346-52 (2004); Shadidi et al., Scand. J. Immunol., 57:192-8 (2003); Taylor et al., Arthritis Rheum., 43:38-47 (2000); Tucci et al., Biomed. Sci. Instrum., 34:169-74 (1997)). Chemokine receptors CCR1, CCR2, CCR3 and CCR5 are up-regulated in the joints from arthritic mice (Plater-Zyberk et al., Immunol. Lett., 57:117-20 (1997). Blockade of MCP-1 activity using a CCR2 antagonist or an antibody against MCP-1 have been shown efficacious in reducing joint inflammation in experimental models of rheumatoid arthritis (Gong et al., J. Exp. Med., 186:131-7 (1997); Ogata et al., J. Pathol., 182:106-14 (1997)).

Chemokine receptor-mediated infiltration of macrophages in the fat tissues may also contribute to the complications arising from obesity, a condition resulting from excessive storage of fat in the body. Obesity predisposes the affected individuals to many disorders, such as non-insulin-dependent diabetes, hypertension, stroke, and coronary artery disease. In obesity, adipose tissues have altered metabolic and endocrine functions that lead to an increased release of fatty acids, hormones, and pro-inflammatory molecules. Adipose tissue macrophages are believed to be a key source of pro-inflammatory cytokines including TNF-alpha, iNOS and IL-6 (Weisberg et al., J. Clin. Invest., 112:1796-808 (2003)). Recruitment of macrophages to the adipose tissue is likely mediated by MCP-1 produced by adipocytes (Christiansen T, et al., Int J Obes (Lond). 2005 January; 29(1):146-50; Sartipy et al., Proc. Natl. Acad. Sci. U.S.A., 100:7265-70 (2003)).

Elevated MCP-1 may induce adipocyte differentiation and insulin resistance, and contribute to pathologies associated with hyper-insulinemia and obesity. MCP-1 is over-expressed in plasma in obese mice compared to lean controls and white adipose is a major source. MCP-1 has also been shown to accelerate wound healing, and has a direct angiogenic effect on epithelial cells, and may play a direct role in the remodeling of adipose tissue in obesity. (Sartipy P, Loskutoff D J., Proc. Natl. Acad. Sci. U.S.A., 100:7265 (2003)).

MCP-1 plasma levels are substantially increased in Diet Induce Obesity (DIO) mice, and a strong correlation between plasma MCP-1 levels and body weight has been identified. Furthermore, elevation of MCP-1 induced by high fat diet causes changes in the CD11b positive monocyte population in DIO mice. (Takahashi K, et al., J. Biol. Chem., 46654 (2003)).

Furthermore, chronic inflammation in fat is thought to play a crucial role in the development of obesity-related insulin resistance (Xu H, et al., J Clin Invest. 2003 December; 112 (12):1821-30). It has been proposed that obesity related insulin resistance is, at least in part, a chronic inflammatory disease initiated in adipose tissue. Many inflammation and macrophage specific genes are dramatically upregulated in white adipose tissue in mouse models of genetic and high fat diet-induced obesity (DIO), and this upregulation precedes a dramatic increase in circulating insulin.

Increased expression levels of monocyte CCR2 and monocyte chemoattractant protein-1 in patients with diabetes mellitus (Biochemical and Biophysical Research Communications, 344(3):780-5 (2006)) were found in a study involving diabetic patients. Serum MCP-1 concentrations and surface expression of CCR2 on monocytes in diabetic patients were significantly higher than in non-diabetics, and the serum MCP-1 levels correlated with HbA1c, triglycerides, BMI, hs-CRP. Surface expression levels of CD36 and CD68 on monocytes were significantly increased in diabetic patients and more unregulated by MCP-1 in diabetics, augmenting uptake of ox-LDL, and hence potentially foam cell transformation. Elevated serum MCP-1 and increased monocyte CCR2, CD36, CD68 expression correlated with poor blood glucose control and potentially correlate with increased vessel wall monocyte recruitment.

MCP-1 is a potential player in negative cross talk between adipose tissue and skeletal muscle (Bianco J J, et al., Endocrinology, 2458 (2006)). MCP-1 can significantly reduce insulin-stimulated glucose uptake, and is a prominent inducer of insulin resistance in human skeletal muscle cell. Adipose tissue is a major secretory and endocrine active organ producing bioactive proteins regulating energy metabolism and insulin sensitivity.

CCR2 modulates inflammatory and metabolic effects of high-fat feeding (Weisberg S P, et al., J. Clin. Invest., 115 (2006)). Genetic deficiency in CCR2 reduced food intake and attenuated the development of obesity in mice fed a high fat diet. In obese mice matched for adiposity, CCR2 deficiency reduced macrophage content and inflammatory profile of adipose tissue, increased adiponectin expression, and improved glucose homeostatis and insulin sensitivity. In lean animals, no effect of CCR2 genotype on metabolic trait was found. In high-fat diet mice, CCR2 genotype modulated feeding, the development of obesity and adipose tissue inflammation. Once established, short term antagonism was shown to attenuate macrophage accumulation in adipose tissue and insulin resistance.

Chemokine and chemokine receptors are the key regulators of immune cell trafficking. MCP-1 is a potent chemoattractant of monocytes and T cells; its expression is induced under inflammatory conditions including proinflammatory cytokine stimulations and hypoxia. The interaction between MCP-1 and CCR2 mediates migration of monocytes, macrophage as well as activated T cells and play a key role in the pathogenesis of many inflammatory diseases. Inhibition of CCR2 functions using small molecule antagonists described in this invention represents a new approach for the treatments of inflammatory disorders.

Psoriasis is a chronic inflammatory disease characterized by hyperproliferation of keratinocytes and pronounced leukocyte infiltration. It is known that keratinocytes from psoriasis lesion express abundant CCR2 ligand MCP-1, particularly when stimulated by proinflammatory cytokines such as TNF-α (Vestergaard et al., Acta. Derm. Venereol., 84(5): 353-8 (2004); Gillitzer et al., J. Invest. Dermatol., 101(2): 127-31 (1993); Deleuran et al., J. Dermatol. Sci., 13(3):228- 36 (1996)). Since MCP-1 can attract migration of both macrophages and dendritic cells expressing CCR2 to the skin, this receptor and ligand pair is believed to be important in regulating the interaction between proliferating keratinocytes and dermal macrophage during the development of psoriasis. A small molecule antagonist may thus be useful in the treatment of psoriasis.

In addition to inflammatory diseases, chemokines and chemokine receptors have also been implicated in cancers (Broek et al., Br. J. Cancer, 88(6):855-62 (2003)). Tumor cells stimulate the formation of stroma that secretes various mediators pivotal for tumor growth, including growth factors, cytokines, and proteases. It is known that the level of MCP-1 is associated significantly with tumor-associated macrophage accumulation, and prognostic analysis reveals that high expression of MCP-1 is a significant indicator of early relapse in breast cancer (Ueno et al., Clin. Cancer Res., 6(8):3282-9 (2001)). A small molecule antagonist of a chemokine may thus be able to reduce the release of growth-stimulating cytokines by blocking accumulation of macrophages at sites of tumor formation.

U.S. Pat. No. 6,939,885 (ChemoCentryx, Inc.) discloses compounds useful in modulating CCR9 chemokine activity of the formula

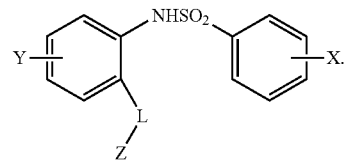

PCT Published Application WO 2003/099773 (Millennium Pharmaceuticals, Inc.) discloses compounds which can bind to CCR9 receptors of the formula

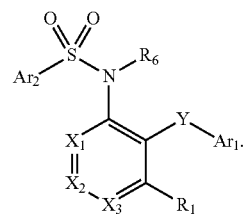

PCT Published Application WO 2005/004810 (Merck & Co., Inc.) discloses brandykinin B1 antagonists or inverse agonists of the formula

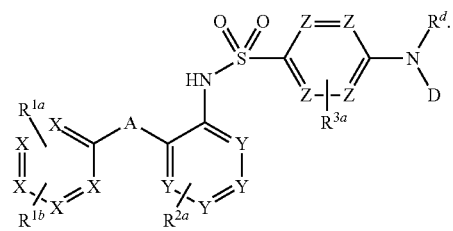

US Published Patent Application 2007/0037794 A1 (ChemoCentryx, Inc.) discloses CCR2 modulators, including the following compound:

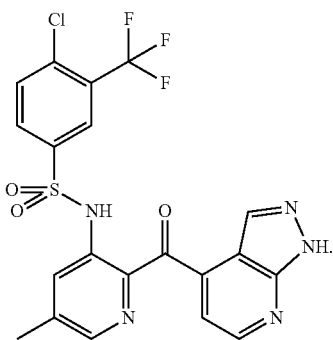 [SMILES: Cc1cnc(C(=O)c2ccnc3[nH]ncc23)c(NS(=O)(=O)c2ccc(Cl)c(C(F)(F)F)c2)c1]

Unfortunately, the above compound undergoes rapid elimination in vivo. Such drugs often require multiple administrations of the drug to achieve therapeutically effective blood levels over a significant period of time. Other methods are also available including sustained release formulations and devices.

BRIEF SUMMARY

The present invention is directed to compounds and pharmaceutically acceptable salts thereof, compositions, and methods useful in modulating chemokine activity. The compounds and salts thereof, compositions, and methods described herein are useful in treating or preventing chemokine-mediated conditions or diseases, including certain inflammatory and immunoregulatory disorders and diseases.

The compounds of the present invention have been shown to modulate one or more of CCR2, CCR3, CCR4, CCR5, CCR6, CCR7, CCR8, CCR9, CCR10, CXCR3, CXCR4, CXCR5, and CX3CR1. In particular, various compounds of the present invention modulate CCR2 as shown in the examples.

In certain embodiments, the present invention relates to a compound of the formula (I) or a salt thereof:

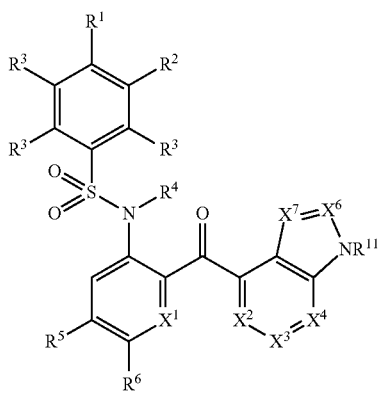

where:

$R^1$ and $R^2$ are each independently hydrogen, halogen, $C_{1-8}$ alkyl, —CN, or $C_{1-8}$ haloalkyl, provided that at least one of $R^1$ or $R^2$ is other than hydrogen;

each $R^3$ is independently hydrogen;

$R^4$ is hydrogen;

$R^5$ is halogen or $C_{1-8}$ alkyl;

$R^6$ is hydrogen;

$X^1$ is $CR^7$, N or NO;

$X^2$ and $X^4$ are N or NO;

$X^3$ is $CR^7$;

$X^6$ and $X^7$ are each independently selected from $CR^7$, N, and NO;

each $R^7$ is independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, —CN, =O, —NO$_2$, —OR$^8$, —OC(O)R$^8$, —CO$_2$R$^8$, —C(O)R$^8$, —C(O)NR$^9$R$^8$, —OC(O)NR$^9$R$^8$, —NR$^{10}$C(O)R$^8$, —NR$^{10}$C(O)NR$^9$R$^8$, —NR$^9$R$^8$, —NR$^{10}$CO$_2$R$^8$, —SR$^8$, —S(O)R$^8$, —S(O)$_2$R$^8$, —S(O)$_2$NR$^9$R$^8$, —NR$^{10}$S(O)$_2$R$^8$, substituted or unsubstituted $C_{6-10}$ aryl, substituted or unsubstituted 5- to 10-membered heteroaryl and substituted or unsubstituted 3- to 10-membered heterocyclyl;

each occurrence of $R^8$, $R^9$, and $R^{10}$ is independently selected from the group consisting of hydrogen, $C_{1-8}$ alkyl, $C_{2-8}$ alkenyl, $C_{2-8}$ alkynyl, aryl, or heteroaryl; or $R^9$ and $R^8$ or $R^{10}$ and $R^8$, together with the atom(s) to which they are attached, form an substituted or unsubstituted 5-, 6-, or 7-membered ring;

$R^{11}$ is selected from the group consisting of hydrogen, $C_{1-8}$ alkyl, $C_{2-8}$ alkenyl, $C_{2-8}$ alkynyl, substituted or unsubstituted $C_{6-10}$ aryl, substituted or unsubstituted 5-to 10-membered heteroaryl and substituted or unsubstituted 3- to 10-membered heterocycle.

In particular embodiments of compounds or salts of formula I, are compounds or salts thereof of a compound of formula (II):

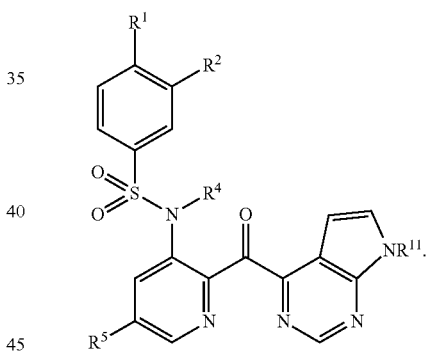

In certain embodiments, for compounds of formula I, each $R^3$ and $R^4$ and $R^6$ are hydrogen.

In certain embodiments, for compounds of formula I, $X^1$ is N.

In certain embodiments, for compounds of formula I, $X^2$ and $X^4$ are N, and $X^6$ and $X^7$ are $CR^7$.

In certain embodiments, for compounds of formula I, $R^1$ is Cl.

In certain embodiments, for compounds of formula I, $R^2$ is —CF$_3$.

In certain embodiments, for compounds of formula I, $R^4$ is H.

In certain embodiments, for compounds of formula I, $R^5$ is Cl or methyl.

In certain embodiments, for compounds of formula I, $R^5$ is methyl.

In certain embodiments, for compounds of formula I, $R^1$ is Cl, $R^2$ is CF$_3$, each $R^3$ is H, $R^5$ is Cl, and $R^6$ is H.

In one particular aspect, the present invention relates to a compound selected from the group consisting of:
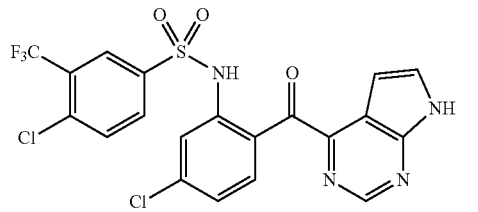
1
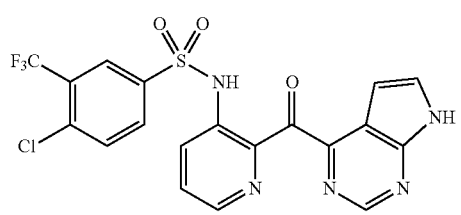
2
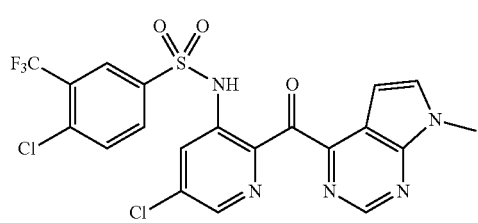
3
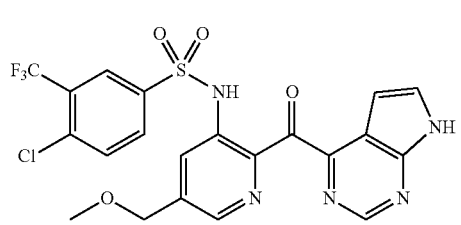
4
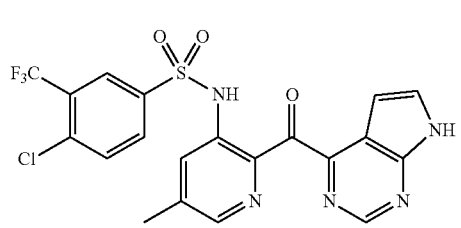
5
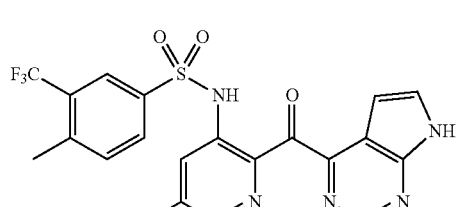
6
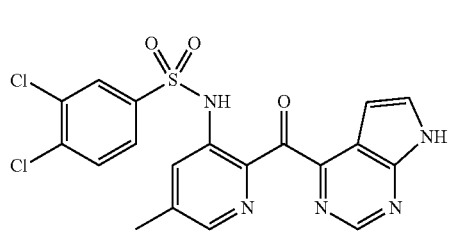
7
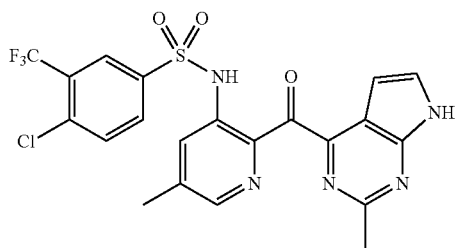
8
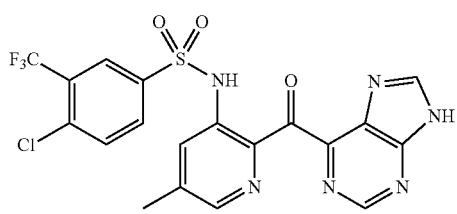
9
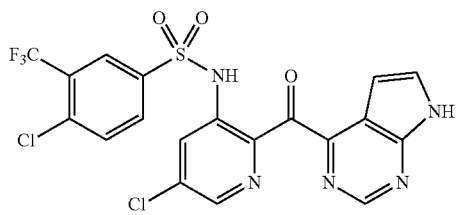
10
In another particular aspect, the present invention relates to a compound selected from the group consisting of:
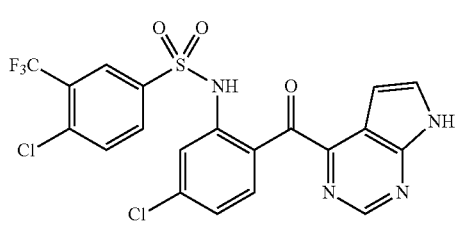
1
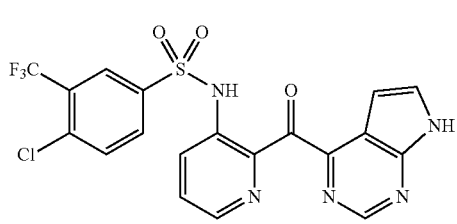
2
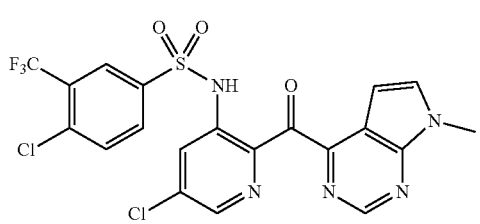
3

-continued

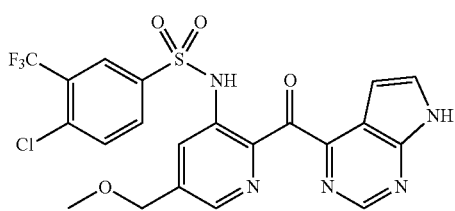
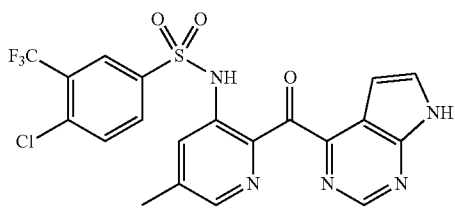
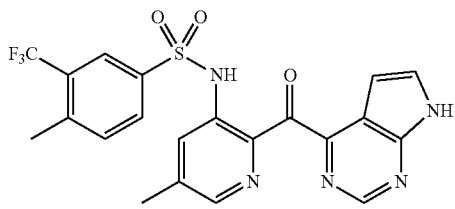
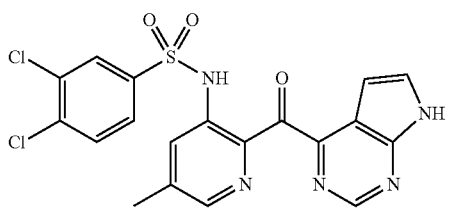
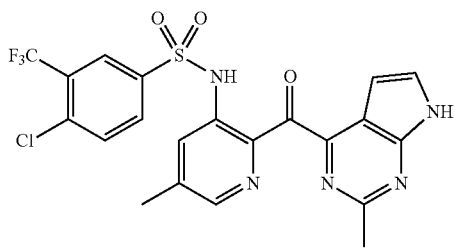
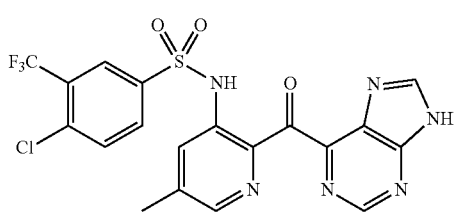
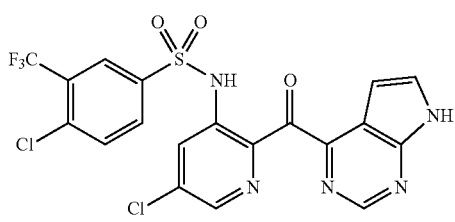

or a pharmaceutically acceptable salt thereof.

In one embodiment, the present compound may be represented by formula (I) or (III) or salts thereof:

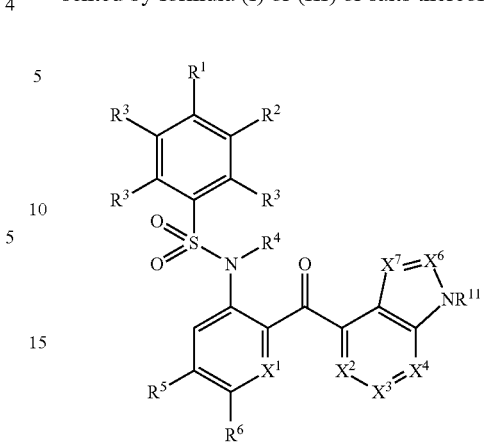

where $R^1$, $R^2$, $R^3$, $R^4$, $R^5$, $R^6$, $R^{11}$, $X^1$, $X^2$, $X^3$, $X^4$, $X^6$ and $X^7$ are as defined below.

In certain embodiments, the present invention relates to a compound of the formula (III) or a salt thereof:

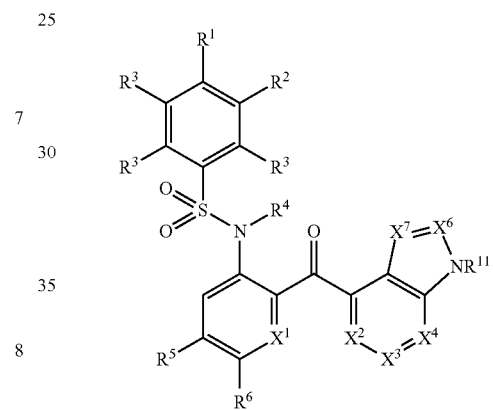

where:
$R^1$ and $R^2$ are each independently hydrogen, halogen, $C_{1-8}$ alkyl, —CN, or $C_{1-8}$ haloalkyl, provided that at least one of $R^1$ or $R^2$ is other than hydrogen;
each $R^3$ is independently hydrogen, halogen, or $C_{1-4}$ alkyl;
$R^4$ is hydrogen or $C_{1-8}$ alkyl;
$R^5$ is halogen or $C_{1-8}$ alkyl;
$R^6$ is hydrogen or $C_{1-4}$ alkyl;
$X^1$ is $CR^7$, N or NO;
$X^3$ is N or NO;
$X^2$, $X^4$, $X^6$, and $X^7$ are each independently $CR^7$, where each $R^7$ is independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, —CN, =O, —NO$_2$, —OR$^8$, —OC(O)R$^8$, —CO$_2$R$^8$, —C(O)R$^8$, —C(O)NR$^9$R$^8$, —OC(O)NR$^9$R$^8$, —NR$^{10}$C(O)R$^8$, —NR$^{10}$C(O)NR$^9$R$^8$, —NR$^9$R$^8$, —NR$^{10}$CO$_2$R$^8$, —SR$^8$, —S(O)R$^8$, —S(O)$_2$R$^8$, —S(O)$_2$NR$^9$R$^8$, —NR$^{10}$S(O)$_2$R$^8$, substituted or unsubstituted $C_{6-10}$ aryl, substituted or unsubstituted 5- to 10-membered heteroaryl and substituted or unsubstituted 3- to 10-membered heterocyclyl;
each occurrence of $R^8$, $R^9$, and $R^{10}$ is independently selected from the group consisting of hydrogen, $C_{1-8}$ alkyl, $C_{2-8}$ alkenyl, $C_{2-8}$ alkynyl, aryl, or heteroaryl; or $R^9$ and $R^8$ or $R^{10}$ and $R^8$, together with the atom(s) to which they are attached, form an substituted or unsubstituted 5-, 6-, or 7-membered ring;
$X^5$ is O, S, or NR$^{11}$, where $R^{11}$ is selected from the group consisting of hydrogen, $C_{1-8}$ alkyl, $C_{2-8}$ alkenyl, $C_{2-8}$ alkynyl, substituted or unsubstituted $C_{6-10}$ aryl, substituted or unsubstituted 5-to 10-membered heteroaryl and substituted or unsubstituted 3- to 10-membered heterocycle.

In one particular embodiment, a compound of formula III has the formula (IV):

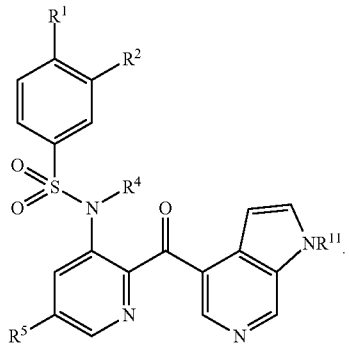

In another aspect, the present invention provides compositions useful in modulating chemokine activity. In one embodiment, a composition according to the present invention comprises a compound according to the invention and a pharmaceutically acceptable carrier or excipient.

In yet another aspect, the present invention provides a method of modulating chemokine function in a cell, comprising contacting the cell with a therapeutically effective amount of a compound or composition according to the invention.

In still another aspect, the present invention provides a method for modulating chemokine function, comprising contacting a chemokine receptor with a therapeutically effective amount of a compound or composition according to the invention.

In still another aspect, the present invention provides a method for treating a chemokine-mediated condition or disease, comprising administering to a subject a safe and effective amount of a compound or composition according to the invention.

In one particular aspect, the present invention relates to a method of treating a CCR2-mediated condition or disease comprising administering to a subject a therapeutically effective amount of a compound or pharmaceutically acceptable salt of a compound of formula I. In certain embodiments, a CCR2-mediated condition or disease is atherosclerosis. In certain embodiments, a CCR2-mediated condition or disease is restenosis. In certain embodiments, a CCR2-mediated condition or disease is multiple sclerosis. In certain embodiments, a CCR2-mediated condition or disease is selected from the group consisting of inflammatory bowel disease, renal fibrosis, rheumatoid arthritis, obesity and noninsulin-dependent diabetes. In certain embodiments, a CCR2-mediated condition or disease is type 2 diabetes. In certain embodiments, a CCR2-mediated condition or disease is selected from the group consisting of chronic obstructive pulmonary disease, idiopathic pulmonary fibrosis and idiopathic pneumonia syndrome.

In addition to the compounds provided herein, the present invention further provides pharmaceutical compositions containing one or more of these compounds, as well as methods for the use of these compounds in therapeutic methods, primarily to treat diseases associated with chemokine signaling activity.

In another aspect, the present invention provides for crystalline forms of 4-Chloro-N-[5-methyl-2-(7H-pyrrolo[2,3-d]pyrimidine-4-carbonyl)-pyridin-3-yl]-3-trifluoromethyl-benzenesulfonamide sodium salt. In certain embodiments, a crystalline form 4-Chloro-N-[5-methyl-2-(7H-pyrrolo[2,3-d]pyrimidine-4-carbonyl)-pyridin-3-yl]-3-trifluoromethyl-benzenesulfonamide sodium salt has an X-ray powder diffraction comprising the following 2-theta values ±0.2 measured using $CuK_\alpha$ radiation 6.9, 7.7, 20.0, 24.3, 24.7, and 25.1. In other embodiments, a crystalline form of claim 23, wherein said crystalline form has an X-ray powder diffraction comprising the following 2-theta values ±0.2 measured using $CuK_\alpha$ radiation: 6.9, 7.7, 10.6, 11.3, 11.8, 12.5, 13.7, 15.1, 15.3, 16.1, 16.9, 17.3, 18.2, 18.5, 19.5, 20.0, 21.6, 21.8, 22.6, 24.3, 24.7, 25.1, 25.6, 26.3, 27.5, 28.5, 28.8, 29.3, 31.4, and 32.4.

BRIEF DESCRIPTION OF THE DRAWING

FIG. 1 depicts a XPRD (x-ray powder diffraction) spectrum of 4-chloro-N-[5-methyl-2-(7H-pyrrolo[2,3-d]pyrimidine-4-carbonyl)-pyridin-3-yl]-3-trifluoromethyl-benzenesulfonamide sodium salt as described in Example 14.

DETAILED DESCRIPTION

General

The present invention is directed to compounds and salts thereof, compositions and methods useful in the modulation of chemokine receptor function, particularly CCR2 function. Modulation of chemokine receptor activity, as used herein in its various forms, is intended to encompass antagonism, agonism, partial antagonism, inverse agonism and/or partial agonism of the activity associated with a particular chemokine receptor, preferably the CCR2 receptor. Accordingly, the compounds of the present invention are compounds which modulate at least one function or characteristic of mammalian CCR2, for example, a human CCR2 protein. The ability of a compound to modulate the function of CCR2, can be demonstrated in a binding assay (e.g., ligand binding or agonist binding), a migration assay, a signaling assay (e.g., activation of a mammalian G protein, induction of rapid and transient increase in the concentration of cytosolic free calcium), and/or cellular response assay (e.g., stimulation of chemotaxis, exocytosis or inflammatory mediator release by leukocytes).

Abbreviations and Definitions

When describing the compounds, compositions, methods and processes of this invention, the following terms have the following meanings, unless otherwise indicated.

"Alkyl" by itself or as part of another substituent refers to a hydrocarbon group which may be linear, cyclic, or branched or a combination thereof having the number of carbon atoms designated (i.e., $C_{1-8}$ means one to eight carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. Alkyl groups can be substituted or unsubstituted, unless otherwise indicated. Examples of substituted alkyl include haloalkyl, thioalkyl, aminoalkyl, and the like.

"Alkoxy" refers to —O-alkyl. Examples of an alkoxy group include methoxy, ethoxy, n-propoxy etc.

"Alkenyl" refers to an unsaturated hydrocarbon group which may be linear, cyclic or branched or a combination thereof. Alkenyl groups with 2-8 carbon atoms are preferred. The alkenyl group may contain 1, 2 or 3 carbon-carbon double bonds. Examples of alkenyl groups include ethenyl, n-propenyl, isopropenyl, n-but-2-enyl, n-hex-3-enyl, cyclohexenyl, cyclopentenyl and the like. Alkenyl groups can be substituted or unsubstituted, unless otherwise indicated.

"Alkynyl" refers to an unsaturated hydrocarbon group which may be linear, cyclic or branched or a combination thereof. Alkynyl groups with 2-8 carbon atoms are preferred. The alkynyl group may contain 1, 2 or 3 carbon-carbon triple bonds. Examples of alkynyl groups include ethynyl, n-propynyl, n-but-2-ynyl, n-hex-3-ynyl and the like. Alkynyl groups can be substituted or unsubstituted, unless otherwise indicated.

"Aryl" refers to a polyunsaturated, aromatic hydrocarbon group having a single ring (monocyclic) or multiple rings (bicyclic), which can be fused together or linked covalently. Aryl groups with 6-10 carbon atoms are preferred, where this number of carbon atoms can be designated by $C_{6-10}$, for example. Examples of aryl groups include phenyl and naphthalene-1-yl, naphthalene-2-yl, biphenyl and the like. Aryl groups can be substituted or unsubstituted, unless otherwise indicated.

"Halo" or "halogen", by itself or as part of a substituent refers to a chlorine, bromine, iodine, or fluorine atom.

"Haloalkyl", as a substituted alkyl group, refers to a mono-haloalkyl or polyhaloalkyl group, most typically substituted with from 1-3 halogen atoms. Examples include 1-chloroethyl, 3-bromopropyl, trifluoromethyl and the like.

"Heterocyclyl" refers to a saturated or unsaturated non-aromatic ring containing at least one heteroatom (typically 1 to 5 heteroatoms) selected from nitrogen, oxygen or sulfur. The heterocyclyl ring may be monocyclic or bicyclic. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like. Preferred heterocyclic groups are monocyclic, though they may be fused or linked covalently to an aryl or heteroaryl ring system.

In one preferred embodiment, heterocyclic groups may be represented by formula (AA) below:

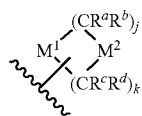

AA where formula (AA) is attached via a free valence on either $M^1$ or $M^2$; $M^1$ represents O, $NR^e$, or $S(O)_l$; $M^2$ represents $CR^fR^g$, O, $S(O)_l$, or $NR^e$; l is 0, 1 or 2; j is 1, 2 or 3 and k is 1, 2 or 3, with the proviso that j+k is 3, 4, or 5; and $R^a$, $R^b$, $R^c$, $R^d$, $R^e$, $R^f$, and $R^g$ are independently selected from the group consisting of hydrogen, halogen, unsubstituted or substituted $C_{1-8}$ alkyl, unsubstituted or substituted $C_{2-8}$ alkenyl, unsubstituted or substituted $C_{2-8}$ alkynyl, $-COR^h$, $-CO_2R^h$, $-CONR^hR^i$, $-NR^hCOR^i$, $-SO_2R^h$, $-SO_2NR^hR^i$, $-NSO_2R^hR^i$—$NR^hR^i$, $-OR^h$, $-Q^1COR^h$, $-Q^1CO_2R^h$, $-Q^1CONR^hR^i$, $-Q^1NR^hCOR^i$, $-Q^1SO_2R^{28}$, $-Q^1SO_2NR^hR^i$, $-Q^1NSO_2R^hR^i$, $-Q^1NR^hR^i$, $-Q^1OR^h$, wherein $Q^1$ is a member selected from the group consisting of $C_{1-4}$ alkylene, $C_{2-4}$ alkenylene and $C_{2-4}$ alkynylene, and $R^h$ and $R^i$ are independently selected from the group consisting of hydrogen and $C_{1-8}$ alkyl, and wherein the aliphatic portions of each of the $R^a$, $R^b$, $R^c$, $R^d$, $R^e$, $R^f$, $R^g$, $R^h$ and $R^i$ substituents are optionally substituted with from one to three members selected from the group consisting of halogen, $-OH$, $-OR^n$, $-OC(O)NHR^n$, $-OC(O)NR^nR^o$, $-SH$, $-SR^n$, $-S(O)R^n$, $-S(O)_2R^n$, $-SO_2NH_2$, $-S(O)_2NHR^n$, $-S(O)_2NR^nR^o$, $-NHS(O)_2R^n$, $-NR^nS(O)_2R^o$, $-C(O)NH_2$, $-C(O)NHR^n$, $-C(O)NR^nR^o$, $-C(O)R^n$, $-NHC(O)R^o$, $-NR^nC(O)R^o$, $-NHC(O)NH_2$, $-NR^nC(O)NH_2$, $-NR^nC(O)NHR^o$, $-NHC(O)NHR^n$, $-NR^nC(O)NR^oR^p$, $-NHC(O)NR^nR^o$, $-CO_2H$, $-CO_2R^n$, $-NHCO_2R^n$, $-NR^nCO_2R^o$, $-CN$, $-NO_2$, $-NH_2$, $-NHR^n$, $-NR^nR^o$, $-NR^nS(O)NH_2$ and $-NR^nS(O)_2NHR^o$, wherein $R^n$, $R^o$ and $R^p$ are independently an unsubstituted $C_{1-8}$ alkyl. Additionally, any two of $R^a$, $R^b$, $R^c$, $R^d$, $R^e$, $R^f$ and $R^g$ may be combined to form a bridged or spirocyclic ring system.

In one preferred embodiment, the number of $R^a+R^b+R^c+R^d$ groups that are other than hydrogen is 0, 1 or 2. In a more preferred embodiment, $R^a$, $R^b$, $R^c$, $R^d$, $R^e$, $R^f$, and $R^g$ are independently selected from the group consisting of hydrogen, halogen, unsubstituted or substituted $C_{1-8}$ alkyl, $-COR^h$, $-CO_2R^h$, $-CONR^hR^i$, $-NR^hCOR^h$, $-SO_2R^h$, $-SO_2NR^hR^i$, $-NSO_2R^hR^i$, $-NR^hR^i$, and $-OR^h$, wherein $R^h$ and $R^i$ are independently selected from the group consisting of hydrogen and unsubstituted $C_{1-8}$ alkyl and wherein the aliphatic portions of each of the $R^a$, $R^b$, $R^c$, $R^d$, $R^e$, $R^f$ and $R^g$ substituents are optionally substituted with from one to three members selected from the group consisting of halogen, $-OH$, $-OR^n$, $-OC(O)NHR^n$, $-OC(O)NR^nR^o$, $-SH$, $-SR^n$, $-S(O)R^o$, $-S(O)_2R^n$, $-SO_2NH_2$, $-S(O)_2NHR^n$, $-S(O)_2NR^nR^o$, $-NHS(O)_2R^n$, $-NR^nS(O)_2R^o$, $-C(O)NH_2$, $-C(O)NHR^n$, $-C(O)NR^nR^o$, $-C(O)R^n$, $-NHC(O)R^n$, $-NR^nC(O)R^o$, $-NHC(O)NH_2$, $-NR^nC(O)NH_2$, $-NR^nC(O)NHR^o$, $-NHC(O)NHR^n$, $-NR^nC(O)NR^oR^p$, $-NHC(O)NR^nR^o$, $-CO_2H$, $-CO_2R^n$, $-NHCO_2R^n$, $-NR^nCO_2R^o$, $-CN$, $-NO_2$, $-NH_2$, $-NHR^n$, $-NR^nR^o$, $-NR^nS(O)NH_2$ and $-NR^nS(O)_2NHR^o$, wherein $R^n$, $R^o$ and $R^p$ are independently an unsubstituted $C_{1-8}$ alkyl.

In a more preferred embodiment, $R^a$, $R^b$, $R^c$, $R^d$, $R^e$, $R^f$, and $R^g$ are independently hydrogen or $C_{1-4}$ alkyl. In another preferred embodiment, at least three of $R^a$, $R^b$, $R^c$, $R^d$, $R^e$, $R^f$, and $R^g$ are hydrogen.

"Heteroaryl" refers to an aromatic group containing at least one heteroatom, where the heteroaryl group may be monocyclic or bicyclic. Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, azaindolyl, azaindazolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl. Preferred heteroaryl groups are those having at least one aryl ring nitrogen atom, such as quinolinyl, quinoxalinyl, purinyl, benzimidazolyl, benzopyrazolyl, benzotriazolyl, benzothiazolyl, indolyl, quinolyl, isoquinolyl and the like. Preferred 6-ring heteroaryl systems include pyridyl, pyridazinyl, pyrazinyl, pyrimidinyl, triazinyl and the like. Preferred 5-ring heteroaryl systems include isothiazolyl, pyrazolyl, imidazolyl, thienyl, furyl, triazolyl, tetrazolyl, oxazolyl, isoxazolyl, oxadiazolyl, thiadiazolyl, pyrrolyl, thiazolyl and the like.

Heterocyclyl and heteroaryl can be attached at any available ring carbon or heteroatom. Each heterocyclyl and heteroaryl may have one or more rings. When multiple rings are present, they can be fused together or linked covalently. Each heterocyclyl and heteroaryl must contain at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Heterocyclyl and heteroaryl groups can be substituted or unsubstituted, unless otherwise indicated. For substituted groups, the substitution may be on a carbon or heteroatom. For example, when the substitution is oxo (=O or —O$^-$), the resulting group may have either a carbonyl (—C(O)—) or a N-oxide (—N$^+$—O$^-$).

Suitable substituents for substituted alkyl, substituted alkenyl, and substituted alkynyl include halogen, —CN, —CO$_2$R', —C(O)R', —C(O)NR'R", oxo (=O or —O$^-$), —OR', —OC(O)R', —OC(O)NR'R"—NO$_2$, —NR'C(O)R", —NR'''C(O)NR'R", —NR'R", —NR'CO$_2$R", —NR'S(O)R", —NR'S(O)$_2$R''', —NR'''S(O)NR'R", —NR'''S(O)$_2$NR'R", —SR', —S(O)R', —S(O)$_2$R', —S(O)$_2$NR'R", —NR'—C(NHR")=NR''', —SiR'R"R''', —N$_3$, substituted or unsubstituted C$_{6-10}$ aryl, substituted or unsubstituted 5- to 10-membered heteroaryl, and substituted or unsubstituted 3- to 10-membered heterocyclyl. The number of possible substituents range from zero to (2m'+1), where m' is the total number of carbon atoms in such radical.

Suitable substituents for substituted aryl, substituted heteroaryl and substituted heterocyclyl include halogen, —CN, —CO$_2$R', —C(O)R', —C(O)NR'R", oxo (=O or —O$^-$), —OR', —OC(O)R', —OC(O)NR'R", —NO$_2$, —NR'C(O)R", —NR'''C(O)NR'R", —NR'R", —NR'CO$_2$R", —NR'S(O)R", —NR'S(O)$_2$R", —NR'''S(O)NR'R", —NR'''S(O)$_2$NR'R", —SR', —S(O)R', —S(O)$_2$R', —S(O)$_2$NR'R", —NR'—C(NHR")=NR''', —SiR'R"R''', —N$_3$, substituted or unsubstituted C$_{1-8}$ alkyl, substituted or unsubstituted C$_{2-8}$ alkenyl, substituted or unsubstituted C$_{2-8}$ alkynyl, substituted or unsubstituted C$_{6-10}$ aryl, substituted or unsubstituted 5- to 10-membered heteroaryl, and substituted or unsubstituted 3- to 10 membered heterocyclyl. The number of possible substituents range from zero to the total number of open valences on the aromatic ring system.

As used above, R', R" and R''' each independently refer to a variety of groups including hydrogen, substituted or unsubstituted C$_{1-8}$ alkyl, substituted or unsubstituted C$_{2-8}$ alkenyl, substituted or unsubstituted C$_{2-8}$ alkynyl, substituted or unsubstituted aryl, substituted or unsubstituted heteroaryl, substituted or unsubstituted heterocyclyl, substituted or unsubstituted arylalkyl, substituted or unsubstituted aryloxyalkyl. When R' and R" are attached to the same nitrogen atom, they can be combined with the nitrogen atom to form a 3-, 4-, 5-, 6-, or 7-membered ring (for example, —NR'R" includes 1-pyrrolidinyl and 4-morpholinyl). Furthermore, R' and R", R" and R''', or R' and R''' may together with the atom(s) to which they are attached, form a substituted or unsubstituted 5-, 6- or 7-membered ring.

Two of the substituents on adjacent atoms of an aryl or heteroaryl ring may optionally be replaced with a substituent of the formula -T-C(O)—(CH$_2$)$_q$—U—, wherein T and U are independently —NR""—, —O—, —CH$_2$— or a single bond, and q is an integer of from 0 to 2. Alternatively, two of the substituents on adjacent atoms of the aryl or heteroaryl ring may optionally be replaced with a substituent of the formula -A'-(CH$_2$)$_r$—B'—, wherein A' and B' are independently —CH$_2$—, —O—, —NR""—, —S—, —S(O)—, —S(O)$_2$—, —S(O)$_2$NR""— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR""—, —S—, —S(O)—, —S(O)$_2$—, or —S(O)$_2$NR'—. R"" in is selected from hydrogen or unsubstituted C$_{1-8}$ alkyl.

"Heteroatom" is meant to include oxygen (O), nitrogen (N), sulfur (S) and silicon (Si).

"Pharmaceutically acceptable" carrier, diluent, or excipient is a carrier, diluent, or excipient compatible with the other ingredients of the formulation and not deleterious to the recipient thereof.

"Pharmaceutically-acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Salts derived from pharmaceutically-acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like.

Also included are salts of amino acids such as arginate and the like, and salts of organic acids like glucuronic or galactunoric acids and the like (see, for example, Berge, S. M. et al, "Pharmaceutical Salts", *J. Pharmaceutical Science,* 1977, 66:1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Salt thereof" refers to a compound formed when the hydrogen of an acid is replaced by a cation, such as a metal cation or an organic cation and the like. Preferably, the salt is a pharmaceutically-acceptable salt, although this is not required for salts of intermediate compounds which are not intended for administration to a patient.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs may be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation, selection, and use of prodrugs is discussed in T. Higuchi and V. Stella, "Pro-drugs as Novel Delivery Systems," Vol. 14 of the A.C.S. Symposium Series; "Design of Prodrugs", ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

The compounds of the invention may be present in the form of pharmaceutically acceptable metabolites thereof. The term "metabolite" means a pharmaceutically acceptable form of a metabolic derivative of a compound of the invention (or a salt thereof). In some aspects, the metabolite may be a functional derivative of a compound that is readily convertible in vivo into an active compound. In other aspects, the metabolite may be an active compound.

"Therapeutically effective amount" refers to an amount sufficient to effect treatment when administered to a patient in need of treatment.

"Treating" or "treatment" as used herein refers to the treating or treatment of a disease or medical condition (such as a viral, bacterial or fungal infection or other infectious diseases, as well as autoimmune or inflammatory conditions) in a patient, such as a mammal (particularly a human or a companion animal) which includes ameliorating the disease or medical condition, i.e., eliminating or causing regression of the disease or medical condition in a patient; suppressing the disease or medical condition, i.e., slowing or arresting the development of the disease or medical condition in a patient; or alleviating the symptoms of the disease or medical condition in a patient.

Certain compounds of the present invention can exist in unsolvated forms as well as solvated forms, including hydrated forms. In general, both solvated forms and unsolvated forms are intended to be encompassed within the scope of the present invention. Certain compounds of the present invention may exist in multiple crystalline or amorphous forms (i.e., as polymorphs). In general, all physical forms are equivalent for the uses contemplated by the present invention and are intended to be within the scope of the present invention.

It will be apparent to one skilled in the art that certain compounds of the present invention may exist in tautomeric forms, all such tautomeric forms of the compounds being within the scope of the invention. Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The compounds of the present invention may include a detectable label. A detectable label is a group that is detectable at low concentrations, usually less than micromolar, possibly less than nanomolar, and that can be readily distinguished from other molecules, due to differences in a molecular property (e. g. molecular weight, mass to charge ratio, radioactivity, redox potential, luminescence, fluorescence, electromagnetic properties, binding properties, and the like). Detectable labels may be detected by spectroscopic, photochemical, biochemical, immunochemical, electrical, magnetic, electromagnetic, optical or chemical means and the like.

A wide variety of detectable labels are within the scope of the present invention, including hapten labels (e.g. biotin, or labels used in conjunction with detectable antibodies such as horse radish peroxidase antibodies); mass tag labels (e.g. stable isotope labels); radioisotopic labels (including H$^3$, I125, S35, C14, or P32); metal chelate labels; luminescent labels including fluorescent labels (such as fluorescein, isothiocyanate, Texas red, rhodamine, green fluorescent protein, and the like), phosphorescent labels, and chemiluminescent labels, typically having quantum yield greater than 0.1; electroactive and electron transfer labels; enzyme modulator labels including coenzymes, organometallic catalysts horse radish peroxidase, alkaline phosphatase and others commonly used in an ELISA; photosensitizer labels; magnetic bead labels including Dynabeads; colorimetric labels such as colloidal gold, silver, selenium, or other metals and metal sol labels (see U.S. Pat. No. 5,120,643, which is herein incorporated by reference in its entirety for all purposes), or colored glass or plastic (e.g., polystyrene, polypropylene, latex, etc.) bead labels; and carbon black labels. Patents teaching the use of such detectable labels include U.S. Pat. Nos. 3,817,837; 3,850,752; 3,939,350; 3,996,345; 4,277,437; 4,275,149; 4,366,241; 6,312,914; 5,990,479; 6,207,392; 6,423,551; 6,251,303; 6,306,610; 6,322,901; 6,319,426; 6,326,144; and 6,444,143, which are herein incorporated by reference in their entirety for all purposes.

Detectable labels are commercially available or may be prepared as known to one skilled in the art. Detectable labels may be covalently attached to the compounds using a reactive functional group, which can be located at any appropriate position. Methods for attaching a detectable label are known to one skilled in the art. When the reactive group is attached to an alkyl, or substituted alkyl chain tethered to an aryl nucleus, the reactive group may be located at a terminal position of an alkyl chain.

Compounds

In certain embodiments, the compounds of the present invention are compounds, or salts thereof, represented by formula (I)

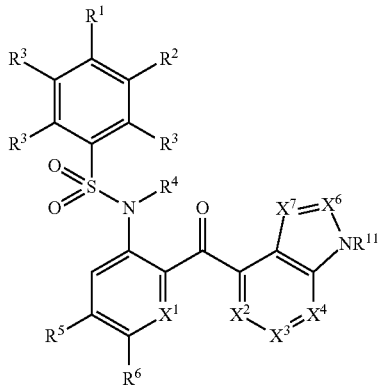

(I)

where $R^1$ and $R^2$ are each independently hydrogen, halogen, $C_{1-8}$ alkyl, —CN, or $C_{1-8}$ haloalkyl, provided that at least one of $R^1$ or $R^2$ is other than hydrogen;

each $R^3$ is independently hydrogen, halogen, or $C_{1-4}$ alkyl;

$R^4$ is hydrogen or $C_{1-8}$ alkyl;

$R^5$ is halogen or $C_{1-8}$ alkyl;

$R^6$ is hydrogen or $C_{1-4}$ alkyl;

$R^{11}$ is selected from the group consisting of hydrogen, $C_{1-8}$ alkyl, $C_{2-8}$ alkenyl, $C_{2-8}$ alkynyl, substituted or unsubstituted $C_{6-10}$ aryl, substituted or unsubstituted 5-to 10-membered heteroaryl and substituted or unsubstituted 3- to 10-membered heterocycle;

$X^1$ is $CR^7$, N or NO;

$X^2$ and $X^4$ are each independently N or NO;

$X^3$ is $CR^7$;

$X^6$, and $X^7$ are each independently selected from $CR^7$, N and NO;

each $R^7$ is independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, —CN, —NO$_2$, ⁻OR$^8$, —OC(O) R$^8$, —CO$_2$R$^8$, —C(O)R$^8$, —C(O)NR$^9$R$^8$, —OC(O)NR$^9$R$^8$, —NR$^{10}$C(O)R$^8$, —NR$^{10}$C(O)NR$^9$R$^8$, —NR$^9$R$^8$, —NR$^{10}$CO$_2$R$^8$, —SR$^8$, —S(O)R$^8$, —S(O)$_2$R$^8$, —S(O)$_2$NR$^9$R$^8$, —NR$^{10}$S(O)$_2$R$^8$, substituted or unsubstituted $C_{6-10}$ aryl, substituted or unsubstituted 5- to 10-membered heteroaryl and substituted or unsubstituted 3- to 10-membered heterocyclyl;

each occurrence of $R^8$, $R^9$, and $R^{10}$ is independently selected from the group consisting of hydrogen, $C_{1-8}$ alkyl, $C_{2-8}$ alkenyl, $C_{2-8}$ alkynyl, aryl, or heteroaryl; or $R^8$ and $R^9$ or $R^8$ and $R^{10}$, together with the atom(s) to which they are attached, form an substituted or unsubstituted 5-, 6-, or 7-membered ring.

Preferably, each $R^3$, $R^4$ and $R^6$ are each hydrogen.

In another embodiment, the compounds of the present invention are represented by formula (II), or salts thereof:

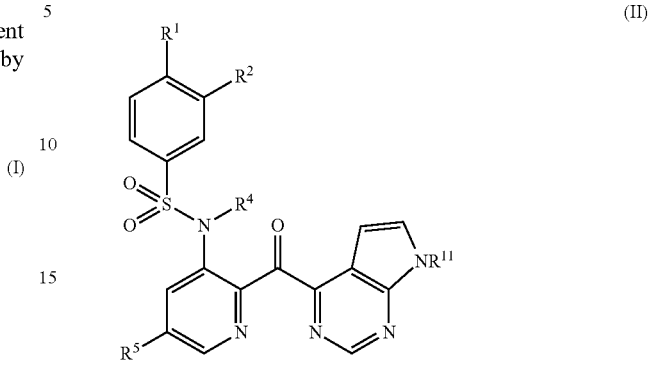

(II)

wherein $R^1$, $R^2$, $R^4$, $R^5$ and $R^{11}$ are as defined above for formula (I).

In another embodiment, the compounds of the present invention are represented by formula (III), or salts thereof:

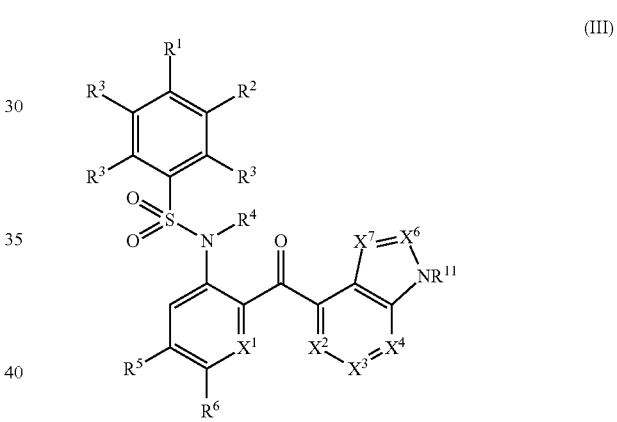

(III)

wherein $R^1$, $R^2$, $R^3$, $R^4$, $R^5$, $R^6$, and $R^{11}$ are as defined above for formula (I); and $X^1$ is $CR^7$, N or NO;

$X^3$ is N or NO;

$X^2$, $X^4$, $X^6$, and $X^7$ are each independently $CR^7$, where each $R^7$ is independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, —CN, =O, —NO$_2$, —OR$^8$, —OC(O)R$^8$, —CO$_2$R$^8$, —C(O)R$^8$, —C(O)NR$^9$R$^8$, —OC (O)NR$^9$R$^8$, —NR$^{10}$C(O)R$^8$, —NR$^{10}$C(O)NR$^9$R$^8$, —NR$^9$R$^8$, —NR$^{10}$CO$_2$R$^8$, —SR$^8$, —S(O)R$^8$, —S(O)$_2$R$^8$, —S(O)$_2$NR$^9$R$^8$, —NR$^{10}$S(O)$_2$R$^8$, substituted or unsubstituted $C_{6-10}$ aryl, substituted or unsubstituted 5- to 10-membered heteroaryl and substituted or unsubstituted 3- to 10-membered heterocyclyl;

each occurrence of $R^8$, $R^9$, and $R^{10}$ is independently selected from the group consisting of hydrogen, $C_{1-8}$ alkyl, $C_{2-8}$ alkenyl, $C_{2-8}$ alkynyl, aryl, or heteroaryl; or $R^9$ and $R^8$ or $R^{10}$ and $R^8$, together with the atom(s) to which they are attached, form an substituted or unsubstituted 5-, 6-, or 7-membered ring.

In another embodiment, the compounds of the present invention are represented by formula (IV), or salts thereof:

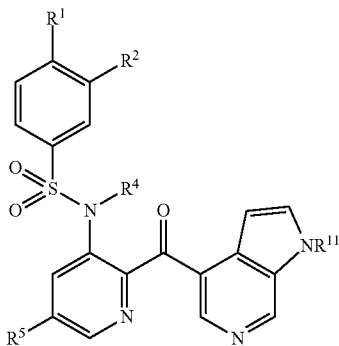

wherein $R^1$, $R^2$, $R^4$, $R^5$, and $R^{11}$ are as defined above for formula (III).

Preferred Embodiments

In any one of formula I, II, III, or IV, $R^1$ is halogen.
In any one of formula I, II, III, or IV, $R^2$ is $C_{1-8}$ haloalkyl.
In some embodiments of formula I, II, III, or IV, $R^1$ is Cl and $R^2$ is $CF_3$.
In some embodiments of formula I, II, III, or IV, $R^1$ is methyl and $R^2$ is $CF_3$.
In any one of formula I or III, $R^3$ is hydrogen.
In any one of formula I, II, III, or IV, $R^5$ is halogen.
In any one of formula I, II, III, or IV, $R^5$ is chlorine.
In any one of formula I, II, III, or IV, $R^5$ is $C_{1-8}$ alkyl.
In any one of formula I, II, III, or IV, $R^5$ is methyl.
In any one of formula I or III, $R^6$ is hydrogen.
In any one of formula I or III, $X^1$ is N.
In any one of formula I or III, $X^1$ is NO.
In any one of formula I or III, $X^1$ is $CR^7$.
In some embodiments of formula I or III, when $X^1$ is $CR^7$, $R^7$ is H.
In some embodiments of formula I, $X^2$ is N.
In some embodiments of formula I, $X^2$ is NO.
In some embodiments of formula I, $X^3$ is $CR^7$, where $R^7$ is H or $C_{1-4}$ alkyl.
In some embodiments of formula I, $X^4$ is N.
In some embodiments of formula I, $X^4$ is NO.
In some embodiments of formula III, $X^2$ is $CR^7$, where $R^7$ is H or $C_{1-4}$ alkoxy.
In some embodiments of formula III, $X^3$ is N.
In some embodiments of formula III, $X^3$ is NO.
In some embodiments of formula I, $X^4$ is $CR^7$, where $R^7$ is H or $C_{1-4}$ alkyl.
In some embodiments of formula I, II, III, or IV, $R^{11}$ is H or $C_{1-4}$ alkyl, most preferably H.
In some embodiments of formula I or III, $X^6$ is $CR^7$.
In some embodiments of formula I or III, $X^6$ is $CR^7$, where $R^7$ is H or $C_{1-4}$ alkyl, most preferably H.
In some embodiments of formula I or III, $X^6$ is N.
In some embodiments of formula I or III, $X^6$ is NO.
In some embodiments of formula I or III, $X^7$ is $CR^7$.
In some embodiments of formula I or III, $X^7$ is $CR^7$, where $R^7$ is H or $C_{1-4}$ alkyl, most preferably H.
In some embodiments of formula I or III, $X^7$ is N.
In some embodiments of formula I or III, $X^7$ is NO.

Compounds that Modulate CCR2 Activity

The present invention provides compounds that modulate at least one CCR2 activity. Chemokine receptors are integral membrane proteins which interact with an extracellular ligand, such as a chemokine, and mediate a cellular response to the ligand, e.g., chemotaxis, increased intracellular calcium ion concentration, etc. Therefore, modulation of a chemokine receptor function, e.g., interference with a chemokine receptor ligand interaction, will modulate a chemokine receptor mediated response, and treat or prevent a chemokine receptor mediated condition or disease. Modulation of a chemokine receptor function includes both inducement and inhibition of the function. The type of modulation accomplished will depend on the characteristics of the compound, i.e., antagonist or full, partial or inverse agonist.

Without intending to be bound by any particular theory, it is believed that the compounds provided herein interfere with the interaction between a chemokine receptor and one or more cognate ligands. In particular, it is believed that the compounds interfere with the interaction between CCR2 and a CCR2 ligand, such as MCP-1. Compounds contemplated by the invention include, but are not limited to, the exemplary compounds provided herein and salts thereof.

For example, compounds of this invention act as potent CCR2 antagonists, and this antagonistic activity has been further confirmed in animal testing for inflammation, one of the hallmark disease states for CCR2. Accordingly, the compounds provided herein are useful in pharmaceutical compositions, methods for the treatment of CCR2-mediated diseases, and as controls in assays for the identification of competitive CCR2 antagonists.

Compositions that Modulate Chemokine Activity

In another aspect, the present invention provides compositions that modulate chemokine activity, specifically CCR2 activity. Generally, the compositions for modulating chemokine receptor activity in humans and animals will comprise a pharmaceutically acceptable excipient or diluent and a compound having the formula provided above as formula (I).

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Pat. No. 6,451,339, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated enterically or otherwise by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil in water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative. and flavoring and coloring agents. Oral solutions can be prepared in combination with, for example, cyclodextrin, PEG and surfactants.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non toxic parenterally acceptable diluent or solvent, for example as a solution in 1,3-butane diol. Among the acceptable vehicles and solvents that may be employed are water, Ringer's solution and isotonic sodium chloride solution. In addition, sterile, axed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. Additionally, the compounds can be administered via ocular delivery by means of solutions or ointments. Still further, transdermal delivery of the subject compounds can be accomplished by means of iontophoretic patches and the like.

For topical use, creams, ointments, jellies, solutions or suspensions containing the compounds of the present invention are employed. As used herein, topical application is also meant to include the use of mouth washes and gargles.

The pharmaceutical compositions and methods of the present invention may further comprise other therapeutically active compounds as noted herein, such as those applied in the treatment of the above mentioned pathological conditions.

In one embodiment, the present invention provides a composition consisting of a pharmaceutically acceptable carrier and a compound of the invention.

Measuring Efficacy of Chemokine Modulators
In Vitro Assays

A variety of assays can be used to evaluate the compounds provided herein, including signaling assays, migration assays, ligand binding assays, and other assays of cellular response. Chemokine receptor signaling assays can be used to measure the ability of a compound, such as a potential CCR2 antagonist, to block CCR2 ligand- (e.g. MCP-1)-induced signaling. A migration assay can be used to measure the ability of a compound of interest, such as a possible chemokine antagonist, to block chemokine-mediated cell migration in vitro. The latter is believed to resemble chemokine-induced cell migration in vivo. A ligand binding assay can be used to measure the ability of a compound, such as a potential CCR2 antagonist, to block the interaction of MCP-1 with its receptor.

In a suitable assay, a chemokine protein (whether isolated or recombinant) is used which has at least one property, activity, or functional characteristic of a mammalian chemokine protein. The property can be a binding property (to, for example, a ligand or inhibitor), a signaling activity (e.g., activation of a mammalian G protein, induction of rapid and transient increase in the concentration of cytosolic free calcium ion), cellular response function (e.g., stimulation of chemotaxis or inflammatory mediator release by leukocytes), and the like.

The assay can be a cell-based assay that utilizes cells stably or transiently transfected with a vector or expression cassette having a nucleic acid sequence that encodes the chemokine receptor. Cell lines naturally expressing the chemokine can also be used. The cells are maintained under conditions appropriate for expression of the receptor and are contacted with a putative agent under conditions appropriate for binding to occur. Binding can be detected using standard techniques. For example, the extent of binding can be determined relative to a suitable control (for example, relative to background in the absence of a putative agent, or relative to a known ligand). Optionally, a cellular fraction, such as a membrane fraction, containing the receptor can be used in lieu of whole cells.

Detection of binding or complex formation can be detected directly or indirectly. For example, the putative agent can be labeled with a suitable label (e.g., fluorescent label, chemiluminescent label, isotope label, enzyme label, and the like) and binding can be determined by detection of the label. Specific and/or competitive binding can be assessed by competition or displacement studies, using unlabeled agent or a ligand (e.g., MCP-1) as a competitor.

Binding inhibition assays can be used to evaluate the present compounds. In these assays, the compounds are evaluated as inhibitors of ligand binding using, for example, MCP-1. In one embodiment, the CCR2 receptor is contacted with a ligand such as MCP-1 and a measure of ligand binding is made. The receptor is then contacted with a test agent in the presence of a ligand (e.g., MCP-1) and a second measurement of binding is made. A reduction in the extent of ligand binding is indicative of inhibition of binding by the test agent. The binding inhibition assays can be carried out using whole cells which express the chemokine, or a membrane fraction from cells which express the chemokine.

The binding of a G protein coupled receptor by, for example, an agonist, can result in a signaling event by the receptor. Accordingly, signaling assays can also be used to evaluate the compounds of the present invention and induction of signaling function by an agent can be monitored using any suitable method. For example, G protein activity, such as hydrolysis of GTP to GDP, or later signaling events triggered by receptor binding can be assayed by known methods (see, for example, PCT/US97/15915; Neote et al., *Cell*, 72:415425 (1993); Van Riper et al., *J. Exp. Med.*, 177:851-856 (1993) and Dahinden et al., *J. Exp. Med.*, 179:751-756 (1994)).

Chemotaxis assays can also be used to assess receptor function and evaluate the compounds provided herein. These assays are based on the functional migration of cells in vitro or in vivo induced by an agent, and can be used to assess the binding and/or effect on chemotaxis of ligands, inhibitors, or agonists. A variety of chemotaxis assays are known in the art, and any suitable assay can be used to evaluate the compounds of the present invention. Examples of suitable assays include those described in PCT/US97/15915; Springer et al., WO 94/20142; Berman et al., *Immunol. Invest.*, 17:625-677 (1988); and Kavanaugh et al., *J. Immunol.*, 146:4149-4156 (1991)).

Calcium signaling assays measure calcium concentration over time, preferably before and after receptor binding. These assays can be used to quantify the generation of a receptor-signaling mediator, $Ca^{++}$, following receptor binding (or absence thereof). These assays are useful in determining the ability of a compound, such as those of the present invention, to generate the receptor signaling mediator by binding to a receptor of interest. Also, these assays are useful in determining the ability of a compound, such as those of the present invention, to inhibit generation of the receptor signaling mediator by interfering with binding between a receptor of interest and a ligand.

In calcium signaling assays used to determine the ability of a compound to interfere with binding between a chemokine receptor and a known chemokine ligand, chemokine receptor-expressing cells (CCR2-expressing cells such as THP-1 cells) are first incubated with a compound of interest, such as a potential chemokine antagonist, at increasing concentrations. The cell number can be from $10^5$ to $5 \times 10^5$ cells per well in a 96-well microtiter plate. The concentration of the compound being tested may range from 0 to 100 μM. After a period of incubation (which can range from 5 to 60 minutes), the treated cells are placed in a Fluorometric Imaging Plate Reader (FLIPR®) (available from Molecular Devices Corp., Sunnyvale, Calif.) according to the manufacturer's instruction. The FLIPR® system is well known to those skilled in the art as a standard method of performing assays. The cells are then stimulated with an appropriate amount of the chemokine ligand (MCP-1 for CCR2) at 5-100 nM final concentration, and the signal of intracellular calcium increase (also called calcium flux) is recorded. The efficacy of a compound as an inhibitor of binding between the chemokine and the ligand can be calculated as an $IC_{50}$ (the concentration needed to cause 50% inhibition in signaling) or $IC_{90}$ (at 90% inhibition).

In vitro cell migration assays can be performed (but are not limited to this format) using the 96-well microchamber (called ChemoTX™). The ChemoTX™ system is well known to those skilled in the art as a type of chemotactic/cell migration instrument. In this assay, CCR2-expressing cells (such as THP-1) are first incubated with a compound of interest, such as a possible CCR2 antagonist, respectively, at increasing concentrations. Typically, fifty thousand cells per well are used, but the amount can range from $10^3$-$10^6$ cells per well. The chemokine ligand (for example, CCR2 ligand MCP-1, typically at 0.1 nM (but can range from 5-100 nM) is placed at the lower chamber and the migration apparatus is assembled. Twenty microliters of test compound-treated cells are then placed onto the membrane. Migration is allowed to take place at 37° C. for a period of time, typically 1.5 hours for CCR2. At the end of the incubation, the number of cells that migrated across the membrane into the lower chamber is then quantified. The efficacy of a compound as an inhibitor of chemokine-mediated cell migration is calculated as an $IC_{50}$ (the concentration needed to reduce cell migration by 50%) or $IC_{90}$ (for 90% inhibition).

BiRAM Assay

Examples of primary screens to identify chemokine antagonists include BiRAM assay (WO 02101350, US2004023286), which detects potential hits by their ability to activate cell migration under inhibitory chemokine concentration. To begin such an assay, chemokine expressing cells (such as THP-1 cells for CCR2 assay) are harvested by centrifugation of cell suspension at 1000 RPM on a GS-6R Beckman centrifuge. The cell pellet is resuspended in chemotaxis buffer (HBSS/0.1% BSA) at $10 \times 10^6$ cells/mL for CCR2 assay. Twenty-five microliters of cells are mixed with an equal volume of a test compound diluted to 20 μM in the same buffer. Twenty microliters of the mixture are transferred onto the filter in the upper chemotaxis chamber, with 29 μL of chemokine solution containing chemokine ligand (100 nM chemokine MCP-1 and MIP-1α protein for CCR2 assay) is placed in the lower chamber. Following an incubation at 37° C. (90-minute for CCR2), the assay is terminated by removing the cell drops from atop the filter. To quantify cells migrated across the membrane, 5 μL of 7× CyQUANT® solution is added to each well in the lower chamber, and the fluorescence signal measured on a Spectrafluor Plus fluorescence plate reader (TECAN, Durham, N.C.).

For selection of potential hits, the level of migration activation is calculated as a RAM index—the ratio between the signal of a particular well and the median signal of the whole plate. Compounds with a RAM index of greater than 1.5 for CCR2 assay are regarded as RAM positive, and are selected for $IC_{50}$ determinations in conventional functional assays.

Calcium Flux Assay

Calcium flux assay measures an increase in intracellular calcium following ligand-induced receptor activation and may be employed as a secondary assay following primary screening. Such an assay may be carried out, for instance, on a FLIPR® machine (Molecular Devices, Mountain View, Calif.). To begin an assay, chemokine expressing cells (such as THP-1 cells for CCR2 assay) are harvested by centrifugation of cell suspension, and resuspended to $1.5 \times 10^6$ cells/mL in HBSS (with 1% fetal calf serum). Cells are then labeled with a calcium indicator dye Fluo-4 AM for 45 minutes at 37° C. with gentle shaking. Following incubation, cells are pelleted, washed once with HBSS and resuspended in the same buffer at a density of $1.6 \times 10^6$ cells/mL. One hundred microliters of labeled cells are mixed with 10 μL of test compound at the appropriate concentrations on an assay plate. Chemokine protein (MCP-1 at a final concentration of 0.1 nM for CCR2 assay) is added to activate the receptor. The degree of inhibition is determined by comparing calcium signals between compound-treated and untreated cells. $IC_{50}$ calculations are further performed by non-linear squares regression analysis using Graphpad Prism (Graphpad Software, San Diego, Calif.).

Ligand Binding Assay

Ligand binding assay can be used to determine the ability of potential CCR2 antagonists to block the interaction between CCR2 and its ligand MCP-1. CCR2 expressing THP-1 cells are centrifuged and resuspended in assay buffer (20 mM HEPES pH 7.1, 140 mM NaCl, 1 mM $CaCl_2$, 5 mM $MgCl_2$, and with 0.2% bovine serum albumin) to a concentration of $2.2 \times 10^5$ cells/mL. Binding assays are set up as follows. First, 0.09 mL of cells ($1 \times 10^5$ THP-1 cells/well) was added to the assay plates containing the compounds, giving a final concentration of ~2-10 μM each compound for screening (or part of a dose response for compound $IC_{50}$ determinations). Then 0.09 mL of $^{125}I$ labeled MCP-1 (obtained from Amersham; Piscataway, N.J.) diluted in assay buffer to a final concentration of ~50 pM, yielding ~30,000 cpm per well, is added, the plates sealed and incubated for approximately 3 hours at 4° C. on a shaker platform. Reactions are aspirated onto GF/B glass filters pre-soaked in 0.3% polyethyleneimine (PEI) solution, on a vacuum cell harvester (Packard Instruments; Meriden, Conn.). Scintillation fluid (50 μL; Microscint 20, Packard Instruments) is added to each well, the plates are sealed and radioactivity measured in a Top Count scintillation counter (Packard Instruments). Control wells containing either diluent only (for total counts) or excess MCP-1 (1 μg/mL, for non-specific binding) are used to calculate the percent of total inhibition for compound. The computer program Prism from GraphPad, Inc. (San Diego, Calif.) is used to calculate IC50 values. IC50 values are those concentrations required to reduce the binding of labeled MCP-1 to the receptor by 50%.

Methods of Treatment

Depending on the disease to be treated and the subject's condition, the compounds and compositions of the present invention may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional non toxic pharmaceutically acceptable carriers, adjuvants and vehicles appropriate for each rouse of administration. The present invention also contemplates administration of the compounds and compositions of the present invention in a depot formulation.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5, 0.5 to 5.0, or 5.0 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

Pharmacologics to be Used in Conjunction with CCR2 Compounds

Pharmacological agents that can be used in conjunction with the CCR2 antagonists of the current invention include those used for the treatments of atherosclerosis, restenosis, multiple sclerosis, pulmonary fibrosis, inflammatory bowel disease, rheumatoid arthritis, graft-versus-host disease, renal fibrosis, psoriasis, transplantation rejection, obesity, diabetes, hypercholesterolemia and cancer.

In still other embodiments, the present methods are directed to the treatment of allergic diseases, wherein a compound or composition of the invention is administered either alone or in combination with a second therapeutic agent, wherein said second therapeutic agent is an antihistamine.

When used in combination, the practitioner can administer a combination of the compound or composition of the present invention and a second therapeutic agent. Also, the compound or composition and the second therapeutic agent can be administered sequentially, in any order.

The compounds and compositions of the present invention can be combined with other compounds and compositions having related utilities to prevent and treat the condition or disease of interest, such as inflammatory conditions and diseases, including inflammatory bowel disease, allergic diseases, psoriasis, atopic dermatitis and asthma, and those pathologies noted above. Selection of the appropriate agents for use in combination therapies can be made one of ordinary skill in the art. The combination of therapeutic agents may act synergistically to effect the treatment or prevention of the various disorders. Using this approach, one may be able to achieve therapeutic efficacy with lower dosages of each agent, thus reducing the potential for adverse side effects.

In treating, preventing, ameliorating, controlling or reducing the risk of inflammation, the compounds of the present invention may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing anti-inflammatory agent, for example with a compound such as acetaminophen, aspirin, codeine, biological TNF sequestrants, fentanyl, ibuprofen, indomethacin, ketorolac, morphine, naproxen, phenacetin, piroxicam, a steroidal analgesic, sufentanyl, sunlindac, tenidap, and the like.

Similarly, the compounds of the present invention may be administered with a pain reliever; a potentiator such as caffeine, an H2-antagonist, simethicone, aluminum or magnesium hydroxide; a decongestant such as pseudophedrine; an antitussive such as codeine; a diuretic; a sedating or non-sedating antihistamine; a very late antigen (VLA-4) antagonist; an immunosuppressant such as cyclosporin, tacrolimus, rapamycin, EDG receptor agonists, or other FK-506 type immunosuppressants; a steroid; a non-steroidal anti-asthmatic agent such as a β2-agonist, leukotriene antagonist, or leukotriene biosynthesis inhibitor; an inhibitor of phosphodiesterase type IV (PDE-IV); a cholesterol lowering agent such as a HMG-CoA reductase inhibitor, sequestrant, or cholesterol absorption inhibitor; and an anti-diabetic agent such as insulin, α-glucosidase inhibitors or glitazones.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Methods of Treating or Preventing CCR2-Mediated Conditions or Diseases

In yet another aspect, the present invention provides methods of treating or preventing a CCR2-mediated condition or disease by administering to a subject having such a condition or disease a therapeutically effective amount of any compound of formula (I) above. Compounds for use in the present methods include those compounds according to formula (I), those provided above as embodiments, those specifically exemplified in the Examples below, and those provided with specific structures herein. The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the phrase "CCR2-mediated condition or disease" and related phrases and terms refer to a condition or disease characterized by inappropriate, i.e., less than or greater than normal, CCR2 functional activity. Inappropriate CCR2 functional activity might arise as the result of CCR2 expression in cells which normally do not express CCR2, increased CCR2 expression (leading to, e.g., inflammatory and immunoregulatory disorders and diseases) or decreased CCR2 expression. Inappropriate CCR2 functional activity might also arise as the result of MCP-1 secretion by cells which normally do not secrete MCP-1, increased MCP-1 expression (leading to, e.g., inflammatory and immunoregulatory disorders and diseases) or decreased MCP-1 expression. A CCR2-mediated condition or disease may be completely or partially mediated by inappropriate CCR2 functional activity. However, a CCR2-mediated condition or disease is one in which modulation of CCR2 results in some effect on the underlying condition or disease (e.g., a CCR2 antagonist results in some improvement in patient well being in at least some patients). Furthermore, MCP-2, 3 and 4 are also CCR2 ligands.

In one embodiment, the present invention provides a method of treating a CCR2-mediated condition or disease involving administering to a subject a safe and effective amount of the compound or composition of the invention.

In one embodiment, the present invention provides a method of treating a CCR2-mediated condition or disease involving administering to a subject a safe and effective amount of the compound or composition of the invention, where the CCR2-mediated condition or disease is atherosclerosis.

In one embodiment, the present invention provides a method of treating a CCR2-mediated condition or disease involving administering to a subject a safe and effective amount of the compound or composition of the invention, where the CCR2-mediated condition or disease is restenosis.

In one embodiment, the present invention provides a method of treating a CCR2-mediated condition or disease involving administering to a subject a safe and effective amount of the compound or composition of the invention, where the CCR2-mediated condition or disease is multiple sclerosis.

In one embodiment, the present invention provides a method of treating a CCR2-mediated condition or disease involving administering to a subject a safe and effective amount of the compound or composition of the invention, where the CCR2-mediated condition or disease is selected from the group consisting of inflammatory bowel disease, renal fibrosis, rheumatoid arthritis, obesity and noninsulin-dependent diabetes.

In one embodiment, the present invention provides a method of treating a CCR2-mediated condition or disease involving administering to a subject a safe and effective amount of the compound or composition of the invention, where the CCR2-mediated condition or disease is type 2 diabetes.

In one embodiment, the present invention provides a method of treating a CCR2-mediated condition or disease involving administering to a subject a safe and effective amount of the compound or composition of the invention, where the CCR2-mediated condition or disease is selected from the group consisting of chronic obstructive pulmonary disease, idiopathic pulmonary fibrosis and idiopathic pneumonia syndrome.

In one embodiment, the present invention provides a method of treating a CCR2-mediated condition or disease involving administering to a subject a safe and effective amount of the compound or composition of the invention, where the administering is oral, parenteral, rectal, transdermal, sublingual, nasal or topical.

In one embodiment, the present invention provides a method of treating a CCR2-mediated condition or disease involving administering to a subject a safe and effective amount of the compound or composition of the invention, where the compound is administered in combination with an anti-inflammatory or analgesic agent.

In one embodiment, the present invention provides a method of treating a CCR2-mediated condition or disease involving administering to a subject a safe and effective amount of the compound or composition of the invention, where an anti-inflammatory or analgesic agent is also administered.

In one embodiment, the present invention provides a method of modulating CCR2 function in a cell, where the CCR2 function in the cell is modulated by contacting the cell with a CCR2 modulating amount of the compound of the present invention.

In one embodiment, the present invention provides a method of treating a CCR2-mediated condition or disease involving administering to a subject a safe and effective amount of the compound or composition of the invention, where the disease is selected from the group consisting of pulmonary fibrosis, transplantation rejection, graft-versus-host disease and cancer.

In yet other embodiments, the present methods are directed to the treatment of psoriasis wherein a compound or composition of the invention is used alone or in combination with a second therapeutic agent such as a corticosteroid, a lubricant, a keratolytic agent, a vitamin $D_3$ derivative, PUVA and anthralin.

In other embodiments, the present methods are directed to the treatment of atopic dermatitis using a compound or composition of the invention either alone or in combination with a second therapeutic agent such as a lubricant and a corticosteroid.

In further embodiments, the present methods are directed to the treatment of asthma using a compound or composition of the invention either alone or in combination with a second therapeutic agent such as a β2-agonist and a corticosteroid.

Preparation of Modulators

The following examples are offered to illustrate, but not to limit, the claimed invention.

Additionally, those skilled in the art will recognize that the molecules claimed in this patent may be synthesized using a variety of standard organic chemistry transformations.

Certain general reaction types employed widely to synthesize target compounds in this invention are summarized in the examples. Specifically, generic procedures for sulfonamide formation, pyridine N-oxide formation and 2-aminophenyl-arylmethanone synthesis via Friedel-Crafts type approaches are given, but numerous other standard chemistries are described within and were employed routinely.

While not intended to be exhaustive, representative synthetic organic transformations which can be used to prepare compounds of the invention are included below.

These representative transformations include; standard functional group manipulations; reductions such as nitro to amino; oxidations of functional groups including alcohols and pyridines; aryl substitutions via IPSO or other mechanisms for the introduction of a variety of groups including nitrile, methyl and halogen; protecting group introductions and removals; Grignard formation and reaction with an electrophile; metal-mediated cross couplings including but not limited to Buchwald, Suzuki and Sonigashira reactions; halogenations and other electrophilic aromatic substitution reactions; diazonium salt formations and reactions of these species; etherifications; cyclative condensations, dehydrations, oxidations and reductions leading to heteroaryl groups; aryl metallations and transmetallations and reaction of the ensuing aryl-metal species with an electrophile such as an acid chloride or Weinreb amide; amidations; esterifications; nucleophilic substitution reactions; alkylations; acylations; sulfonamide formation; chlorosulfonylations; ester and related hydrolyses, and the like.

Certain molecules claimed in this patent can exist in different enantiomeric and diastereomeric forms and all such variants of these compounds are within the scope of the invention.

In the descriptions of the syntheses that follow, some precursors were obtained from commercial sources. These commercial sources include Aldrich Chemical Co., Acros Organics, Ryan Scientific Incorporated, Oakwood Products Incorporated, Lancaster Chemicals, Sigma Chemical Co., Lancaster Chemical Co., TCI-America, Alfa Aesar, Davos Chemicals, and GFS Chemicals.

Compounds of the invention, including those listed in the table of activities, can be made by the methods and approaches described in the following experimental section, and by the use of standard organic chemistry transformations that are well known to those skilled in the art.

EXAMPLES

The following compounds are within the scope of the invention:

TABLE 1

Compounds according to the formula:

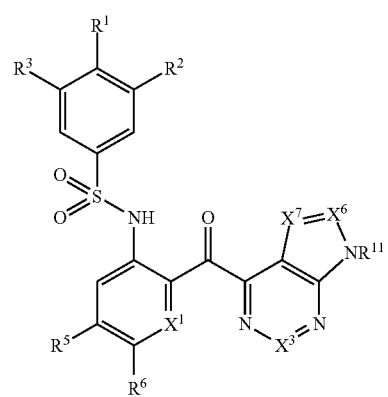

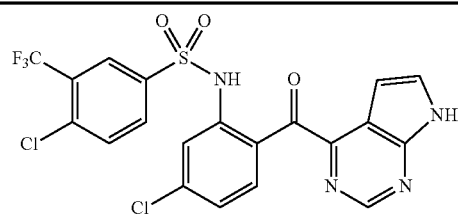

1

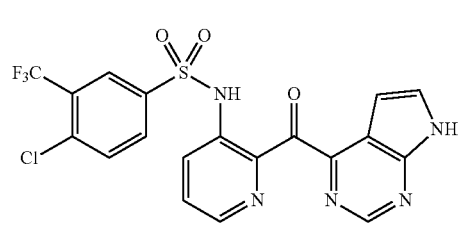

2

TABLE 1-continued
Compounds according to the formula:
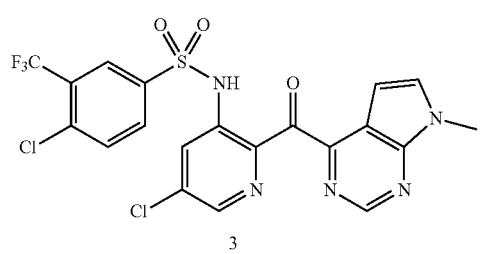 [SMILES: Cn1ccc2c(C(=O)c3ncc(Cl)cc3NS(=O)(=O)c3ccc(Cl)c(C(F)(F)F)c3)ncnc21]
3
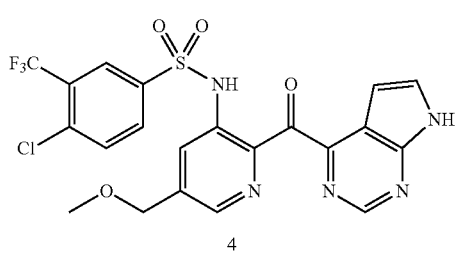
4
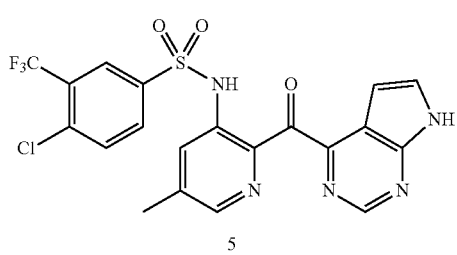 [SMILES: Cc1cnc(C(=O)c2ncnc3[nH]ccc23)c(NS(=O)(=O)c2ccc(Cl)c(C(F)(F)F)c2)c1]
5
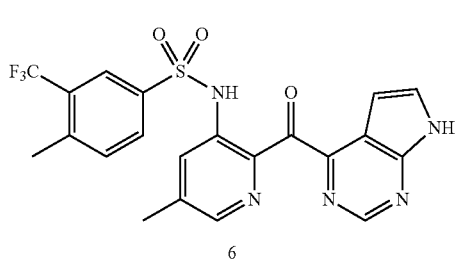 [SMILES: Cc1cnc(C(=O)c2ncnc3[nH]ccc23)c(NS(=O)(=O)c2ccc(C)c(C(F)(F)F)c2)c1]
6
TABLE 1-continued
Compounds according to the formula:
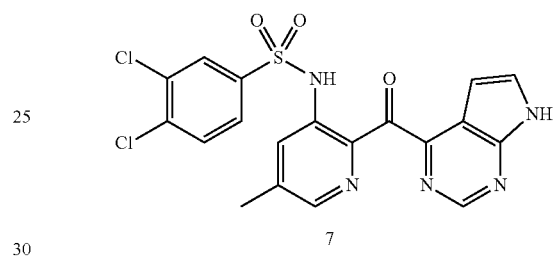
7
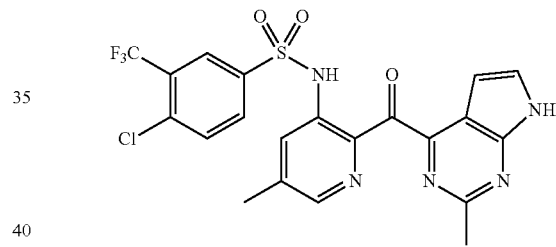
8
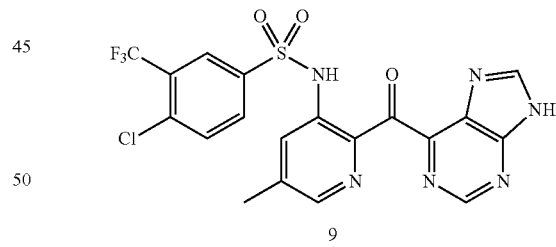
9
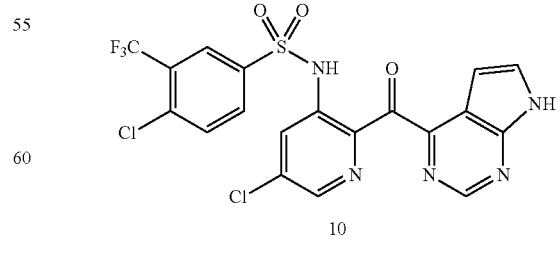
10
Compounds 1-10 have an $IC_{50}$ of less than 1000 nM in the CCR2 chemotaxis assay.

TABLE 2

Compounds according to the formula:

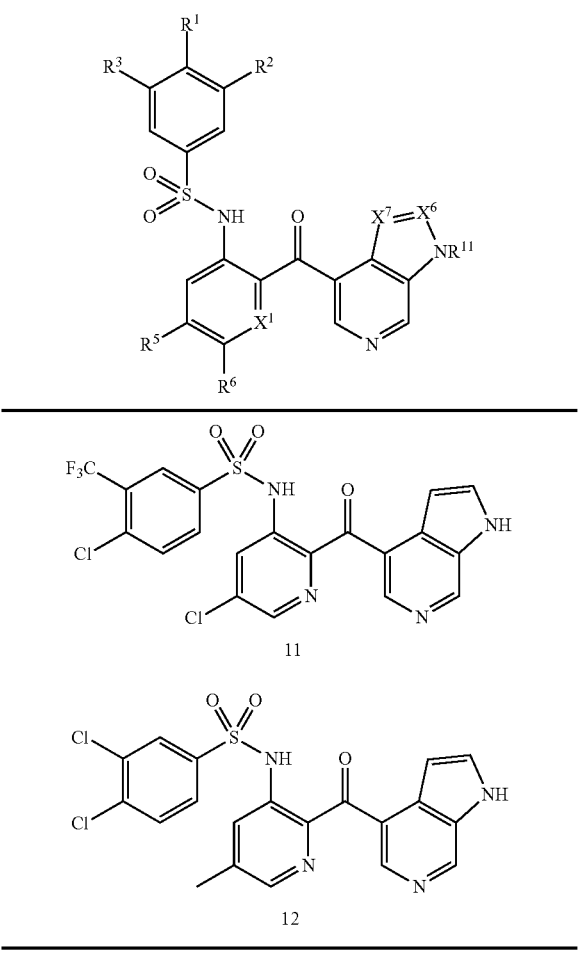

Compounds 11 and 12 have an IC$_{50}$ of less than 1000 nM in the CCR2 chemotaxis assay.

The above compounds and others within the scope of this invention were made and found to be active CCR2 antagonists using the following procedures.

Reagents and solvents used below can be obtained from commercial sources such as Aldrich Chemical Co. (Milwaukee, Wis., USA). $^1$H-NMR were recorded on a Varian Mercury 400 MHz NMR spectrometer. Significant peaks are tabulated in the order: multiplicity (br, broad; s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

Preparation of Intermediates

Intermediate 1: 4-Chloro-2-(4-chloro-3-trifluoromethyl-benzenesulfonylamino)-benzoic acid

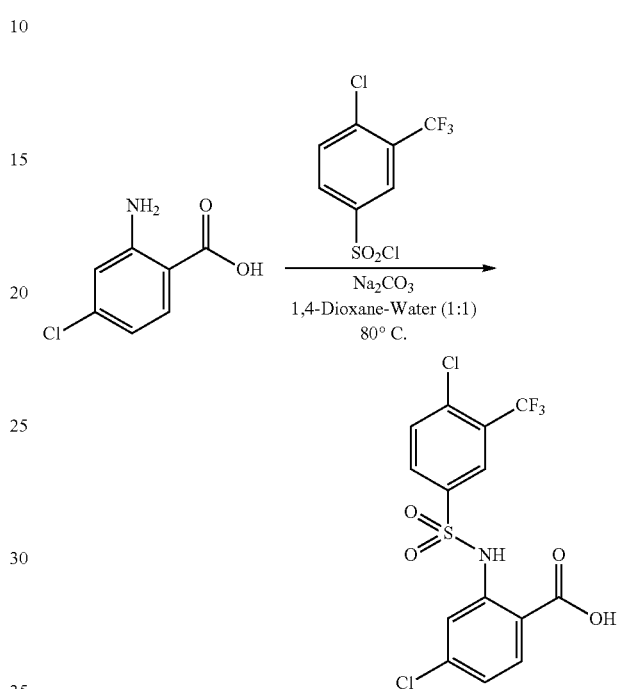

To a solution of Na$_2$CO$_3$ (11.7 g, 110.7 mmol) in water (50 mL) and 1,4-dioxane (50 mL) at 60° C. was added 2-amino-4-chloro-benzoic acid (5.0 g, 29.14 mmol) followed by 4-chloro-3-trifluoromethyl-benzenesulfonyl chloride (20.15 g, 72.48 mmol) in 3 portions and heated the resulting reaction mixture at 80° C. for 4 hours. 2N HCl Was added until the reaction mixture became acidic (pH=~2) and obtained white solid was filtered, washed with water, dried under high vacuum to obtain title compound (7.8 g) in 65% yield. MS (ES) M+Na expected 436.0, found 435.8.

Intermediate 2: 4-Chloro-2-(4-chloro-3-trifluoromethyl-benzenesulfonylamino)-N-methoxy-N-methyl-benzamide

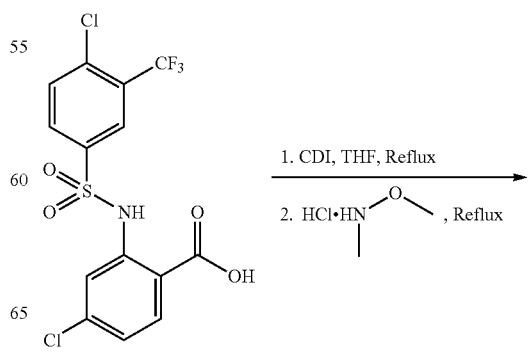

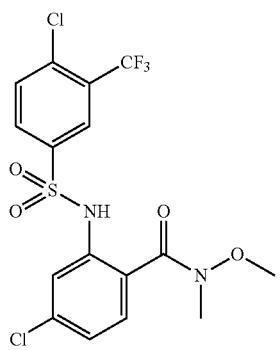

To a solution of 4-chloro-2-(4-chloro-3-trifluoromethyl-benzenesulfonylamino)-benzoic acid (5.0 g, 12.1 mmol) in THF (20 mL) was added N,N'-carbonyldiimidazole (CDI, 2.45 g, 15.13 mmol) in portions (Caution!: $CO_2\uparrow$). The resulting reaction mixture was then heated at reflux. After 4 hours, reaction mixture was cooled to room temperature and charged with N,O-dimethylhydroxylamine hydrochloride (1.3 g, 13.31 mmol) and heated at reflux for 1 hour. Water (100 mL) was added followed by EtOAc (100 mL) with stirring. EtOAc layer was separated and aqueous layer was further extracted with EtOAc (2×50 mL). Combined EtOAc layers were washed with aq. 2N HCl (50 mL), saturated $NaHCO_3$ solution (50 mL), brine (50 mL), dried ($Na_2SO_4$) and evaporated. Obtained crude product was purified by automated normal-phase chromatography (50% EtOAc in hexanes) to afford title compound (4.0 g) in 73% yield. MS (ES) M+H expected 457.0, found 456.9.

Intermediate 3: 2-Bromo-5-methyl-3-nitropyridine

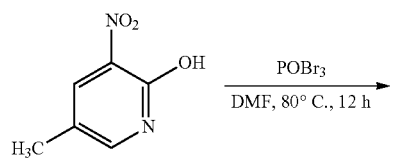

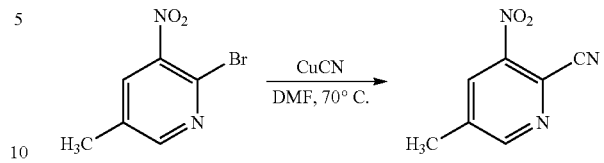

$POBr_3$ (222.8 g, 0.78 mol) was added in portions to 2-hydroxy-5-methyl-3-nitropyridine (100 g, 0.65 mol) in DMF (500 mL) with stirring at 0-10° C. then the reaction mixture was stirred at 80° C. under nitrogen for 12 hours. Reaction mixture was cooled and poured into crushed ice (1 Kg), obtained solid was filtered, washed thoroughly with ice-cold water (2×500 mL), dried in a desiccator under high vacuum for one day to obtain 2-bromo-5-methyl-3-nitropyridine as yellow solid (121 g) in 86% yield. (M+H) Expected: 217; found 216.9.

Intermediate 4: 2-Cyano-5-methyl-3-nitropyridine

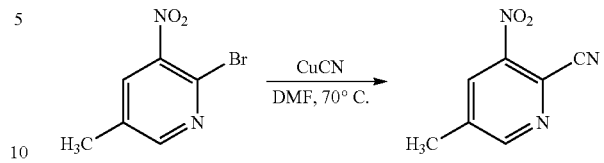

A round bottom flask was charged with 2-bromo-5-methyl-3-nitropyridine (60.53 g, 278.9 mmol) and CuCN (27.52 g, 307.3 mmol) The flask was evacuated, and back-filled with nitrogen. DMF (150 mL) was added via cannula. The solution was heated to 70° C. for 1.5 hours. After cooling to room temperature, the reaction mixture was poured into EtOAc (500 mL) and water (250 mL). Both phases were filtered through a 1 cm bed of celite. The layers were separated, and the organic phase washed with water (2×100 mL) then with a solution of 1:1 sat. aq. $NH_4Cl/NH_4OH$ (2×100 mL). The combined aqueous layers were extracted with EtOAc (2×200 mL). The combined organic layers were dried over $MgSO_4$ and concentrated in vacuo to afford the title compound (36.10 g, 79% yield).

Intermediate 5: 3-Amino-2-cyano-5-methylpyridine

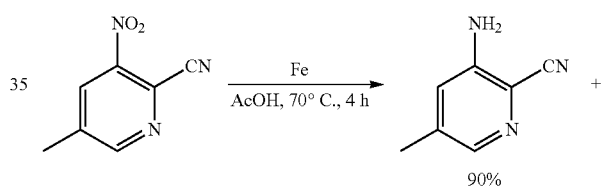

To acetic acid (300 mL) in a 3-neck 2 liter round bottom flask equipped with mechanical stirrer and a thermometer was added Fe powder (99.6 g, 1.78 mol) with stirring at 60° C. 2-Cyano-5-methyl-3-nitropyridine (97 g, 0.59 mol) was dissolved in acetic acid (400 mL) with gentle warming and added to the above reaction mixture drop wise with efficient stirring so that the reaction temperature kept below 80° C. over 3.5 hours. The reaction mixture was further stirred for an addition 30 min, cooled, diluted with EtOAc (750 mL), filtered through celite and washed with EtOAc (1×500 mL, 3×250 mL). Combined EtOAc layers were evaporated to dryness to obtain dark brown solid which was neutralized with saturated $NaHCO_3$ solution (850 mL), after addition of water (250 mL) to obtain homogeneous, this aqueous layer was extracted with EtOAc (1×750 mL, 2×500 mL). Combined EtOAc layers were filtered through small pad of silica gel (sand-$SiO_2$-sand in sintered funnel), dried ($Na_2SO_4$) and evaporated to obtain 3-amino-2-cyano-5-methylpyridine (60 g) as yellow solid in 76% yield including ~10% corresponding amide.

To the crude 3-amino-2-cyano-5-methylpyridine (containing ~10% carboxamide) (49 g) was added EtOAc (441 mL, 9:1 volume ratio to aniline), the resulting suspension was heated to reflux to form a clean solution. After cooling to room temperature, the resulting crystal was collected by filtration, washed with small amount of cold EtOAc (44 mL (1/10 the initial volume)×2), and dried in vacuo to afford the pure 3-amino-2-cyano-5-methylpyridine (35 g) as pale yellow needles. The mother liquor was concentrated under reduced pressure, the resulting yellow solid was added EtOAc (136 mL) and repeated the above process to afford another 4 g of pure 3-amino-2-cyano-5-methylpyridine; total recovery yield 79.5%. $^1$H NMR (400 MHz, CDCl$_3$) δ 7.89 (1H, s), 6.90 (1H, s), 4.39 (2H, br), 2.30 (3H, s). MS (ES) M+H expect 134.0, found 134.0.

Intermediate 6: 3-(4-Chloro-3-trifluoromethyl-benzenesulfonylamino)-5-methyl-pyridine-2 carboxylic acid

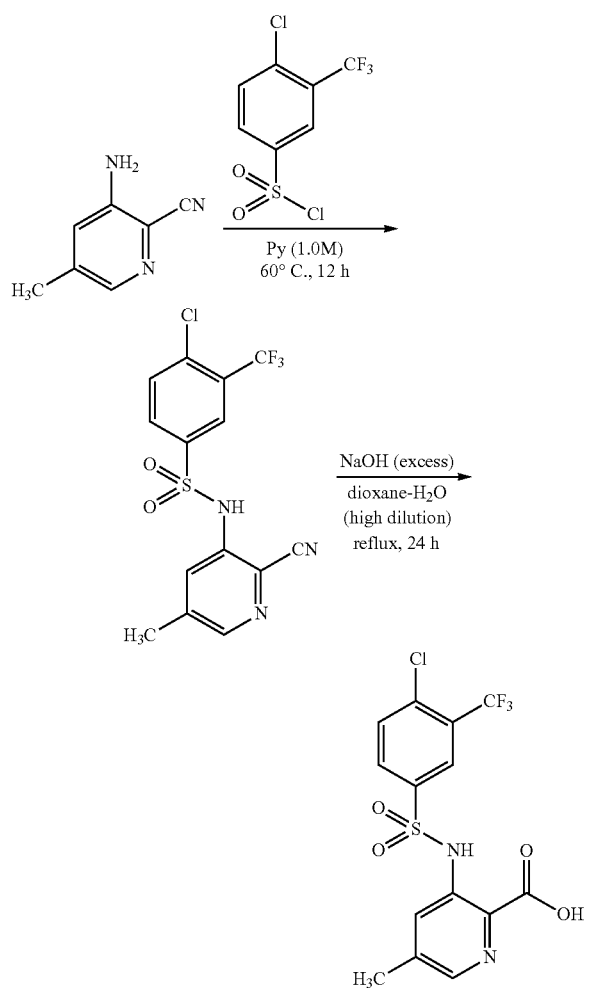

To 3-amino-5-methylpicolinonitrile (9.6 g, 72 mmol) in pyridine (63 mL) was added 4-chloro-3-trifluoromethyl-benzenesulfonyl chloride (19.6 g, 80 mmol) in one portion and the resulting reaction mixture was stirred at 60° C. for overnight. Pyridine was removed in vacuo, added 2N HCl (100 mL), extracted with EtOAc (3×300 mL; Note: due to the amide presence, solubility in EtOAc is low). Combined EtOAc layers were dried (Na$_2$SO$_4$), evaporated to obtain 26.3 g of crude product which contained a small amount of bis-sulfonamide which was subjected to hydrolysis in THF (200 mL) with 2N NaOH (100 mL) at room temperature for 2 hours. 2 N HCl (100 mL) Was added, extracted with EtOAc (1×700 mL, 1×250 mL), combined EtOAc layers were washed with saturated NaHCO$_3$ solution (2×250 mL), dried (Na$_2$SO$_4$) and evaporated to obtain 22 g of monosulfonamide. To this dioxane (350 mL), water (450 mL) (Note: requires high dilution for fast reaction) was added, followed by NaOH (30 g, 0.75 mol) and stirred under reflux for 24 hours. Dioxane was removed in vacuo and conc. HCl (75 mL) was added slowly with cooling. The resultant solid was filtered, washed with water and dried in vacuo to afford title compound (22 g, 88% for 2 steps) as light yellow solid. (M+H) Expected: 395.0; found 394.9.

Intermediate 7: 5-Chloro-3-(4-chloro-3-(trifluoromethyl)phenyl-sulfonamido)picolinic acid

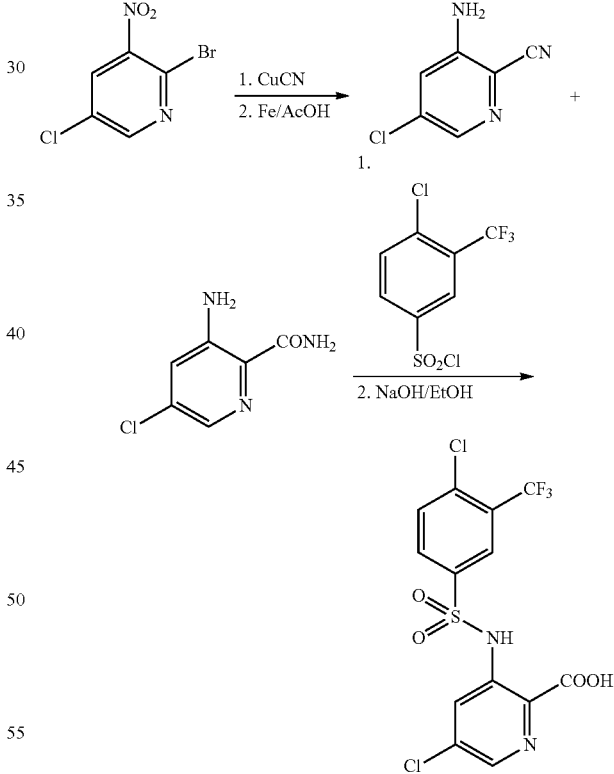

Step 1: A dry 250 mL flask was charged with 2-bromo-5-chloro-3-nitropyridine (24 g, 101 mmol), CuCN (19 g, 212 mmol) and DMF (100 mL). The resultant mixture was stirred at 110° C. for 2 hours. The mixture was concentrated under reduced pressure. Water (100 mL) was added and extracted with EtOAc (3×250 mL). The combined organic layer was washed with brine, dried (MgSO$_4$) and filtered. The solvent was evaporated the solvent in vacuo to afford a light yellow solid (15 g) which was used directly for the next step.

Step 2: A 250 mL round-bottom flask with a magnetic stir bar was charged with iron powder (15.6 g, 0.3 mol) in acetic acid (80 mL) and heated to 80° C. (oil bath) under $N_2$. To this mixture was added slowly the above nitrocyanopyridine (10 g, 55 mmol) from step 1 in acetic acid (80 mL) via dropping funnel over 15 minutes. The mixture was stirred at 80° C. for another 30 min after the addition. After cooling, the reaction mixture was diluted with EtOAc, filtered through celite and the solvent evaporated in vacuo. The residue was dissolved in EtOAc and washed with 3 N NaOH, brine, dried over $MgSO_4$, and concentrated in vacuo to afford a 4:1 mixture (7.7 g) of 3-amino-2-cyano-5-chloropyridine (major) and the 2-amide. The mixture was used directly for the next step: MS (ES) $(M+H)^+$ expected 154.0, found 154.0.

Step 3: A 100 mL round-bottom flask was charged with the above 3-amino-2-cyano-5-chloropyridine mixture (7.7 g, 50 mmol), 4-chloro-3-trifluoromethylbenzenesulfonyl chloride (28 g, 100 mmol), and pyridine (50 mL). The resultant solution was heated to 70° C. and stirred for 5 hours. The pyridine was removed in vacuo and 80% aq. EtOH (260 mL) was added, followed by NaOH (30 g, 0.75 mol). The mixture was stirred under reflux for 12 hours. The solvent was subsequently removed in vacuo and ice (100 g) was added. The pH adjusted to 2-3 with conc. HCl. The resultant aqueous solution was extracted with EtOAc, washed with brine, dried over $MgSO_4$, and concentrated in vacuo. The resulting light yellow solid was recrystallized from EtOAc/hexane (1:1) to afford the desired acid as white needles (10 g, 44% overall yield): $^1$H NMR (400 MHz, $CDCl_3$) δ 10.80 (s, 1H), 8.23 (m, 3H), 8.00 (d, 1H), 7.63 (d, 1H); MS (ES) $(M+H)^+$ expected 415.0, found 415.0.

Intermediate 8: 5-Chloro-3-(4-chloro-3-trifluoromethyl-benzenesulfonylamino)-pyridine-2-carboxylic acid methoxy-methyl-amide

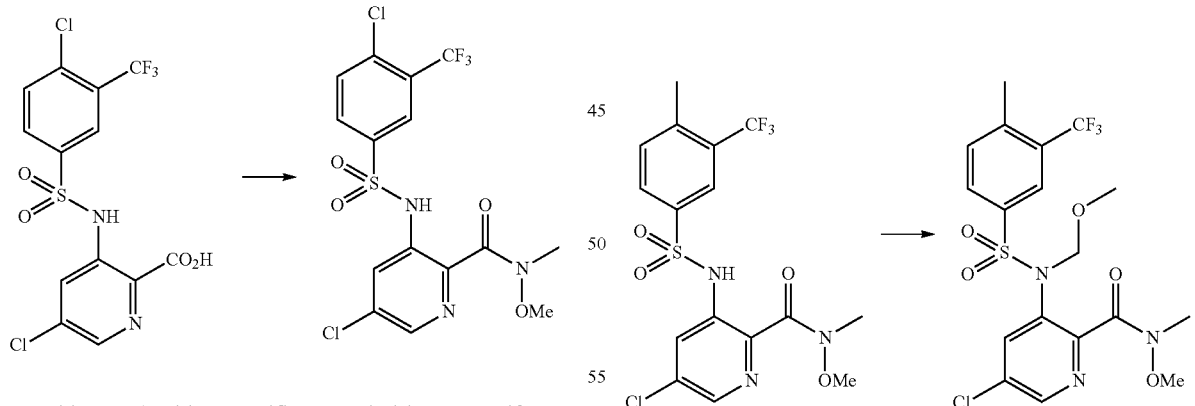

5-Chloro-3-(4-chloro-3-trifluoromethyl-benzenesulfonylamino)-pyridine-2-carboxylic acid (15.8 g, 38 mmol), N,O-dimethyl hydroxylamine hydrochloride (11.1 g, 114 mmol), DIEA (41 mL, 228 mmol), and BOP (69 g, 156 mmol), were suspended in 80 mL DMF and stirred at room temperature over night. The reaction mixture was diluted with 1 (M) HCl (100 mL), extracted with EtOAc, and the organic portions were washed with 1 (M) aqueous HCl, $NaHCO_3$ and brine. The combined organic extracts were dried ($Na_2SO_4$), filtered and concentrated under reduced pressure. The resulting residue was purified by flash column chromatography to afford 5-chloro-3-(4-chloro-3-trifluoromethyl-benzenesulfonylamino)-pyridine-2-carboxylic acid methoxy-methyl-amide: MS m/z: (M+H) 458.0.

Intermediate 9: 5-Chloro-3-(4-methyl-3-trifluoromethyl-benzenesulfonylamino)-pyridine-2-carboxylic acid methoxy-methyl-amide

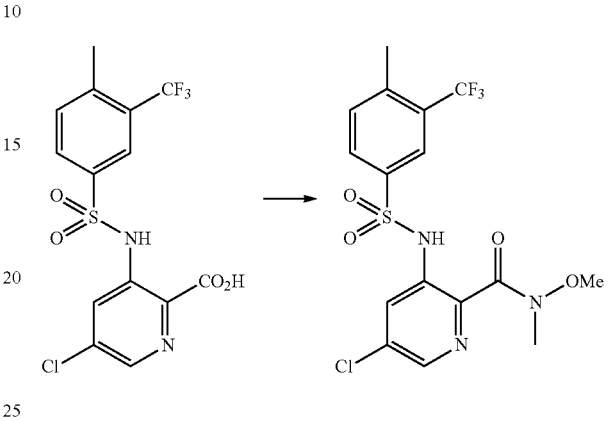

Intermediate 10: 5-Chloro-3-(4-methyl-3-trifluoromethyl-benzenesulfonylamino)-pyridine-2-carboxylic acid methoxy-methyl-amide was Prepared from 5-chloro-3-(4-methyl-3-trifluoromethyl-benzenesulfonylamino)-pyridine-2-carboxylic acid Following the Procedure Described in the Preceding Example Intermediate 11: 5-Chloro-3-[methoxymethyl-(4-methyl-3-trifluoromethyl-benzenesulfonyl)-amino]-pyridine-2-carboxylic acid methoxy-methyl-amide To a mixture of sodium hydride (164 mg, 4.10 mmol) in 5 mL of THF was added a mixture of 5-chloro-3-(4-methyl-3-trifluoromethyl-benzenesulfonylamino)-pyridine-2-carboxylic acid methoxy-methyl-amide (1.50 g, 3.42 mmol) and chloromethyl methyl ether (0.388 mL, 5.13 mmol) in 5 mL of THF. The mixture was stirred at room temperature overnight. After the removal of the solvents the residue was purified by flash column (20% ethyl acetate in hexane) to afford 1.50 grams of the title compound as a white solid: (M⁺+H) expect 482.0, found 482.0.

Intermediate 12: 5-Chloro-3-[methoxymethyl-(4-chloro-3-trifluoromethyl-benzenesulfonyl)-amino]-pyridine-2-carboxylic acid methoxy-methyl-amide

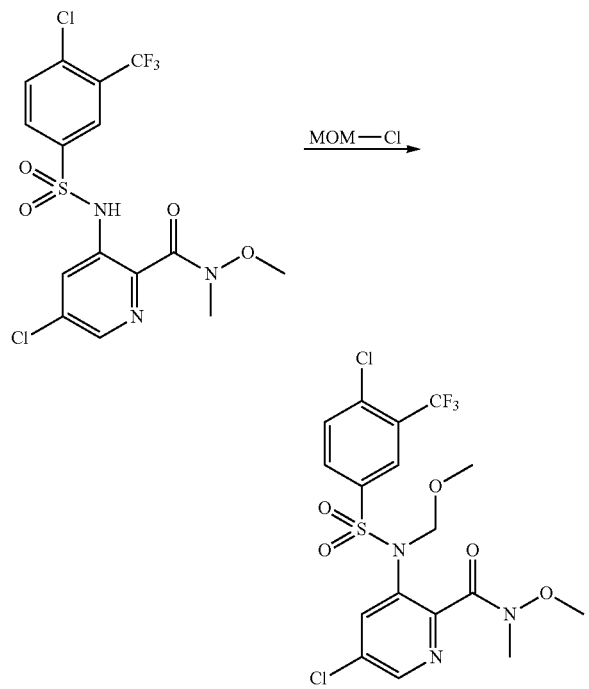

To a suspension of sodium hydride (314 mg, 7.86 mmol) in 8 mL of THF was added a mixture of 5-chloro-3-(4-chloro-3-trifluoromethyl-benzenesulfonylamino)-pyridine-2-carboxylic acid methoxy-methyl-amide (3.0 g, 6.55 mmol) and chloromethyl methyl ether (0.741 mL, 9.825 mmol) in 8 mL of THF. The mixture was stirred at room temperature overnight. After the removal of the solvents the residue was purified by flash column (20% ethyl acetate in hexane) to afford 2.70 grams of the title compound as a white solid. (M+H)⁺ expect 502.0, found 502.0.

Intermediate 13: 3-Amino-pyridine-2-carboxylic acid methyl ester

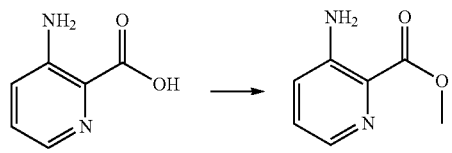

400 mg (2.9 mmol) of 3-amino-pyridine-2-carboxylic acid was dissolved in 3 mL of methanol. To this solution 1.6 mL of 2 M (trimethylsilyl)diazomethane solution in diethyl ether was added dropwise at 0° C., followed by stirring of the mixture for 2 hours at room temperature The solution was diluted with ethyl acetate and washed with aqueous sodium bicarbonate solution. Flash chromatography afforded the ester product. LC-MSD, m/z for $C_7H_8N_2O_2$ [M+H]+=153.0; HPLC retention time: 0.2 minutes.

Intermediate 14: 3-(4-Chloro-3-trifluoromethyl-benzenesulfonylamino)-pyridine-2-carboxylic acid

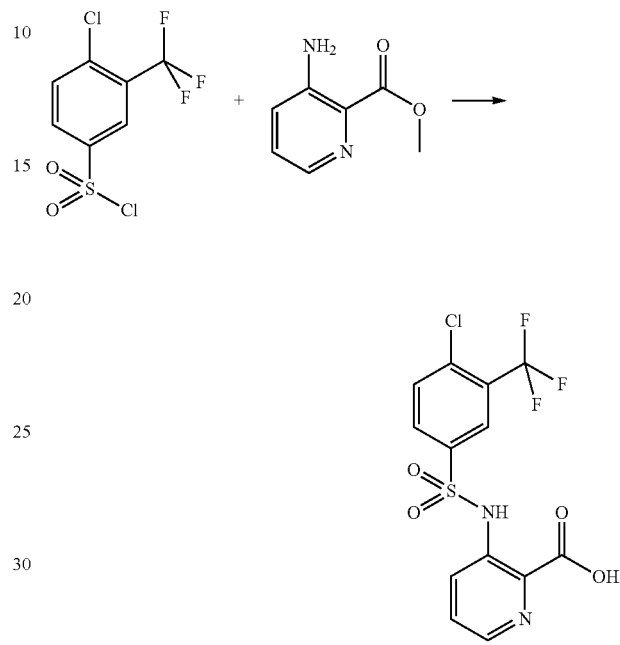

Prepared from 0.60 g (2.17 mmol) of 4-chloro-3-trifluoromethyl-benzenesulfonyl chloride and 0.30 g (1.97 mmol) of 3-amino-pyridine-2-carboxylic acid methyl ester in 3 mL pyridine using the procedure used to prepare 4-chloro-N-(2-cyano-5-methylpyridin-3-yl)-3-(trifluoromethyl)benzenesulfonamide in the preparation of Intermediate 6. The solvent was switched to THF, followed by the addition of 1 M aqueous LiOH and the mixture stirred for 1 hour. The pH of the mixture was adjusted to neutral and the product was extracted with ethyl acetate. LC-MSD, m/z for $C_{13}H_8ClF_3N_2O_4S$ [M+H]+=380.9, 383.0; HPLC retention time: 1.8 minutes.

Intermediate 15: 3-[(4-Chloro-3-trifluoromethyl-benzenesulfonyl)-methoxymethyl-amino]-pyridine-2-carboxylic acid methoxy-methyl-amide

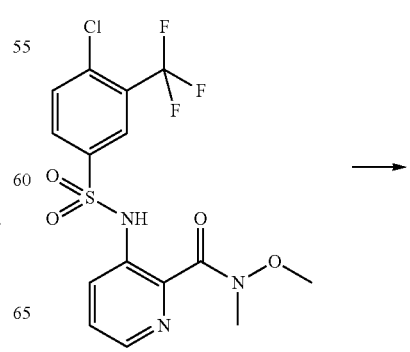

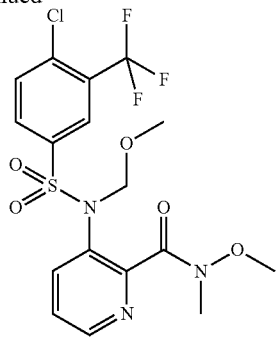

Prepared from 1.05 g (2.48 mmol) of 3-(4-chloro-3-trifluoromethyl-benzenesulfonylamino)-pyridine-2-carboxylic acid methoxy-methyl-amide, 1.71 g of potassium carbonate and 566 μL of methoxymethyl chloride in 7 mL THF using procedure used in the preparation of Intermediate 12. Yield: 420 mg of a white solid. LC-MSD, m/z for $C_{17}H_{17}ClF_3N_3O_5S$ [M+Na]+=490.0, 491.9; HPLC retention time: 2.5 minutes.

Intermediate 16: 4-Chloro-N-(2-(5-methoxy-1H-pyrrolo[2,3-b]pyridine-4-carbonyl)-5-(methoxymethyl)pyridin-3-yl)-3-(trifluoromethyl)benzenesulfonamide

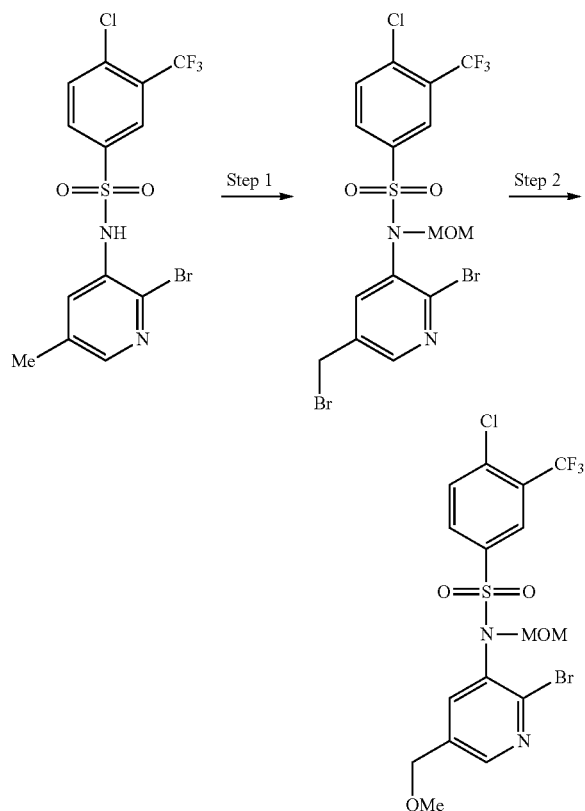

Step 1: To a solution of the bromopyridine (132 mg, 0.28 mmol) in carbon tetrachloride (4 mL) was added N-bromosuccinimide (60 mg, 1.2 equiv.), followed by 2,2'-azobisisobutyronitrile (AIBN, 4.6 mg, 0.1 equiv.). The reaction mixture was heated at 60° C. overnight. After cooling down to room temperature, excessive carbon tetrachloride was removed and the residue was purified by flash chromatography on silica gel (33% EtOAc/hexanes). The desired product was obtained as a white solid (107 mg, 70%). MS: (M+H)/z=551.

Step 2: The product obtained from step 1 above (51 mg, 0.093 mmol) was dissolved in 3 mL of methanol. To the resultant solution was added sodium methoxide (10 mg, 2.0 equiv.). The reaction mixture was heated at 50° C. overnight. After cooling down to room temperature, the reaction was quenched with saturated ammonium chloride solution, and the mixture was extracted with ethyl acetate. The extracts were washed with brine, dried over $MgSO_4$ and concentrated in vacuo. The crude material was purified by flash chromatography on silica gel (33% EtOAc/hexanes). The desired product was obtained as a white solid (42 mg, 90%). MS: (M+H)/z=503.

Intermediate 17: 3-(4-Chloro-3-trifluoromethyl-benzenesulfonylamino)-5-methyl-pyridine-2-carboxylic acid methoxy-methyl-amide

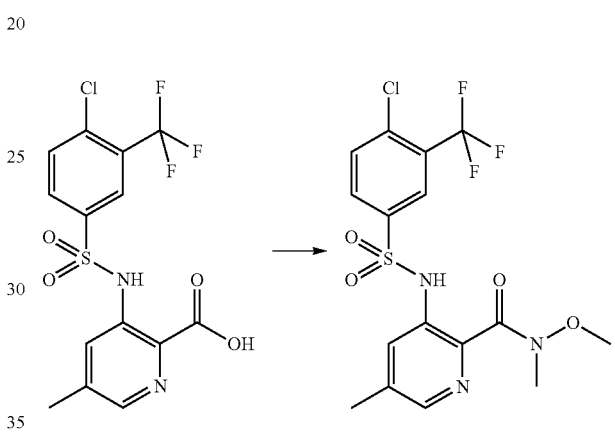

10.49 g (26.6 mmol) of 3-(4-chloro-3-trifluoromethyl-benzenesulfonylamino)-5-methyl-pyridine-2-carboxylic acid was reacted with 5.40 g (33.2 mmol) of N,N'-carbonyldiimidazole in 40 mL of refluxing THF for 3 h. The temperature was lowered to 50° C., 2.86 g (29.3 mmol) of O,N-dimethyl-hydroxylamine hydrochloride was added and the reaction was stirred overnight at 50° C. Half of the solvent was removed under reduced pressure and the reaction mixture was diluted with 200 mL of cold water. The solids were filtered off, washed with 100 mL of water and dried to give 9.8 g (84%) of the product as a tan powder.

Intermediate 18: 3-[(4-Chloro-3-trifluoromethyl-benzenesulfonyl)-methoxymethyl-amino]-5-methyl-pyridine-2-carboxylic acid methoxy-methyl-amide

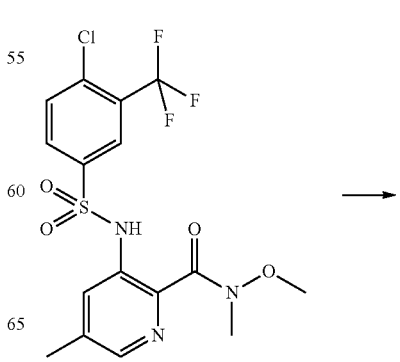

-continued

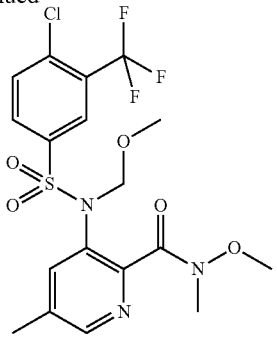

Prepared from 223 mg (0.51 mmol) of 3-(4-chloro-3-trifluoromethyl-benzenesulfonylamino)-5-methyl-pyridine-2-carboxylic acid methoxy-methyl-amide, 352 mg of potassium carbonate and 116 μL of methoxymethyl chloride in 1 mL THF using the procedure used to prepare Intermediate 12. Yield: 200 mg of a white solid. LC-MSD, m/z for $C_{18}H_{19}ClF_3N_3O_5S$ [M+H]+=482.0, 484.0; HPLC retention time: 2.5 minutes.

Intermediate 19:
7-Chloro-3H-imidazo[4,5-b]pyridine

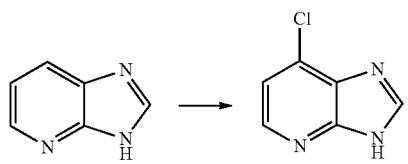 [SMILES: c1cnc2[nH]cnc2c1 ; Clc1ccnc2[nH]cnc12]

The product was prepared following the procedure from *Bioorg. Med. Chem. Lett.* 2004, 3165-3168.

Intermediate 20: 6-Iodo-9H-purine

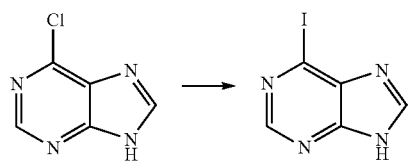 [SMILES: Clc1ncnc2[nH]cnc12 ; Ic1ncnc2[nH]cnc12]

A mixture of 6-chloro-9H-purine (684 mg, 4.46 mmol) and 6 mL of 57% hydriodic acid were stirred at 0° C. for 1.5 hours. The reaction yielded 840 mg of the product as a white powder. The solid was filtered off, suspended in 5 mL of water and brought to pH=8 with aqueous ammonia solution. The suspension was cooled down to 0° C. and the solid was filtered off, washed with cold water and dried to give the product.

Intermediate 21:
4-Iodo-7H-pyrrolo[2,3-d]pyrimidine

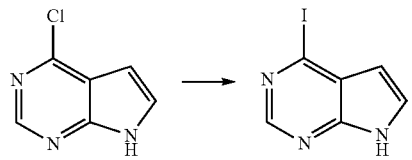 [SMILES: Clc1ncnc2[nH]ccc12 ; Ic1ncnc2[nH]ccc12]

A mixture of 4-chloro-7H-pyrrolo[2,3-d]pyrimidine (673 mg, 4.41 mmol) and 7 mL of 57% hydriodic acid was stirred at room temperature for 16 hours. The solid was filtered off, suspended in 5 mL of water and brought to pH=8 with aqueous ammonia solution. The suspension was cooled down to 0° C. and the solid was filtered off, washed with cold water and dried to give the product to yield 970 mg of the product as a white powder. The product contains about 10% of the starting material.

Intermediate 22: 7-Iodo-3H-imidazo[4,5-b]pyridine

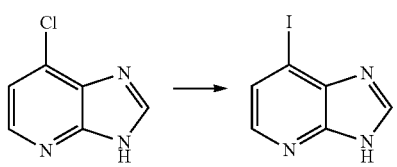 [SMILES: Clc1ccnc2[nH]cnc12 ; Ic1ccnc2[nH]cnc12]

A mixture of 7-chloro-3H-imidazo[4,5-b]pyridine (1.47 g, 9.64 mmol) and 15 mL of 57% hydriodic acid were reacted at 80° C. for 4 hours. After the solid was filtered off it was resubmitted to the reaction with 10 mL of fresh 57% hydriodic acid. The reaction yielded 1.3 g of the product as a black powder, 90% pure.

General Procedure for N-Protection of the Iodoheterocycles 1.65 mmol of the iodoheterocycle was dissolved in 2 mL DMF and cooled down to 0° C. To this solution 1.81 mmol of 60% sodium hydride was added followed by dropwise addition of 1.81 mmol of trimethylsilylethoxymethyl chloride over the period of 5 minutes. The solution was stirred at 0° C. for 0.5 h, followed by 0.5 h at room temperature To this solution 10 mL of water was added and the mixture was extracted twice with 10 mL of diethyl ether. The organic layers were washed with 10 mL of water, then dried over anhydrous magnesium sulfate, evaporated under reduced pressure and purified on silica using ethyl acetate in hexanes.

Intermediate 23: 6-Iodo-9-(2-trimethylsilanyl-ethoxymethyl)-9H-purine

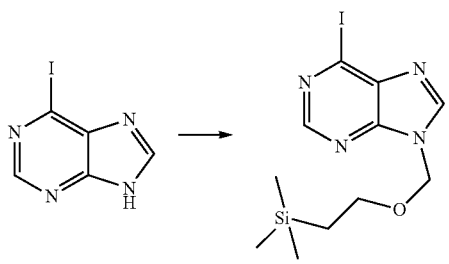 [SMILES: Ic1ncnc2[nH]cnc12 ; C[Si](C)(C)CCOCn1cnc2c(I)ncnc21]

405 mg (1.65 mmol) of 6-iodo-9H-purine was dissolved in 2 mL DMF. 72 mg (1.81 mmol) of 60% sodium hydride was added followed by 320 μL (1.81 mmol) of trimethylsilylethoxymethyl chloride. Yield: 343 mg of an oily product.

Intermediate 24: 4-Iodo-7-(2-trimethylsilanylethoxymethyl)-7H-pyrrolo[2,3-d]pyrimidine

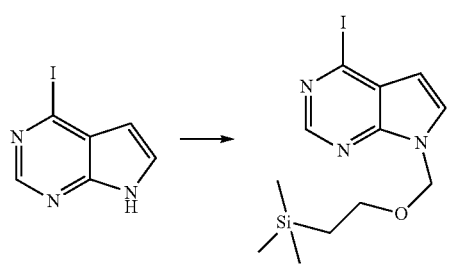 [SMILES: Ic1ncnc2[nH]ccc12 ; C[Si](C)(C)CCOCn1ccc2c(I)ncnc21]

610 mg (2.49 mmol) of 4-iodo-7H-pyrrolo[2,3-d]pyrimidine was dissolved in 2.5 mL DMF. 110 mg (2.74 mmol) of 60% sodium hydride was added followed by 480 μL (2.74 mmol) of trimethylsilylethoxymethyl chloride. Yield: 750 mg of an oily product, 90% pure.

Intermediate 25: 4-Iodo-7-methyl-7H-pyrrolo[2,3-d]pyrimidine

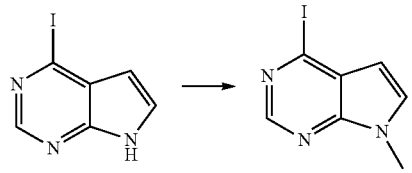

206 mg (0.84 mmol) of 4-iodo-7H-pyrrolo[2,3-d]pyrimidine was dissolved in 1 mL DMF. 37 mg (0.92 mmol) of 60% sodium hydride was added followed by 58 μL (0.92 mmol) of iodomethane. The reaction was quenched by adding 10 mL of water, the solid filtered off, washed with 10 mL of water, then 10 mL of hexanes and dried. Yield: 142 mg of a tan powder, 90% pure.

Intermediate 26: 7-Iodo-3-(2-trimethylsilanylethoxymethyl)-3H-imidazo[4,5-b]pyridine

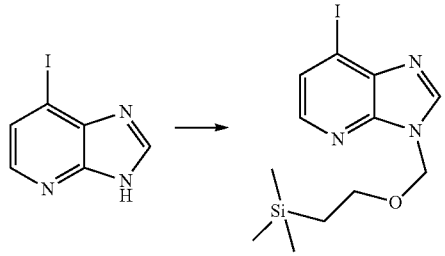 [SMILES: Ic1ccnc2[nH]cnc12 ; C[Si](C)(C)CCOCn1cnc2c(I)ccnc21]

850 mg (3.47 mmol) of 7-iodo-3H-imidazo[4,5-b]pyridine was dissolved in 3.5 mL DMF. 153 mg (3.82 mmol) of 60% sodium hydride was added followed by 670 μL (3.82 mmol) of trimethylsilylethoxymethyl chloride. Yield: 424 mg of an oily product, 90% pure.

General Procedure A: Preparation of Ketones from Weinreb Amides

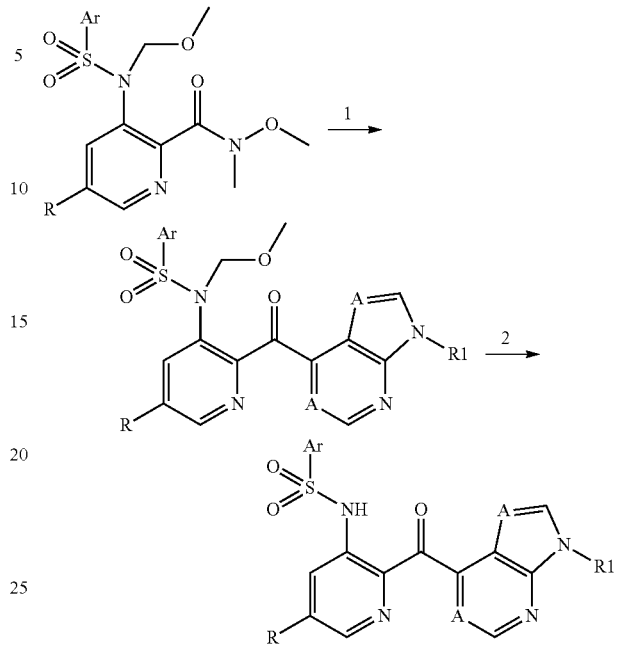

Step 1: Addition of the Grignard Reagent 1 mmol of the iodoheterocycle was dissolved under nitrogen atmosphere in 4 mL THF and cooled down to −30° C. 0.50 mL of 2 M solution of isopropylmagnesium chloride solution in THF was added dropwise. The mixture was warmed up to −10° C. and stirred for 10 minutes, which resulted in a complete iodine-magnesium exchange. The solution was then cooled down to −20° C. and 1.0 mmol of solid Weinreb amide was added. After 5 minutes the mixture was allowed to warm up to room temperature and was stirred at room temperature for 1 hour. Aqueous ammonium chloride solution was added and the mixture was extracted with DCM. Organic layer was evaporated under reduced pressure. Flash chromatography on silica using ethyl acetate in hexanes afforded the products.

Step 2: Deprotection 1 mmol of the protected ketone intermediate was dissolved in a mixture of 20 mL of methanol and 20 mL of 6N hydrochloric acid. The solution was heated in a sealed tube at 95° C. for 8 h, then cooled down and evaporated. The residue was dissolved in methanolic ammonia and evaporated on silica gel under reduced pressure. Flash chromatography on silica using ethyl acetate in hexanes afforded the products as a yellow solids. In some cases additional reverse-phase HPLC purification step was necessary to obtain pure products.

General Procedure B: General Procedures for the Preparation of Ketones from Nitriles

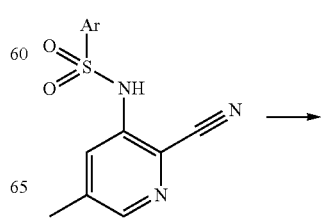

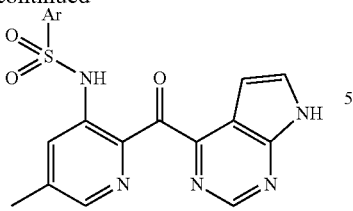

1 mmol of 4-iodo-7H-pyrrolo[2,3-d]pyrimidine was dissolved under nitrogen atmosphere in 2.8 mL THF and cooled down to −10° C. 0.50 mL of 2 M solution of phenylmagnesium chloride solution in THF was added dropwise followed by 0.50 mL of 2 M solution of isopropylmagnesium chloride solution in THF. The mixture was warmed up to room temperature and stirred for 1 h, which resulted in a complete iodine-magnesium exchange. A separate solution of 0.77 mmol of the corresponding nitrile in 1 mL THF was prepared and 0.96 mmol of 60% sodium hydride was added to it. The solutions were combined and the mixture was stirred at 45° C. for 8 hours. The reaction mixture was cooled down to room temperature, 0.52 mL of concentrated hydrochloric acid was added and the mixture was stirred at 50° C. for 0.5 hour. The solids were filtered off and washed with three 10 mL portions of THF, followed by 10 mL of diethyl ether and four portions of 1N hydrochloric acid. The solids were taken up in the mixture of aqueous sodium bicarbonate and ethyl acetate. The organic layer was passed through a pad of silica gel and evaporated under reduced pressure to give the products.

Example 1

4-Chloro-N-[5-chloro-2-(7H-pyrrolo[2,3-d]pyrimidine-4-carbonyl)-phenyl]-3-trifluoromethyl-benzenesulfonamide

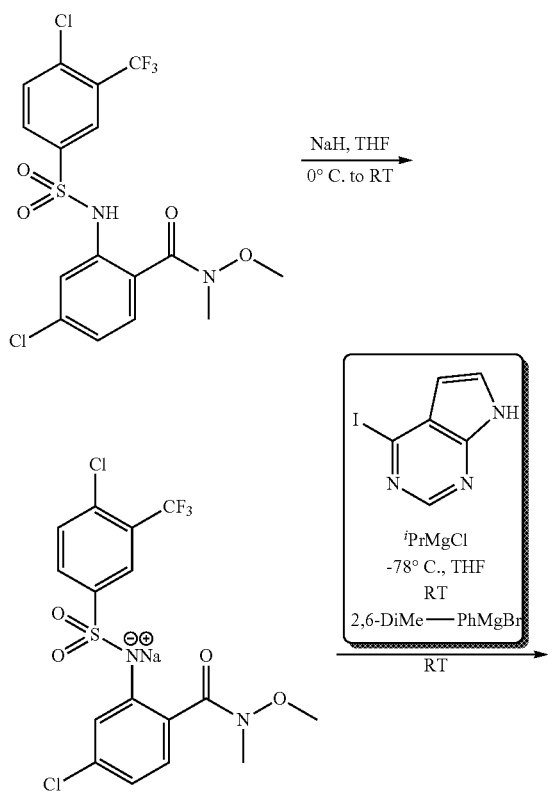

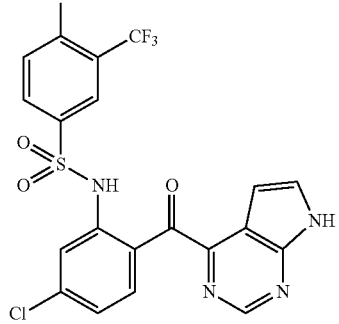

iPrMgCl (3.84 mL, 7.56 mmol; 1.97 M solution in THF) was added to iodo-pyrrolopyrimidine (0.882 g, 3.6 mmol) in THF (5 mL) at −78° C. After 15 min, it was warmed to room temperature and added 2,6-dimethylphenymagnesium bromide (2.4 mL, 2.4 mmol; 1.0 M solution in diethyl ether). To this reaction mixture at room temperature was added a sodium salt THF solution of 4-chloro-2-(4-chloro-3-trifluoromethyl-benzenesulfonylamino)-N-methoxy-N-methyl-benzamide [prepared separately by adding 60% NaH (0.144 g, 3.6 mmol) in THF (5 mL)] and stirred overnight. Saturated NH₄Cl solution (5 mL) was added and extracted with EtOAc (2×50 mL). EtOAc layer was washed with brine (25 mL), dried (Na₂SO₄) and evaporated. Crude product was purified by column purification (silica gel, 60% EtOAc in hexanes) followed by recrystallization from CH₃CN to obtain title compound (1 g) as a crystalline yellow solid in 67% yield. MS (ES) M+H expected 515.0, found 514.9. ¹H NMR (CDCl₃, 400 MHz): δ 10.75 (s, 1H), 9.92 (brs., 1H), 8.92 (d, 1H), 8.05 (s, 1H), 7.92 (dd, 1H), 7.81 (m, 2H), 7.58 (m, 1H), 7.45 (dd, 1H), 7.3 (d, 1H), 6.9 (m, 1H).

Example 2

4-Chloro-N-[2-(7H-pyrrolo[2,3-d]pyrimidine-4-carbonyl)-pyridin-3-yl]-3-trifluoromethyl-benzenesulfonamide

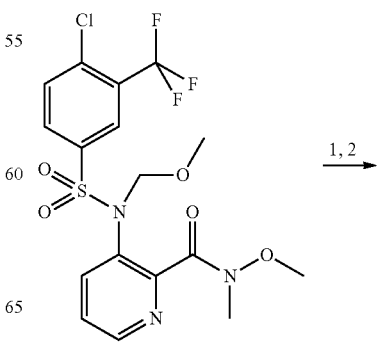

-continued

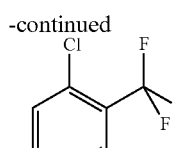

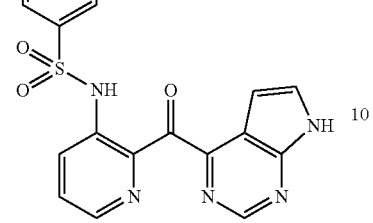

Prepared from 248 mg (0.53 mmol) of 3-[(4-chloro-3-trifluoromethyl-benzenesulfonyl)-methoxymethyl-amino]-pyridine-2-carboxylic acid methoxy-methyl-amide, 239 mg (0.58 mmol) of 90% 4-iodo-7-(2-trimethylsilanyl-ethoxymethyl)-7H-pyrrolo[2,3-d]pyrimidine dissolved in 2 mL THF with 0.32 mL of 2 M isopropylmagnesium chloride solution in THF added. All of the resulting intermediate ketone was used in the second step with 4 mL methanol and 4 mL 6N hydrochloric acid mixture to give after purification 29 mg of the final product as a yellow solid.

Example 3

4-Chloro-N-[5-chloro-2-(7-methyl-7H-pyrrolo[2,3-d]pyrimidine-4-carbonyl)-pyridin-3-yl]-3-trifluoromethyl-benzenesulfonamide

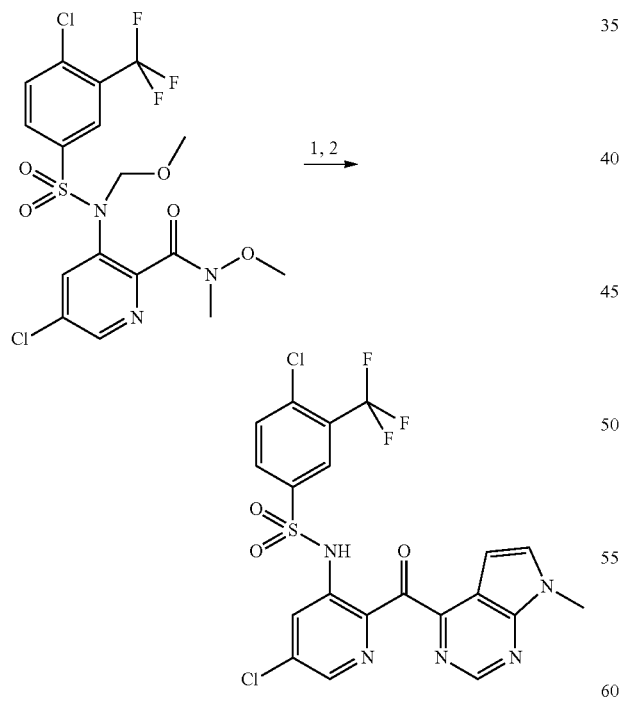

Prepared from 227 mg (0.45 mmol) of 5-chloro-3-[(4-chloro-3-trifluoromethyl-benzenesulfonyl)-methoxymethyl-amino]-pyridine-2-carboxylic acid methoxy-methyl-amide, 129 mg (0.45 mmol) of 90% 4-iodo-7-methyl-7H-pyrrolo[2,3-d]pyrimidine dissolved in 2 mL THF with 0.23 mL of 2 M isopropylmagnesium chloride solution in THF added. All of the resulting intermediate ketone (80 mg) was used in the second step with 2 mL ethanol and 2 mL 6N hydrochloric acid mixture to give after purification 45 mg of the final product as a yellow solid.

Example 4

Preparation of 4-Chloro-N-(5-(methoxymethyl)-2-(7H-pyrrolo[2,3-d]pyrimidine-4-carbonyl)pyridin-3-yl)-3-(trifluoromethyl)benzenesulfonamide

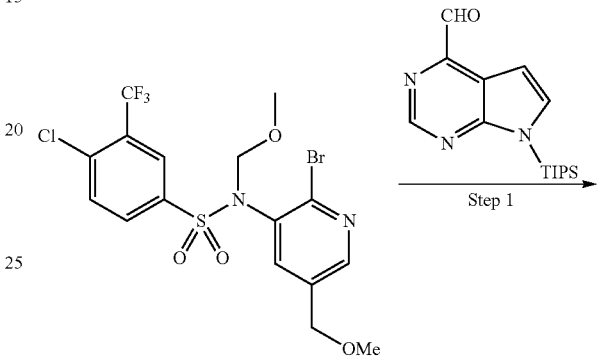

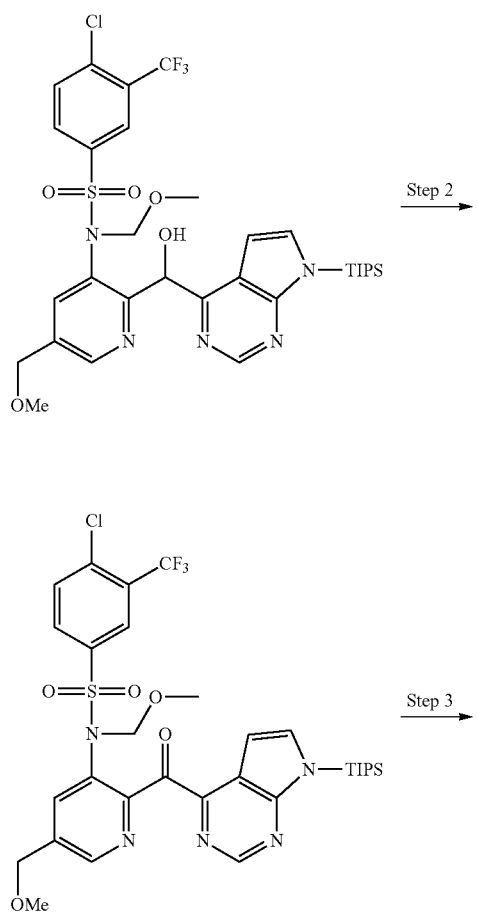

-continued

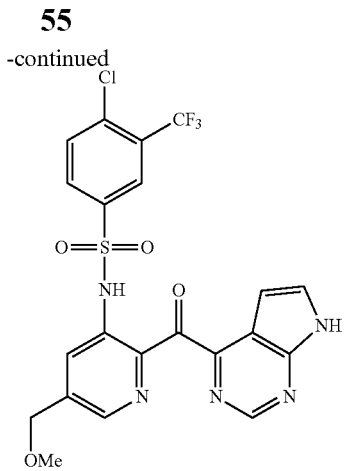

Step 1: To a solution of the bromopyridine obtained from Example 13 (step 2) (74 mg, 0.15 mmol) in THF (1 mL) at 0° C. was added isopropylmagnesium chloride (147 μL, 2.0 M in THF) dropwise. After 45 minutes, a solution of 7-(triisopropylsilyl)-7H-pyrrolo[2,3-d]pyrimidine-4-carbaldehyde (67 mg, 0.22 mmol) in THF was added. The reaction mixture was warmed up to room temperature and stirred overnight. The reaction was quenched with saturated ammonium chloride solution, and the mixture was extracted with ethyl acetate. The extracts were washed with brine, dried over MgSO$_4$ and concentrated in vacuo. The crude material was purified by flash chromatography on silica gel (33% EtOAc/hexanes). The desired product was obtained as a foaming yellow solid (45 mg, 42%). MS: (M+H)/z=728.

Step 2: The product obtained from step 1 above (45 mg, 0.062 mmol) was dissolved in 3 mL of dichloromethane. To the resultant solution was added Dess-Martin periodinane (42 mg, 1.6 equiv.) and stirred overnight at room temperature. The reaction was quenched with 10% Na$_2$S$_2$O$_3$, and the mixture was extracted with ethyl acetate. The extracts were washed with saturated NaHCO$_3$, brine, dried over MgSO$_4$ and concentrated in vacuo. The crude material was purified by flash chromatography on silica gel (33% EtOAc/hexanes). The desired product was obtained as a foaming yellow solid (35 mg, 78%). MS: (M+H)/z=726.

Step 3: The product obtained from step 2 above (35 mg, 0.048 mmol) was dissolved in 4 mL of HCl-dioxane (4.0 M) and 1 mL of water. The mixture was heated at 85° C. for 30 minutes and quenched with saturated NaHCO$_3$. The mixture was extracted with ethyl acetate. The extracts were washed with brine, dried over MgSO$_4$ and concentrated in vacuo. The crude material was purified by flash chromatography on silica gel (10% methanol/DCM). The desired product was obtained as a yellow solid (15 mg, 60%). MS: (M+H)/z=526.

Example 5

4-Chloro-N-[5-methyl-2-(7H-pyrrolo[2,3-d]pyrimidine-4-carbonyl)-pyridin-3-yl]-3-trifluoromethyl-benzenesulfonamide

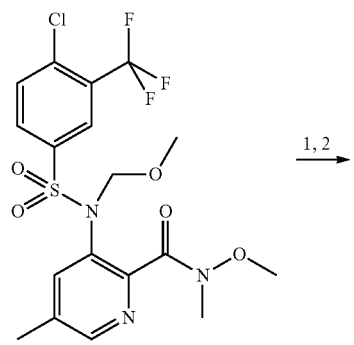

-continued

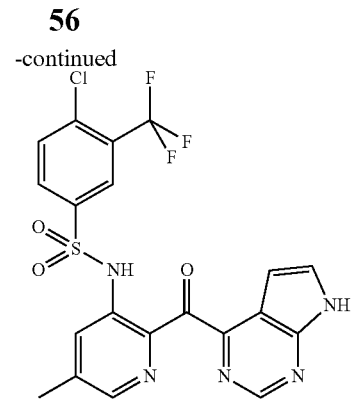

Prepared from 200 mg (0.42 mmol) of 3-[(4-chloro-3-trifluoromethyl-benzenesulfonyl)-methoxymethyl-amino]-5-methyl-pyridine-2-carboxylic acid methoxy-methyl-amide, 202 mg (0.50 mmol) of 90% 4-iodo-7-(2-trimethylsilanyl-ethoxymethyl)-7H-pyrrolo[2,3-d]pyrimidine dissolved in 2 mL THF with 0.25 mL of 2 M isopropylmagnesium chloride solution in THF added. All of the resulting intermediate ketone was used in the second step with 2 mL methanol and 2 mL 6N hydrochloric acid mixture to give after purification 29 mg of the final product as a yellow solid.

Example 6

4-Methyl-N-[5-methyl-2-(7H-pyrrolo[2,3-d]pyrimidine-4-carbonyl)-pyridin-3-yl]-3-trifluoromethyl-benzenesulfonamide

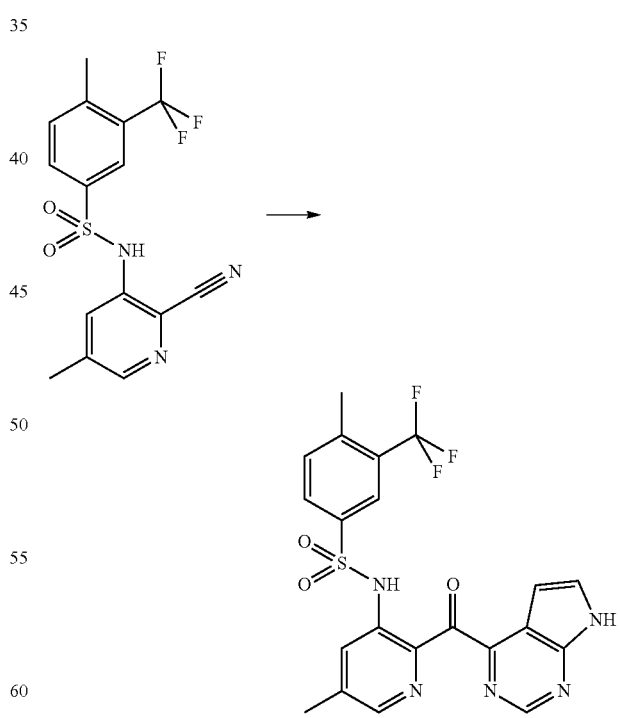

Prepared from 496 mg (1.40 mmol) of N-(2-cyano-5-methyl-pyridin-3-yl)-4-methyl-3-trifluoromethyl-benzenesulfonamide and 70 mg (1.75 mmol) of 60% sodium hydride in 2 mL THF. The Grignard solution was prepared from 467 mg (1.82 mmol) of 95% 4-iodo-7H-pyrrolo[2,3-d]pyrimidine dissolved in 5 mL THF with 0.98 mL of 2 M phenylmagnesium chloride solution in THF and 0.98 mL of 2 M isopropylmagnesium chloride solution in THF added. The reaction yielded 340 mg of the final product as a yellow solid.

Example 7

3,4-Dichloro-N-[5-methyl-2-(7H-pyrrolo[2,3-d]pyrimidine-4-carbonyl)-pyridin-3-yl]-benzenesulfonamide

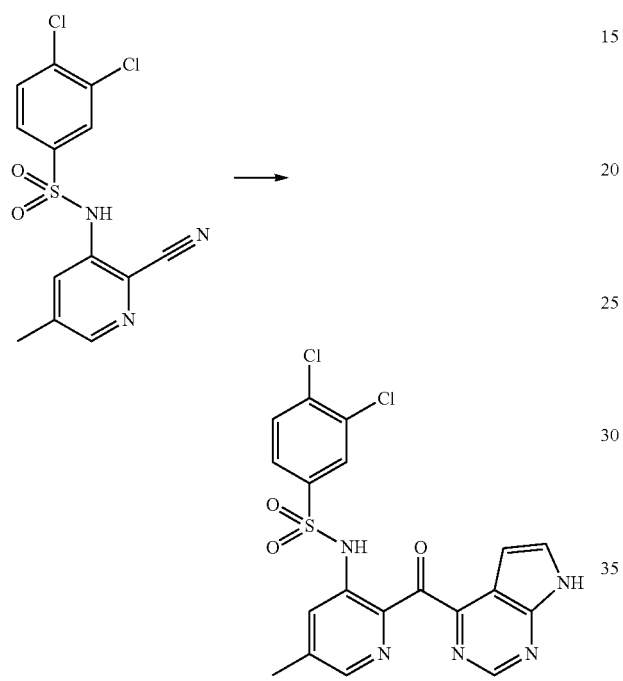

Prepared from 563 mg (1.55 mmol) of 3,4-dichloro-N-(2-cyano-5-methyl-pyridin-3-yl)-benzenesulfonamide sodium salt, 506 mg (2.01 mmol) of 97% 4-iodo-7H-pyrrolo[2,3-d]pyrimidine dissolved in 6 mL THF with 1.16 mL of 1.8 M phenylmagnesium chloride solution in THF and 1.06 mL of 2 M isopropylmagnesium chloride solution in THF added. The reaction yielded 471 mg of the final product as a yellow solid.

Example 8

Preparation of 4-Chloro-N-(5-methyl-2-(2-methyl-7H-pyrrolo[2,3-d]pyrimidine-4-carbonyl)pyridin-3-yl)-3-(trifluoromethyl)benzenesulfonamide

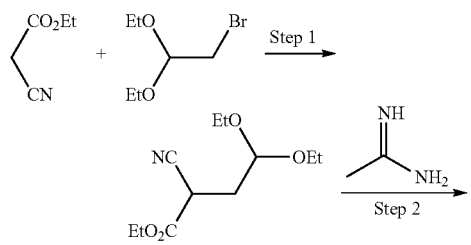

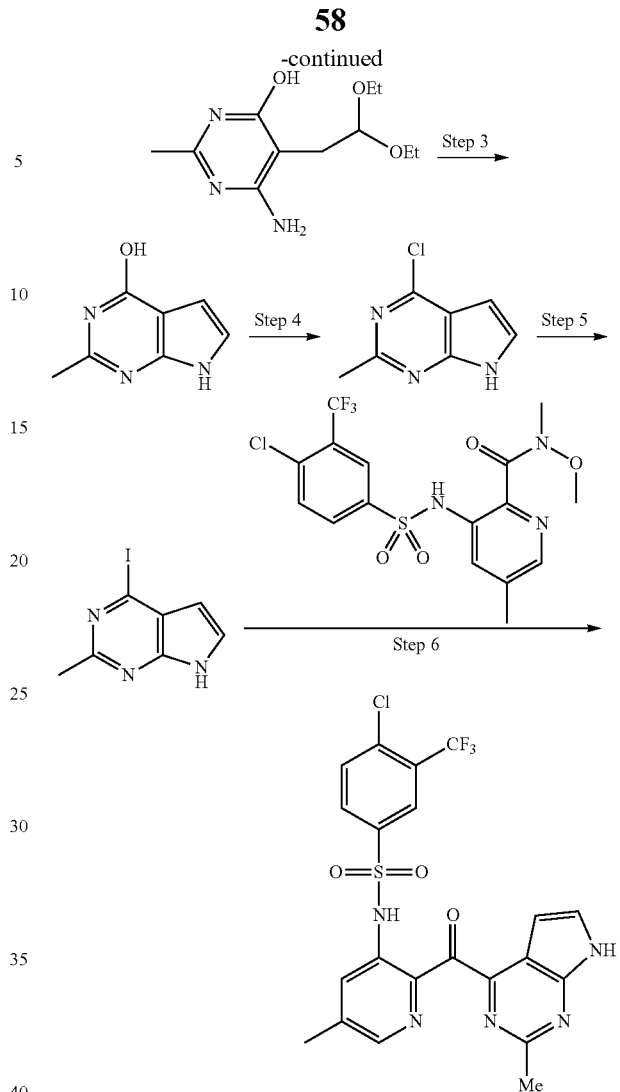

Step 1: To a suspension of NaH (60% dispersion in mineral oil, 1.62 g, 40.5 mmol) in DMF (35 mL) and benzene (12 mL) was added ethyl cyanoacetate (4.7 mL, 44.2 mmol) dropwise at −10° C. After stirring for 1 hour at room temperature, 2-bromo-1,1-diethoxyethane (5.6 mL, 0.82 equiv.) was added and the reaction mixture was heated at 100° C. for 2 hours. The reaction mixture was then cooled to room temperature and filtered. The filtrate was condensed, and water was added. The mixture was extracted with ether. The extracts were washed with brine, dried over $MgSO_4$ and concentrated in vacuo. The crude material was purified by flash chromatography on silica gel (20% EtOAc/hexanes). The desired product was obtained as colorless oil (5 g, 60%). MS: (M+Na)/z=252.

Step 2: Acetamidine hydrochloride (413 mg, 4.4 mmol) was added to a solution of sodium ethoxide (594 mg, 2.0 equiv.) in ethanol (8 mL). After stirring for half an hour at room temperature, the resultant sodium chloride was removed by filtration. The filtrate was added to ethyl 2-cyano-4,4-diethoxybutanoate (1.0 g, 4.4 mmol) and the mixture was refluxed for 5 hours. Most of the solvent was removed and the remaining slurry was dissolved in ice water, and extracted with ethyl acetate. The extracts were washed with brine, dried over $MgSO_4$ and concentrated in vacuo. The crude material was purified by flash chromatography on silica gel (100% methanol). The desired product was obtained as a red solid (421 mg, 40%). MS: (M+H)/z=242.

Step 3: The above pyrimidine (2.0 g, 8.30 mmol) was added to a solution of sulfuric acid (0.9 mL) in 50 mL of ethanol and refluxed for 2 hours. After cooling down to room temperature, the mixture was concentrated in vacuo. The crude material (soluble in water) was used directly for the next step. MS: (M+H)/z=150.

Step 4: A suspension of 90 mg (0.60 mmol) of the above hydroxypyrrolopyrimidine in 2 mL of phosphorous oxychloride was refluxed for 2 hours. The excess phosphorous oxychloride was removed and the residue was quenched carefully with ice. The mixture was extracted with ethyl acetate. The extracts were washed with brine, dried over MgSO$_4$ and concentrated in vacuo. The crude material was purified by flash chromatography on silica gel (10% methanol/DCM). The desired product was obtained as a colorless solid (86 mg, 85%). MS: (M+H)/z=168.

Step 5: The above chloropyrrolopyrimidine (40 mg, 0.24 mmol) was added to an aqueous solution of hydroiodic acid (57 wt. % in water, 1.5 mL) and the mixture was heated at 35° C. overnight. After cooling down to room temperature, a solution of hydroxylamine was added and the mixture was extracted with ethyl acetate. The extracts were washed with brine, dried over MgSO$_4$ and concentrated in vacuo. The desired product was obtained as a brown solid (50 mg, 80%). MS: (M+H)/z=260.

Step 6: To a solution of 3-(4-chloro-3-(trifluoromethyl) phenylsulfonamido)-N-methoxy-N,5-dimethylpicolinamide (56 mg, 0.13 mmol) in THF (1 mL) at 0° C. was added NaH (60% dispersion in mineral oil, 6 mg, 1.2 equiv.). The reaction was then warmed up to room temperature and stirred for 0.5 hour.

In a separate flask was charged the above iodopyrrolopyrimidine (40 mg, 1.2 equiv.) in 0.5 mL of THF. The solution was cooled to −78° C., and a solution of isopropylmagnesium chloride in THF (2.0 M, 167 µL) was added dropwise. The reaction mixture was then warmed up to room temperature and a solution of 2,6-dimethylphenyl magnesium bromide solution (1.0 M, 167 µL, 1.3 equiv.) in THF was added. After stirring for half an hour, the mixture was added to the above Weinreb amide solution and the reaction was stirred for an additional hour before quenching with saturated ammonium chloride solution. The mixture was extracted with ethyl acetate. The extracts were washed with brine, dried over MgSO$_4$ and concentrated in vacuo. The crude material was purified by flash chromatography on silica gel (33% EtOAc/hexanes). The desired product was obtained as a yellow solid (31 mg, 40%). MS: (M+H)/z=510.

Example 9

4-Chloro-N-[5-chloro-2-(9H-purine-6-carbonyl)-pyridin-3-yl]-3-trifluoromethyl-benzenesulfonamide

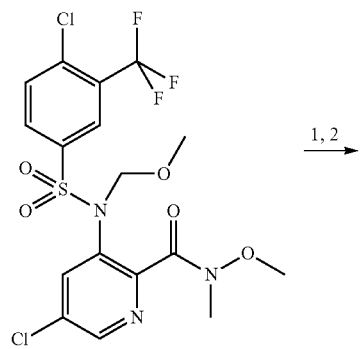

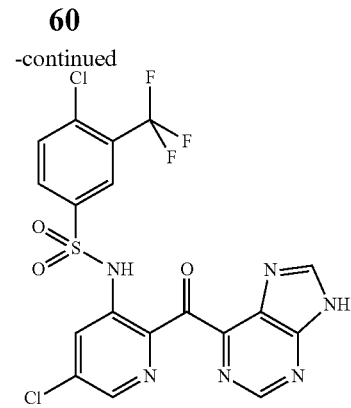

Prepared from 256 mg (0.51 mmol) of 5-chloro-3-[(4-chloro-3-trifluoromethyl-benzenesulfonyl)-methoxymethyl-amino]-pyridine-2-carboxylic acid methoxy-methyl-amide, 191 mg (0.51 mmol) of 6-iodo-9-(2-trimethylsilanyl-ethoxymethyl)-9H-purine dissolved in 2 mL THF with 0.25 mL of 2 M isopropylmagnesium chloride solution in THF added. All of the resulting intermediate ketone was used in the second step with 1 mL methanol and 1 mL 6N hydrochloric acid mixture to give after purification 2.05 mg of the final product as a yellow solid.

Example 10

4-Chloro-N-[5-chloro-2-(7H-pyrrolo[2,3-d]pyrimidine-4-carbonyl)-pyridin-3-yl]-3-trifluoromethyl-benzenesulfonamide

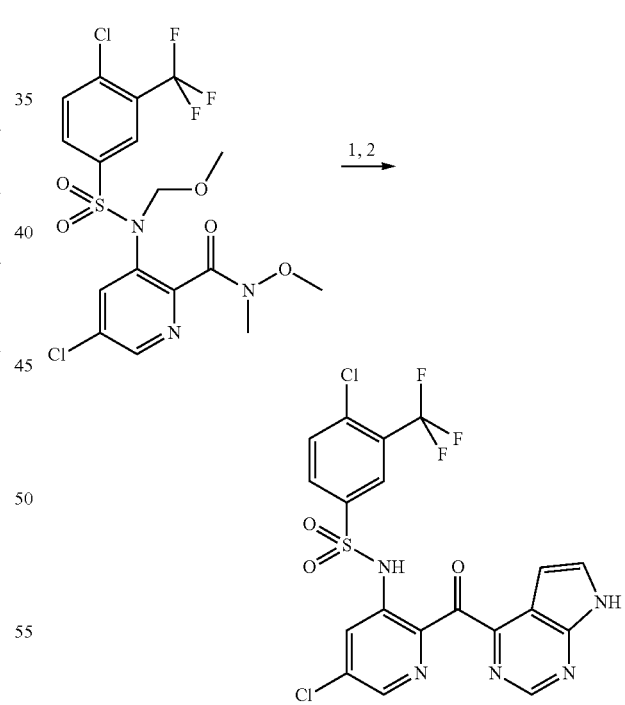

Prepared from 259 mg (0.52 mmol) of 5-chloro-3-[(4-chloro-3-trifluoromethyl-benzenesulfonyl)-methoxymethyl-amino]-pyridine-2-carboxylic acid methoxy-methyl-amide, 213 mg (0.52 mmol) of 90% 4-iodo-7-(2-trimethylsilanyl-ethoxymethyl)-7H-pyrrolo[2,3-d]pyrimidine dissolved in 2 mL THF with 0.26 mL of 2 M isopropylmagnesium chloride solution in THF added. All of the resulting intermediate ketone was used in the second step with 2 mL methanol and 2 mL 6N hydrochloric acid mixture to give after purification 40 mg of the final product as a yellow solid.

Example 11

4-Chloro-N-[5-chloro-2-(1H-pyrrolo[2,3-c]pyridine-4-carbonyl)-pyridin-3-yl]-3-trifluoromethyl-benzenesulfonamide

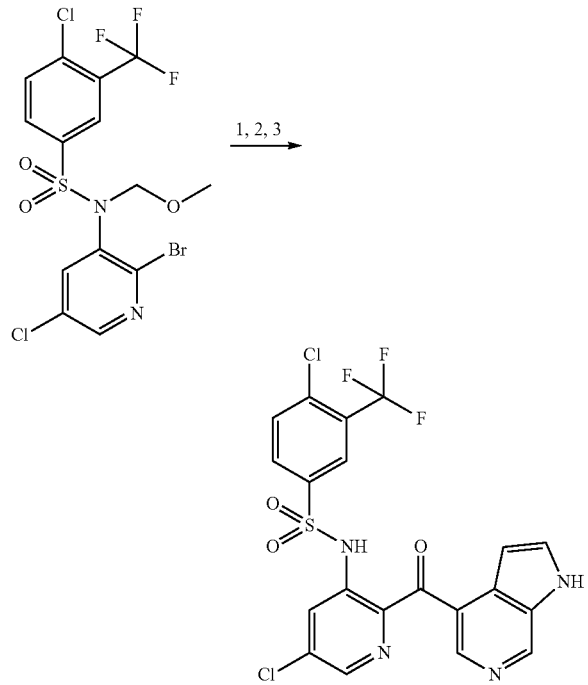 [SMILES: COCN(c1cc(Cl)cnc1Br)S(=O)(=O)c1ccc(Cl)c(C(F)(F)F)c1 ; O=C(c1ncc(Cl)cc1NS(=O)(=O)c1ccc(Cl)c(C(F)(F)F)c1)c1cncc2[nH]ccc12]

Prepared from 494 mg (1.00 mmol) of N-(2-bromo-5-chloro-pyridin-3-yl)-4-chloro-N-methoxymethyl-3-trifluoromethyl-benzenesulfonamide dissolved in 2 mL THF, 1.05 mL of 2 M isopropylmagnesium chloride solution in THF. 146 mg (1.00 mmol) of 1H-pyrrolo[2,3-c]pyridine-4-carbaldehyde was dissolved in 1 mL THF and treated sequentially at room temperature with 44 mg (1.1 mmol) of 60% sodium hydride and 177 uL (1 mmol) of trimethylsilylethoxymethyl chloride prior to addition to the Grignard reagent solution. Yield: 40 mg of the intermediate alcohol. All of it was used in the second step with 74 mg of Dess-Martin periodinane dissolved in 1 mL of DCM. The 31 mg of the resulting protected ketone was subjected to step 3 in 2 mL methanol and 2 mL 6N hydrochloric acid mixture at 100° C. to give after purification 17 mg of the final product as a yellow solid. LC-MSD, m/z for $C_{20}H_{11}Cl_2F_3N_4O_3S$ [M+H]+=514.9, 516.9; HPLC retention time: 2.3 minutes.

Example 12

3,4-Dichloro-N-[5-methyl-2-(1H-pyrrolo[2,3-c]pyridine-4-carbonyl)-pyridin-3-yl]-benzenesulfonamide

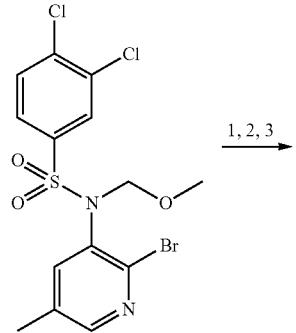

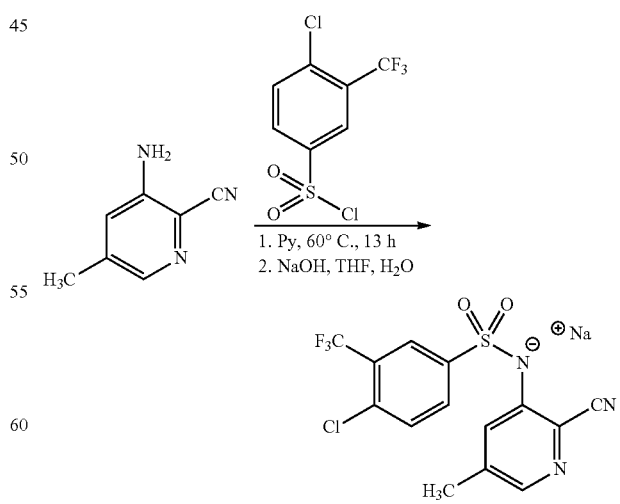

Prepared from 204 mg (0.464 mmol) of N-(2-bromo-5-methyl-pyridin-3-yl)-3,4-dichloro-N-methoxymethyl-benzenesulfonamide dissolved in 1 mL THF, 0.49 mL of 2 M isopropylmagnesium chloride solution in THF. 75 mg (0.510 mmol) of 1H-pyrrolo[2,3-c]pyridine-4-carbaldehyde was dissolved in 1 mL THF and treated at room temperature with 22 mg (0.557 mmol) of 60% sodium hydride prior to addition to the Grignard reagent solution. All of the intermediate alcohol was used in the second step with 300 mg of Dess-Martin periodinane dissolved in 2 mL of DCM. The resulting protected ketone was subjected to step 3 in 6 mL methanol and 6 mL 6N hydrochloric acid mixture at 90° C. to give after purification 22 mg of the final product as a yellow solid. LC-MSD, m/z for $C_{20}H_{14}Cl_2N_4O_3S$ [M+H]+=460.9, 462.9; HPLC retention time: 2.3 minutes.

Example 13

4-Chloro-N-[5-methyl-2-(7H-pyrrolo[2,3-d]pyrimidine-4-carbonyl)-pyridin-3-yl]-3-trifluoromethyl-benzenesulfonamide sodium salt (a) Synthesis of 3-(4-chloro-3-trifluoromethyl-benzenesulfonylamino)-5-methyl-pyridine-2-carbonitrile sodium salt

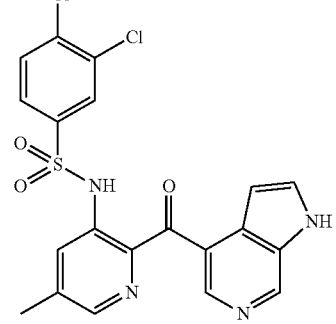

To a solution of 3-amino-2-cyano-5-methylpyridine (83 g, 0.619 mol) in pyridine (625 mL) was added 4-chloro-3-trifluoromethylbenzenesulfonyl chloride (207 g, 0.742 mol) in one portion and the resulting reaction mixture stirred at 60° C. over night (13 hours). Pyridine was removed in vacuo, THF (350 mL) was added and removed in vacuo. To the obtained dark brown solid was added THF (650 mL), H$_2$O (550 mL), followed by NaOH (75 g, 1.88 mol) slowly at 0° C. (in five portions) over 20 minutes. The resulting solution was stirred at 0° C. for another 30 minutes. After removing THF in vacuo (~650 mL), H$_2$O (50 mL) was added and the suspension was heated to dissolve all the solids. After cooling in an ice bath for 2 hours, the resulting solid was collected by filtration, washed with ice water (100 mL×3) and dried in a 110° C. vacuum oven for 24 hours to afford the title compound (190 g, 77%) as white needles: mp. 287.0-288.5° C. $^1$H NMR (400 MHz, d6-DMSO) δ 8.05 (1H, s), 7.96 (d, 1H), 7.76 (dd, 1H), 7.63 (s, 1H), 7.40 (s, 1H), 2.12 (s, 3H). MS (ES) M+H expect 375.9, found 375.9. Mother liquor was concentrated (~⅔ volume) in vacuo to afford another 30 g of the title compound after washing and drying, total yield 89%.

(b) 4-Chloro-N-[5-methyl-2-(7H-pyrrolo[2,3-d]pyrimidine-4-carbonyl)-pyridin-3-yl]-3-trifluoromethyl-benzenesulfonamide

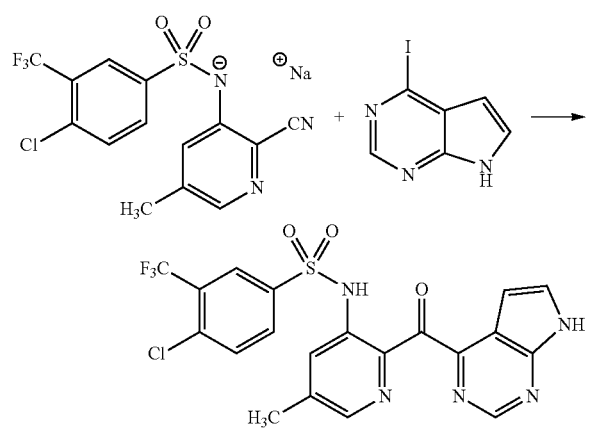

4-Iodopyrrolo[2,3-d]pyrimidine (2b, 50.3 g, 95.5% purity, 196 mmol) was dissolved/suspended in 0.64 L of anhydrous THF in a three-necked 2 L round bottom flask under nitrogen atmosphere, equipped with a mechanical stirrer and a thermometer. The solution was cooled down to −15° C. in a dry ice-acetone bath and 206 mL of a 1.0 M o-tolylmagnesium chloride THF solution (1.05 equiv.) was added slowly, so the internal temperature would not exceed −10° C. During the addition all of the solids dissolved. The cooling bath was removed and 104 mL of a 1.95 M isopropylmagnesium chloride THF solution (1.03 equiv.) was added over a period of 3 minutes. During the addition tan solids precipitate; the stirring should be vigorous to avoid clumping. The resulting solution was warmed rapidly to room temperature using warm water bath. To this suspension, 59.9 g of the nitrile sodium salt (19, 0.77 equiv.) in 120 mL dry THF was added and the resulting mixture was stirred at 45° C. for 16 hours. The mixture was cooled down in an ice bath and 101 mL of 36% aqueous HCl was added dropwise, so the internal temperature would not exceed 30° C., while vigorously stirred. Yellow solids precipitated and the entire thick suspension was mechanically stirred for 30 minutes at 50° C. (yellow solids become orange), cooled down to room temperature and then filtered. The solids were washed with 700 mL of THF, followed by 700 mL of diethyl ether, followed by two 1 L portions of 1 M aqueous HCl. The resulting wet orange solid was taken up in a mixture of 0.9 L ethyl acetate, 0.5 L water and 50 g of sodium bicarbonate and stirred until completely dissolved. The solution was filtered through a pad of CELITE® and the layers were separated. The aqueous layer was extracted with 50 mL of ethyl acetate. The combined organic layers were filtered through a pad of 200 g of silica gel, followed by washing silica with additional 0.8 L of ethyl acetate. The solution was concentrated down in vacuo to yield 56.5 g of the product as a yellow solid (contains 2 wt % of ethyl acetate, yield 74%).

(c) 4-Chloro-N-[5-methyl-2-(7H-pyrrolo[2,3-d]pyrimidine-4-carbonyl)-pyridin-3-yl]-3-trifluoromethyl-benzenesulfonamide sodium salt 4-Chloro-N-[5-methyl-2-(7H-pyrrolo[2,3-d]pyrimidine-4-carbonyl)-pyridin-3-yl]-3-trifluoromethyl-benzene-sulfonamide (6.85 g, 13.8 mmol) was suspended in 103 mL of iso-propyl alcohol and brought to reflux under the atmosphere of nitrogen. The suspension was treated with 1.30 mL of 10.6 N aqueous sodium hydroxide (1 equiv.) dropwise with stirring, whereupon all the solids dissolve. The mixture was let to cool down to room temperature and seeded, then further cooled down in an ice bath. The solid is filtered off and washed with 35 mL iso-propyl alcohol, followed by overnight drying on vacuum at 80° C. Yield: 6.12 g (86%). IPA content is 800 ppm (determined by $^1$H NMR).

Example 14

XPRD of the Compound of Example 13

The material from Example 13 was subjected to x-ray powder diffraction (XRPD) analysis. The analysis was performed using a Shimadzu XRD-6000 X-ray powder diffractometer using Cu Kα radiation. The instrument is equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected by NaI scintillation detector. A θ-2θ continuous scan at 3°/min (0.4 sec/0.02° step) from 2.5 to 40° 2θ value was used. A silicon standard was analyzed to check the instrument alignment. Data were collected and analyzed using XRD-6100/7000 v.5.0. The XPRD scan is depicted in FIG. 1. The 2-theta values are reported in Table 3. The crystalline form of the compound of Example 13 is designated as Form A.

Peak list (2θ°) and intensities (CPS) observed in the XRPD of crystalline compound of example 13. Peak intensity may vary depending on the particle size and morphology.

TABLE 3

| Angle 2θ° | Intensity (CPS) |
|---|---|
| 6.9 | 635 |
| 7.7 | 1555 |
| 10.6 | 340 |
| 11.3 | 250 |
| 11.8 | 125 |
| 12.5 | 165 |
| 13.7 | 255 |
| 15.1 | 300 |
| 15.3 | 305 |
| 16.1 | 490 |
| 16.9 | 290 |
| 17.3 | 485 |

TABLE 3-continued

| Angle 2θ° | Intensity (CPS) |
|---|---|
| 18.2 | 195 |
| 18.5 | 190 |
| 19.5 | 250 |
| 20.0 | 1485 |
| 21.6 | 510 |
| 21.8 | 340 |
| 22.6 | 680 |
| 24.3 | 635 |
| 24.7 | 615 |
| 25.1 | 630 |
| 25.6 | 255 |
| 26.3 | 255 |
| 27.5 | 490 |
| 28.5 | 605 |
| 28.8 | 345 |
| 29.3 | 240 |
| 31.4 | 315 |
| 32.4 | 465 |

Comparative Example 1

4-chloro-N-(5-methyl-2-(1H-pyrazolo[3,4-b]pyridine-4-carbonyl)pyridin-3-yl)-3-(trifluoromethyl)benzenesulfonamide

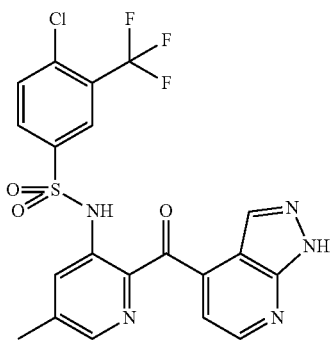 [SMILES: Cc1cnc(C(=O)c2ccnc3[nH]ncc23)c(NS(=O)(=O)c2ccc(Cl)c(C(F)(F)F)c2)c1]

This compound can be prepared as described in US Publication No. 2007-0037794A1.

The compounds of Examples 1-12 each have an $IC_{50}$ of less than 1000 nM in the following CCR2 chemotaxis assay. Compound 5 has an average $IC_{50}$ of approximately 5 nM in this assay.

Example of In Vitro Assay

Reagents

THP-1 cells were obtained from the American Type Culture Collection (Manassas, Va.) and cultured in RPMI tissue culture medium supplemented with 10% fetal calf serum (FCS) in a humidified 5% $CO_2$ incubator at 37° C. Recombinant human chemokine proteins MCP-1 were obtained from R&D Systems (Minneapolis, Min.). $^{125}$I-labeled MCP-1 protein was obtained from Amersham (Piscataway, N.J.). ChemoTX® chemotaxis microchambers were purchased from Neuro Probe (Gaithersburg, Md.). CyQUANT® cell proliferation kits were purchased from Molecular Probes (Eugene, Oreg.). Calcium indicator dye Fluo-4 AM was purchased from Molecular Devices (Mountain View, Calif.).

Conventional Migration Assay

Conventional migration assay was used to determine the efficacy of potential receptor antagonists in blocking migration mediated through chemokines (such as CCR2). This assay was routinely performed using the ChemoTX® microchamber system with a 5-μm pore-sized polycarbonate membrane. To begin such an assay, chemokine expressing cells (such as THP-1 cells for CCR2 assay) were harvested by centrifugation of cell suspension at 1000 RPM on a GS-6R Beckman centrifuge. The cell pellet was resuspended in chemotaxis buffer (HBSS with 0.1% BSA) at $10\times10^6$ cells/mL for CCR2 assay. Test compounds at desired concentrations were prepared from 10 mM stock solutions by serial dilutions in chemotaxis buffer. An equal volume of cells and compounds were mixed and incubated at room temperature for 15 minutes. Afterwards, 20 μL of the mixture was transferred onto the porous membrane of a migration microchamber, with 29 μL of chemokine ligand (0.1 nM chemokine MCP-1 protein for CCR2 assay) placed at the lower chamber. Following an incubation at 37° C. (90-minute for CCR2), during which cells migrated against the chemokine gradient, the assay was terminated by removing the cell drops from atop the filter. To quantify cells migrated across the membrane, 5 μL of 7× CyQUANT® solution was added to each well in the lower chamber, and the fluorescence signal measured on a Spectrafluor Plus fluorescence plate reader (TECAN, Durham, N.C.). The degree of inhibition was determined by comparing migration signals between compound-treated and untreated cells. $IC_{50}$ calculation was further performed by non-linear squares regression analysis using Graphpad Prism (Graphpad Software, San Diego, Calif.).

Pharmacokinetics

The pharmacokinetics (PK) and oral bioavailability of the compound of Example 5 were determined in the beagle dog.

Following an i.v. bolus administration of 1 mg/kg of compound 5 (free base) in 31.6% N,N dimethylacetamide/36.8% water/31.6% propylene glycol to male beagle dogs (n=2), blood samples were collected at the following times: Predose, 2, 5, 15, 30 minutes, 1, 2, 4, 8, 12, and 24 hours post dosing. Following an oral administration of 5 mg/kg of the compound of Example 5 in 1% methocel to male beagle dogs (n=2), blood samples were collected at the following times: Predose, 5, 15, 30 minutes, and 1, 2, 4, 8, 12, and 24 hours post dosing.

The intact compound of Example 5 was extracted from the plasma samples using 3% formic acid/acteonitrile and measured using an LC-MS/MS method. PK parameters were determined by non-compartmental analysis. Animals were observed for signs of ill health and mortality. The compound of Example 5 was well tolerated by the beagle dogs with no gross signs of ill health or mortality.

Following i.v. administration of the compound of Example 5, the plasma concentrations of intact compound 5 declined mono-exponentially with a mean terminal elimination half-life $t_{1/2}$ of 4.7 hours. The compound of Example 5 was cleared from the plasma very slowly at 0.2 mL/min/kg (<1% of dog liver blood flow) and showed a very low volume of distribution ($V_{ss}$) of 0.1 L/kg. The mean residence time ($MRT_{iv}$) was estimated to be 7.2 hours. Following oral administration, the compound of Example 5 was rapidly absorbed with a mean peak plasma concentration ($C_{max}$) of 44.4 μg/mL (about 59.5 μM) achieved after 1.5 hour ($T_{max}$). The compound was well absorbed, with an oral bioavailability of about 100%.

The compound of Example 5 displayed an excellent i.v. and oral PK profile. Following i.v. dosing, it showed a very low clearance in the beagle dog (less than 1% of liver blood flow) and a long mean residence time (about 7 hours). Compound 5 was also rapidly and well absorbed orally, with a bioavailability about 100%.

CYP2C9 and CYP3A4 Inhibition Assays

The test compounds were incubated with pooled human liver microsomes at 37° C. in the presence of NADPH and appropriate concentrations of substrates specific for CYP2C9 and 3A4. The final assay concentrations of human liver microsomes and substrates, the initial substrate stock solution concentrations in DMSO, and the times used for the various isozyme incubations are summarized in Table 4. The final assay concentrations of the positive inhibitor controls in each isozyme assay are listed in Table 5.

TABLE 4

Incubation Concentrations

| CYP450 | Protein Conc. [mg/mL] | Substrate | Substrate Conc. [µM] | Incubation Time [min] |
|---|---|---|---|---|
| 2C9 | 0.05 | Diclofenac | 10 | 10 |
| 3A4 | 0.05 | Midazolam | 3 | 10 |
|  | 0.05 | Testosterone | 100 | 30 |

TABLE 5

Conditions for Controls

| CYP450 | Substrate | Control | Final Incubation Control Concentration [µM] | | | | | | |
|---|---|---|---|---|---|---|---|---|---|
| 2C9 | Diclofenac | Sulfaphenazole | 50 | 17 | 5.6 | 1.9 | 0.62 | 0.2 | 0.069 |
| 3A4 | Midazolam | Ketoconazole | 1 | 0.33 | 0.11 | 0.037 | 0.012 | 0.0041 | 0.0014 |
|  | Testosterone | Ketoconazole | 1 | 0.33 | 0.11 | 0.037 | 0.012 | 0.0041 | 0.0014 |

Incubation

120 µL of a mixture of human liver microsomes (HLM) in 50 mM potassium phosphate/5 mM $MgCl_2$ buffer was added into all wells of row A in a 96-well plate. The concentration of microsomal protein was 2-fold the intended protein concentration for the particular isozyme assay recorded in Table 4. In addition, 80 µL of this human liver microsome preparation spiked with 1% DMSO was dispensed into all wells of rows B through H.

1.2 µL of each individual test compound in DMSO (10 mM) was added to the first 10 wells of row A (5 different test compounds each in duplicate). Additionally, 1.2 µL of the DMSO stock of the control inhibitor for the isozyme under study was added into the final two wells of row A to give a concentration two-fold above the highest final concentration. (See Table 5 for the final control inhibitor concentrations)

Three-fold serial dilutions were performed by taking 40 µL from each solution in wells of row A (wells 1-12, both compounds and controls) and diluting into the wells of row B. After thorough mixing, 40 µL from each solution in wells of row B were dispensed with a multichannel pipette (12 channels) into the wells of row C and the controls and test compounds hence further diluted. This process was repeated for rows D through G. After mixing, 40 µL was removed and discarded from the wells of row G.

This procedure resulted in 80 uL of solution being present in all wells of all rows A through H, with protein concentrations being twice the final intended concentrations in all wells of rows, and test compound and control concentration being twice the final intended concentrations in rows A through G. Row H was not spiked with a test compound or positive control.

The plate was covered and pre-incubated for 10 minutes in a 37° C. incubator. The reaction was initiated by adding 80 µL of a solution of the substrate for the isozyme under investigation in 50 mM potassium phosphate/5 mM $MgCl_2$ buffer solution with 4 mM NADPH present, at a substrate concentration two-fold the intended final substrate concentrations using a multichannel pipette. The substrate solution was added to all wells rows A to H excluding wells 95 and 96 (microsomal blanks). The substrate solutions were prepared from various DMSO substrate stock solutions prepared at concentrations also noted in Table 4.

This procedure yielded the final protein and substrate concentrations listed in Table 4, the final control concentrations listed in Table 5, and test compound concentrations of 50 µM, 16.7 µM, 5.6 µM, 1.9 µM, 618 nM, 206 nM and 69 nM for each individual test compound.

The plate was covered and incubated at 37° C. for the time listed in Table 4 for the isoform under investigation. The reaction was stopped by dispensing 120 µL of internal standard (200 ng/mL CCX915-6A) in acetonitrile to all wells. 80 µL of the specific substrate/NADPH solution described above was added into the well 95 and 96 after stopping the reaction to provide the blank. The plate was vortexed for 10 min and spun in a centrifuge at 4,450 rpm and 4° C. for 10 min. With a multichannel pipette, 80 µL of the supernatant was transferred into a sample plate wells containing 80 µL of 0.1% formic acid/water and mixed well for analysis on LC-MS/MS as described in sections E and F.

Analytical Method

Samples were analyzed by the LC-MS/MS method. Each metabolite (Table 6) derived from the particular substrate for each different CYP450 isoform was monitored.

HPLC Conditions for Substrates

Instrument: Shimadzu, equipped with liquid chromatography system LC-10AD VP.

CYP2C9 and CYP3A4 (Midazolam) Inhibition

Column: Waters, Sunfire C18, 3 u, 2.1×50 mm

Mobile Phases: A: 0.1% Formic Acid in Water
B: 0.1% Formic Acid in Acetonitrile

Gradient Program: for CYP2C9 and CYP3A4 (Midazolam)

| Time [min] | Solvent A | Solvent B |
|---|---|---|
| 0.0-0.2 | 95 | 5 |
| 0.3-1.0 | 5 | 95 |
| 1.0-3.0 | 95 | 5 |

Flow rate: 300 µL/min

Inj. Vol: 10 µL

Run Time: 3 min for CYP2C9, 3A4 (Midazolam). Retention time for analyte is 1.03 min for 2C9 (4'-Hydroxy-diclofenac) and 0.87 min for 3A4 (1'-hydroxyl midazolam)

CYP3A4 inhibition (Testosterone)

Column: Waters, Sunfire C18, 3 u, 2.1×50 mm

Mobile Phases: A: 0.1% Formic Acid in Water
B: 0.1% Formic Acid in Acetonitrile

Gradient Program: for CYP3A4 (Testosterone)

| Time [min] | Solvent A | Solvent B |
|---|---|---|
| 0.0-1.5 | 95 | 5 |
| 1.5-3.0 | 5 | 95 |
| 3.0-4.0 | 95 | 5 |

Flow rate: 300 µL/min
Inj. Vol: 20 µL
Run Time: 4.0 min for CYP3A4 (Testosterone). Retention time for analyte (6-β-hydroxy testosterone) is 1.35 min for 3A4 (Testosterone).

Mass Spectrometer Conditions
Instrument: Applied Biosystems (Foster City, Calif.) API 3000 and 4000 Q-TRAP mass spectrometer
Interface: Electrospray ("Turbo Ion Spray"), positive Ionization
Mode: Multiple Reaction Monitoring (MRM)

TABLE 6

Mass transitions for metabolites and HPLC retention times

| CYP450 Isoform | Substrate | Metabolite | Transition | RT time [min] substrate |
|---|---|---|---|---|
| 2C9 | Diclofenac | 4'-Hydroxy-diclofenac | 312.10/230.97 | 2.2 |
| 3A4 | Midazolam | 1'-hydroxyl midazolam | 341.98/323.92 | 2.23 |
|  | Testosterone | 6-β-hydroxy testosterone | 305.13/269.28 | 2.1 |

*analyzed on API 4000 QTRAP mass spectrometer

Calculation OF $IC_{50}$

The peak areas of the metabolites were obtained by automatic integration of the chromatograms using Analyst® 1.4.1 software (Applied Biosystems, Foster City, Calif.).

$$\text{Inhibition} = 100 - ((AUC_{test} - AUC_{blank})/(AUC_{control} - AUC_{blank}) \times 100) \quad \text{Eq. 1}$$

$AUC_{test}$, $AUC_{control}$ and $AUC_{blank}$ are the peak area count for the metabolite of the control in the presence of test article or positive inhibitor, the peak area count of metabolite of the control without test article, and peak area count observed in the microsome blank, respectively. The percent inhibition was plotted against the test article concentration using Excel (Microsoft). The $IC_{50}$ values were calculated using a 4-parameter fit in XLFit™ (IDBS Lid, Guildford, UK). The $IC_{50}$ values of the selected compounds are displayed below.

Pharmacokinetic Evaluation of Selected Compounds in Sprague-Dawley Rats

An intravenous/oral pharmacokinetic study with the selected compounds was conducted in male Sprague-Dawley rats weighing between 0.24 and 0.36 kg. Blood samples were collected at predetermined time points and the corresponding plasma samples from the animals were analyzed for test compound concentrations using an LC-MS/MS method. The pharmacokinetic parameters were derived from the plasma concentration versus time curve.

For LC-MS/MS analysis, a 1 mg/mL stock solution of test compound in acetonitrile was prepared, and working stock solutions prepared in 50% methanol/water were used to prepare analytical standards and QC samples.

Platelet-poor male Sprague-Dawley rat plasma with sodium EDTA as anticoagulant was obtained from Bioreclamation, Inc. (East Meadow, N.Y.) and used for the preparation of the analytical standards as well as for serial dilutions of the selected samples.

Animals

Eight animals weighing between 0.24 and 0.36 kg were used for this study. Two animals were used for the i.v. dosing, whereas the later six were for oral dosing.

Dosing and Blood Draws

For i.v. dosing, a solution formulation of test compound was prepared in propylene glycol/N,N-dimethyl acetamide/EtOH (31.6/31.6/36.8) at 1 mg/mL and each animal received 1 mL/kg. For oral dosing, a the test compounds were suspended in 1% HPMC at 0.5 mg/mL and each animal received 10 mL/kg.

Animals were fasted overnight and examined prior to dosing and at the conclusion of the study. For intravenous dosing, blood (0.2 mL) was drawn at pre-dose and at 2, 5, 10, 15, and 30 minutes, 1, 2, 4, 6, and 8 hours post-dose. For oral dosing, blood (0.2 mL) was drawn at pre-dose and at 5, 15, and 30 minutes, 1, 1.5, 2, 4, 6, 8, and 24 hours post-dose. Blood was sampled from canulated animals and then placed into chilled polypropylene tubes containing sodium EDTA as the anticoagulant and kept on ice until centrifugation. Plasma was collected through centrifugation (Eppendorf Centriguge 5417R) at 12000 rpm and 4° C. for 6 minutes and stored at −20° C. until analysis.

Analytical Method

Plasma samples (50 µL) were extracted with 150 µL acetonitrile containing the internal standard on a linear shaker for 10 min. The samples were centrifuged at 4450 RPM for 10 min at 4° C. (Allegra X-15R centrifuge, Beckman Coulter, Inc., Fullerton, Calif.). 80 µL of the resultant supernatant was transferred into new plate wells containing 80 µL 0.1% formic acidin water and thoroughly mixed.

Extracted samples prepared using the above procedure were separated by high-performance liquid chromatography using a Shimadzu (Kyoto, Japan) system equipped with two LC-10 AD pumps and a C-18 column (Waters Sunfire, 2×30 mm, 3.5 µm; 10 µl injection) using a mobile phase consisting of (A) 0.1% formic acidin water and (B) 0.1% formic acidin acetonitrile, at a flow rate of 0.35 mL/min. The gradient was 0-1.5 min 5% B, 1.5-2.5 min 5-95% B, 2.5-2.7 min 95% to 5% B, and 2.7-4.0 min 5% B. The HPLC elute was routed into an Applied Biosystems (Foster City, Calif.) Sciex API 3000 triple quadrupole mass spectrometer, operating in the Turbo Ionspray positive ionization MS/MS mode for analysis. Acquisition and integration were performed with Applied Biosystems-Sciex Analyst software (version 1.4.1). The calibration curve was obtained through a quadratic (i.v.) or linear (p.o.) regression and the calibration range was 4-5000 ng/mL and 2-5000 ng/mL for the i.v. and p.o. studies, respectively.

Preparation of LC-MS/MS Calibration Standards

To determine the concentration of test compound in rat plasma samples, standards containing 5000, 1000, 500, 100, 50, 20, 10, 4, 2 and 1 ng/mL of the compound were prepared with rat plasma obtained from Bioreclaimation Inc. (Lot #RATBREC.47491M). Plasma standards were prepared in parallel with the plasma samples in an identical manner. Three levels of the standard stock solutions (1000, 100 and 10 ng/mL) were spiked separately into male Sprague-Dawley rat plasma and used as QC samples.

Pharmacokinetic Analysis

A total of eleven time points were obtained for each dosing route during the blood collection period. Descriptive pharmacokinetic parameters were determined from the plasma concentration-time curve by a standard non-compartmental analysis (Wagner, 1993) from each animal and dose route.

Half-life ($T_{1/2}$): Terminal half-life.

$C_{max}$: Maximum plasma concentration $AUC_{0-\infty}$: Area under the plasma concentration-time curve from time of dosing extrapolated to infinity.

CL: Total body clearance.

$MRT_{0-\infty}$: Mean residence time from the time of dosing extrapolated to infinity $Vd_{ss}$: Volume of distribution at steady state.

F: Bioavailability.

Pharmacokinetic analysis was performed by using XLFit® v.4.1 (ID Business Solutions Inc., Alameda, Calif.).

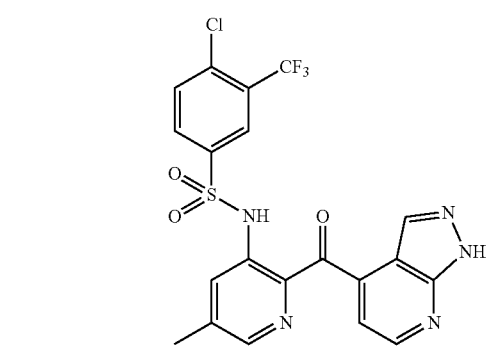 [SMILES: Cc1cnc(C(=O)c2ccnc3[nH]ncc23)c(NS(=O)(=O)c2ccc(Cl)c(C(F)(F)F)c2)c1]

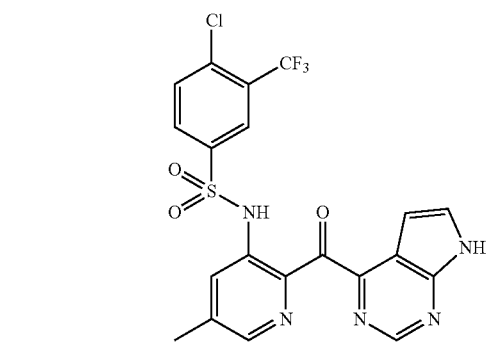 [SMILES: Cc1cnc(C(=O)c2ncnc3[nH]ccc23)c(NS(=O)(=O)c2ccc(Cl)c(C(F)(F)F)c2)c1]

| | | |
|---|---|---|
| Rat PK MRT | 35 min | 135 min |
| CYP 3A4 Inhibition IC$_{50}$ | 3 µM | 20 µM |

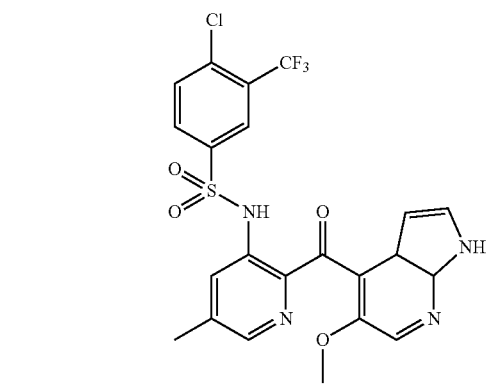 [SMILES: COC1=C(C(=O)c2ncc(C)cc2NS(=O)(=O)c2ccc(Cl)c(C(F)(F)F)c2)C2C=CNC2N=C1]

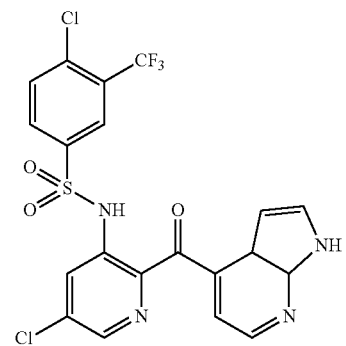 [SMILES: O=C(C1=CC=NC2NC=CC12)c1ncc(Cl)cc1NS(=O)(=O)c1ccc(Cl)c(C(F)(F)F)c1]

| | | |
|---|---|---|
| Rat PK MRT | 22 min | 135 min |
| Rat PK T$_{1/2}$ | 19 min | 161 min |
| CYP 3A4 Inhibition IC$_{50}$ | 3 µM | 20 µM |

| | | |
|---|---|---|
| Rat PK MRT | 21 min | 68 min |
| Rat PK T$_{1/2}$ | 42 min | 127 min |
| CYP 2C9 Inhibition IC$_{50}$ | 3 µM | 15 µM |

It is therefore intended that the foregoing detailed description be regarded as illustrative rather than limiting, and that it be understood that it is the following claims, including all equivalents, that are intended to define the spirit and scope of this invention.

The invention claimed is:

1. A crystalline form of 4-chloro-N-[5-methyl-2-(7H-pyrrolo[2,3-d]pyrimidine-4-carbonyl)-pyridin-3-yl]-3-trifluoromethyl-benzenesulfonamide sodium salt.

2. The crystalline form of claim 1, wherein said crystalline form has an X-ray powder diffraction comprising the following 2-theta values ±0.2 measured using CuKα radiation: 6.9, 7.7, 20.0, 24.3, 24.7, and 25.1.

3. The crystalline form of claim 2, wherein said crystalline form has an X-ray powder diffraction comprising the following 2-theta values ±0.2 measured using CuKα radiation: 6.9, 7.7, 10.6, 11.3, 11.8, 12.5, 13.7, 15.1, 15.3, 16.1, 16.9, 17.3, 18.2, 18.5, 19.5, 20.0, 21.6, 21.8, 22.6, 24.3, 24.7, 25.1, 25.6, 26.3, 27.5, 28.5, 28.8, 29.3, 31.4, and 32.4.

4. A method of modulating CCR2 function in a cell, comprising contacting the cell with a CCR2 modulating amount of the compound or salt of anyone of claims 1-3.

5. A method of treating a CCR2-mediated condition or disease comprising administering to a subject a therapeutically effective amount of a compound or pharmaceutically acceptable salt of claims 1-3.

6. The method of claim 5, wherein said CCR2-mediated condition or disease is atherosclerosis.

7. The method of claim 5, wherein said CCR2-mediated condition or disease is restenosis.

8. The method of claim 5, wherein said CCR2-mediated condition or disease is multiple sclerosis.

9. The method of claim 5, wherein said CCR2-mediated condition or disease is selected from the group consisting of inflammatory bowel disease, renal fibrosis, rheumatoid arthritis, obesity and noninsulin-dependent diabetes.

10. The method of claim 5, wherein said CCR2-mediated condition or disease is type 2 diabetes.

11. The method of claim 5, wherein said CCR2-mediated condition or disease is selected from the group consisting of chronic obstructive pulmonary disease, idiopathic pulmonary fibrosis and idiopathic pneumonia syndrome.

* * * * *